United States Patent [19]

Christensen et al.

[11] 3,962,224

[45] June 8, 1976

[54] CEPHALOSPORIN COMPOUNDS

[75] Inventors: Burton G. Christensen, Scotch Plains; Ronald W. Ratcliffe, North Plainfield, both of N.J.

[73] Assignee: Merck & Co., Inc., Rahway, N.J.

[22] Filed: Mar. 5, 1973

[21] Appl. No.: 336,561

Related U.S. Application Data

[63] Continuation-in-part of Ser. Nos. 296,356, Oct. 10, 1972, abandoned, and Ser. No. 267,845, June 30, 1972, abandoned, said Ser. No. 296,356, is a continuation-in-part of Ser. No. 244,271, April 14, 1972, abandoned, and Ser. No. 267,846, June 30, 1972, abandoned.

[52] U.S. Cl............................. 260/243 C; 424/246
[51] Int. Cl.² ....................................... C07D 501/14

[58] Field of Search ................................. 260/243 C

[56] References Cited
UNITED STATES PATENTS

| | | | |
|---|---|---|---|
| 3,594,370 | 7/1971 | Higgins et al. | 260/243 C |
| 3,634,418 | 1/1972 | Willner | 260/243 C |
| 3,769,280 | 10/1973 | Parker | 260/243 C |

*Primary Examiner*—Nicholas S. Rizzo
*Attorney, Agent, or Firm*—Walter Patton; Julian S. Levitt; J. Jerome Behan

[57] ABSTRACT

Novel 7-azido-3-cephem compounds are prepared via α-amino-phosphonoacetate esters. The cephem compounds are intermediates for the preparation of novel and known useful antibiotic cephalosporins.

4 Claims, No Drawings

CEPHALOSPORIN COMPOUNDS

This application is a continuation-in-part of U.S. application Ser. No. 296,356, filed Oct. 10, 1972 (which is a continuation-in-part of applications Ser. No. 224,271, filed Apr. 14, 1972 and Ser. No. 267,846, filed June 30, 1972) and U.S. application Ser. No. 267,845, filed June 30, 1972, all now abandoned.

The cephalosporins are valuable antibiotic substances useful in the treatment of pathogenic infections in humans and animals in addition to processing utility for a variety of industrial applications. These products can be prepared from cephalosporins such as cephalosporin C and 7α-methoxy-7β-(D-5-amino-5-carboxyvaleramido)-3-carbamoyloxymethyl-3-cephem-4-carboxylic acid which are recovered from fermentation broths produced by growing suitable strains of microorganisms. For example, cephalothin can be prepared from cephalosporin C by replacing the aminodipoyl side chain with a 2-thienylacetyl group. 7-β-Thienylacetamido-7α-3-carbamoyloxymethyl-3-cephem-4-carboxylic acid, a valuable antibiotic, can be prepared from 7-aminocephalosporanic acid or 7α-methoxy-7β-(D-5-amino-5-carboxyvaleramido)-3-carbamoyloxymethyl-3-cephem-4-carboxylic acid by processes described in the art. However, these processes for the preparation of cephalosporins suffer from several disadvantages. In the first place, the yields of cephalosporins obtained by fermentation are low, and the replacement of the aminoadipoyl groups involves a number of steps which are difficult to carry out on a commercial scale. Other processes for preparing cephalosporins starting with the penicillin nucleus and synthetic methods are also known in the art. However, these processes likewise are difficult to carry out on a commercial scale and result in obtaining only low yields of the desired products. Accordingly, other methods suitable for the preparation of cephalosporin compounds on a large scale have been sought by many workers in this art.

It is an object of this invention to provide a new method for the total synthesis of cephalosporins. Another object is to provide novel compounds which are useful as intermediates for the preparation of known antibiotic cephalosporin compounds.

The invention further relates to novel cephalosporin compounds which possess antibiotic properties. Other objects will be apparent from the detailed description of this invention hereinafter provided.

In accordance with this invention, it is now found that 7-azidocephalosporin compounds an be prepared by the processes shown in the following flowsheet:

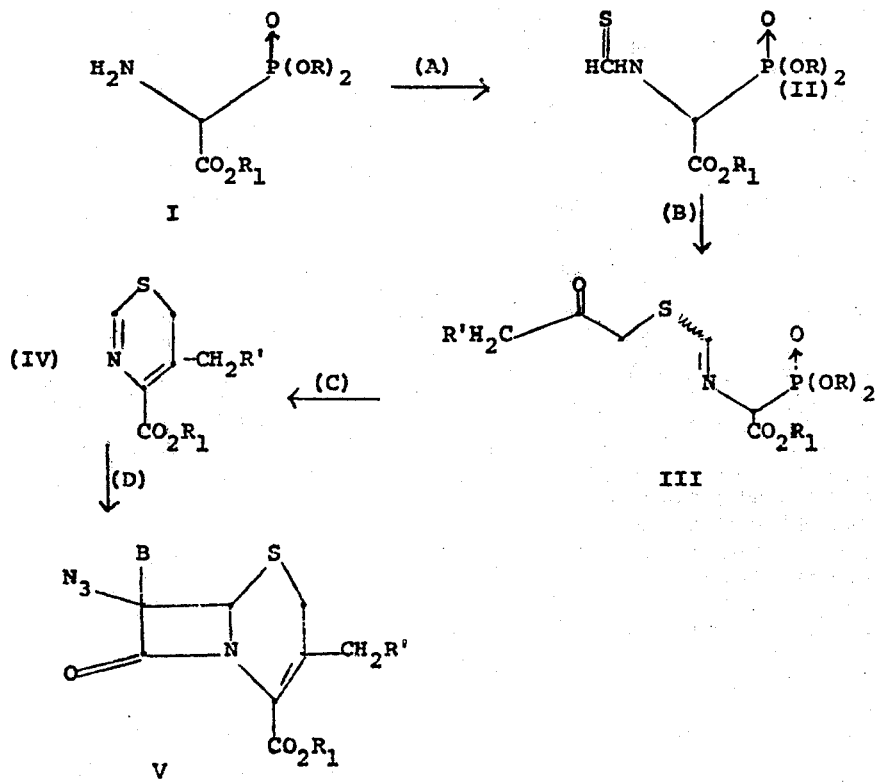

wherein B is H, CH₃ or OCH₃.

In process (A) the starting material, an ester of α-aminophosphonoacetate (I), is reacted with a thionoformate ester to produce the corresponding thioformamido ester (II). Various esters of the starting material (I) can be utlized in the above esters, Thus, phosphono esters, as for example the diloweralkyl esters or the diaryl esters, are suitable for use in this process.

Representative of the esters that may be employed include those wherein R may be the same or different, and is, for example, methyl, ethyl, propyl, butyl, pentyl, phenyl, benzyl and the like. The carboxy group of the phosphono starting material may be blocked or protected, preferably by the use of a group ($R_1$) which can be ultimately removed to obtain the free acid form of the cephalosporin without disruption of the β-lactam moiety. Protecting groups suitable for this purpose are indeed well known in this art. Examples of suitable protecting ester groups that might be mentioned are those of alcohols, phenols, and the like. $R_1$ is preferably an alkyl or aralkyl group containing from 1 to about 20 carbon atoms. Thus, $R_1$ can be a lower alkyl group such as methyl, ethyl or tertiary butyl, a substituted alkyl such as phthalimidomethyl, succinimidomethyl, phenacyl, substituted phenacyl such as p-bromophenacyl, a β-substituted ethyl group such as 2,2,2-trichloroethyl, 2-methylthioethyl or 2-(p-methylphenyl)ethyl, an alkenyl group such as 3-butenyl, propenyl, allyl, etc., an alkoxyalkyl group such as methoxymethyl, an aryloxyalkyl such as p-methoxyphenoxymethyl, an aralkyloxyalkyl group such as benzyloxymethyl, benzyl or a substituted benzyl group such as p-nitrobenzyl, p-methoxybenzyl, 3,5-dinitrobenzyl, 2,4,6-trimethylbenzyl or 3,5-dichloro-4-hydroxybenzyl, benzhydryl or a substituted benzhydryl group such as p-methoxybenzhydryl, and the like. Preferred blocking groups are methyl, tertiary butyl, phenacyl, p-bromophenacyl, p-nitrobenzyl, 2,2,2-trichloroethyl, p-methoxybenzyl, benzhydryl, methoxymethyl and p-methoxyphenoxymethyl.

Examples of representative starting materials (I) that might be mentioned are trichloroethyl α-amino-diethylphosphonoacetate, trichloroethyl α-amino-diphenylphosphonoacetate, phenyl α-amino-dimethylphosphonoacetate, p-methoxybenzyl α-amino-diethylphosphonoacetate, benzhydryl α-aminodiphenylphosphonoacetate, t-butyl α-amino-dimethylphosphonoacetate, t-butyl α-amino-dipropylphosphonoacetate, methyl α-amino-diphenylphosphonoacetate, phenacyl or p-bromophenacyl α-amino-diethylphosphonoacetate, methoxymethyl α-amino-dimethylphosphonoacetate, p-methoxyphenoxymethyl α-amino-dimethylphosphonoacetate, and p-nitrobenzyl α-amino-dimethylphosphonoacetate.

Process (A) involving the conversion of compound (I) to the corresponding thioformamido derivative (II) is carried out by reacting the phosphonoacetate with an ester of thionoformic acid such as a lower alkyl ($C_1$-$C_6$) ester at a temperature varying from 0°C. to 100°C. For example, the reaction may be carried out with ethyl thionoformate at 0°C. Generally, it is preferred to carry out the reaction in an inert solvent media such as benzene, carbon tetrachloride, methylene chloride or hexane. Alternatively, the reaction is carried out in the presence of liquid hydrogen sulfide at room temperature. After completion of the reaction, the solvent is evaporated to afford the desired product.

Alternative processes of thioformylating the α-aminophosphonoacetate include the following:

a. O-Ethyl thioformate or ethyl thionoformate at 0°C. to 30°C. in solvents such as $CCl_4$, $CH_2Cl_2$, $H_2S$ or in the absence of a solvent;

b. Sodium dithioformate or potassium dithioformate at 0°C. to 30°C. in solvents such as $H_2O$, $H_2O$-ether, $H_2O$-EtOH or $H_2O$-MeOH;

c. $H_2S$ + HCN at 0° to 30°C. in solvents such as MeOH, EtOH, $H_2O$, $H_2O$-MeOH or $H_2O$-EtOH.

Step (B) of the process comprises reacting the thioformamido intermediate (II) with a substituted acetone of the general formula $R'CH_2COCH_2X$ wherein R' represents hydrogen; lower alkoxy such as methoxy, propoxy, etc., aryloxy (phenoxy, etc.), aralkyloxy (benzyloxy, etc.), a lower alkoxy lower alkoxy group such as methoxymethoxy or a heterocyclic thio group such as 5-(1-methyltetrazolyl)thio and 2-(5-methyl-1,3,4-thiadiazolyl)thio; halo (chloro, bromo, fluoro); an acyloxy group such as acetoxy, isobutryloxy and the like; carbamoyloxy; N-substituted carbamoyloxy; N,N-disubstituted carbamoyloxy wherein the substituents may be alkyl (preferably lower alkyl of 1–6 carbon atoms; e.g., methyl, ethyl, propyl, t-butyl, hexyl); halogenated lower alkyl (e.g., trichloroethyl, etc.); lower alkoxy of 1–6 carbon atoms (e.g., methoxy, ethoxy, propoxy, etc.); araliphatic (e.g., benzyl, substituted benzyl such as p-methoxybenzyl, phenethyl and substituted phenethyl such as p-methoxyphenethyl, p-aminophenethyl, etc.) or halo (chloro, bromo, fluoro). The term lower alkyl as used herein refers to alkyl groups having 1–6 carbon atoms. X is halogen (bromo, fluoro, iodo or chloro), mesyloxy, tosyloxy, or trifluoromethyl-sulfonyloxy. The reaction may be carried out at temperatures varying from 0°C. to 50°C. in the presence of an acid scavenger to produce the corresponding S-substituted thioformimidate compound (III). Thus, the reaction is conveniently carried out by reacting the intermediate product II with the halo-substituted acetone in the presence of about one equivalent of an inorganic base such as an alkali metal carbonate, for example, NaH, potassium carbonate or nonnucleophilic organic bases such as diazobicyclononane and bis-1,8-(dimethylamino)naphthlene, at room temperature. After the reaction is complete, the product is conveniently isolated by filtering the reaction mixture and evaporating the filtrate to dryness.

Representative examples of the substituted acetones that may be employed are chloro-acetone, 1-chloro-3-acetoxyacetone, 1-chloro-3-[2-(5-methyl-1,3,4-thiadiazolyl)thio]-2-propanone, 1,3-dichloroacetone, 1-chloro-3-carbamoyloxyacetone, 1-chloro-3-(N-trichloroethylcarbamoyloxy)acetone, 1-chloro-3-methoxymethoxy-propan-2-one, 1-chloro-3-(N,N-di-p-methoxybezylcarbamoyloxy)acetone, 1-chloro-3-phenoxyacetone, 1-chloro-3-(p-methoxybenzyloxy)acetone, 1-chloro-3-isobutyryloxy-2-propanone, 1-chloro-3-benzyloxyacetone, 1-chloro-3-(p-nitrobenzyloxy)acetone, 1-bromo-3-methoxymethoxyacetone and 1-chloro-3-methoxyacetone. The substituted acetone compounds are known compounds or can be readily prepared pursuant to methods known in the art. For example, the 1-chloro-3-carbamoyloxyacetone is prepared by converting 1-chloro-3-acetoxyacetone to the dimethylketal, hydrolyzing this product to the 3-hydroxy compound, and reacting this product with sodium cyanate and trifluoroacetic acid in methylene chloride. An alternative method for the preparation of the substituted acetone involves conversion of the acid to the acid halide; reaction of the acid halide to produce the corresponding diazomethyl ketone which is then treated with HCl to produce the chloromethyl ketone as follows:

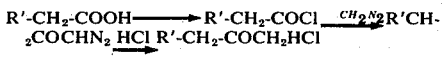

The intermediate S-substituted thioformimidate compound (III) upon reaction with a base such as an alkali metal carbonate or hydride or an organo lithium compound such as phenyllithium is converted to the corresponding thiazine compound (IV) [Step C]. Alternatively, the thiazine may be produced by the condensation of the thioformamido derivative (II) and the substituted acetone in the presence of more than about one equivalent of the base. Thus, the thiazine is produced almost exclusively when two or more equivalents of potassium carbonate are used in the condensation reaction.

Step D involves the reaction of the thiazine compound IV with an azidoacetyl reagent in the presence of an acid scavenger and preferably in a solvent medium at temperatures varying from −78°C. to 30°C. to afford the 7-azido compound (V).

The azidoacetyl reactants of particular interest have the following formula:

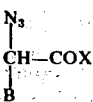

wherein B is hydrogen, methyl or methoxy and X is halogen, $OSO_2CF_3$ or $OSO_2CH_3$. The reaction is preferably carried out at low temperatures, for example at about 0°C., and in the presence of a sufficient amount of base such as a tertiary amine which serves as an acid scavenger and, in addition, catalyzes the cyclization of the intermediate thiazine compound. Thus, the reaction is conveniently carried out adding a solution of the azide in methylene chloride to a cool solution of the thiazine and a tertiary amine such as triethylamine in the same solvent; the amine being present in slight excess of the molar equivalent amount. The reaction mixture is stirred in the cold until the formation of the desired 7-azido cephalosporin compound is complete. Azidoacetyl halide and 2-azido-2-methylacetyl halide are well known and may be prepared in accordance with procedures taught in the art. The preparation of 2-azido-2-methoxyacetyl halide and the azido acetyl sulfonates are described below.

Examples of representative thiazine compounds (IV) that might be mentioned are p-methoxybenzyl 5-acetoxymethyl-6H-1,3-thiazine-4-carboxylate, methyl 5-methyl-6H-1,3-thiazine-4-carboxylate, 2,2,2-trichloroethyl 5-benzyloxymethyl-6H-1,3-thiazine-4-carboxylate, p-methoxybenzyl 5-carbamoyloxymethyl-6H-1,3-thiazine-4-carboxylate, methoxymethyl 5-isobutryloxymethyl-6H-1,3-thiazine-4-carboxylate, p-methoxybenzyl-5-(N,N-di-p-methoxybenzyl)-carbamoyloxymethyl-6H-1,3-thiazine-4-carboxylate, p-metoxybenzyl 5-(N-2,2,2-trichloroethyl)-carbamoyloxymethyl-6H-1,3-thiazine-4-carboxylate, and the like.

Alternatively, the desired 7-azido compound (V) is obtained by reacting a mixture of the acylic compound (III) and the cyclic thiazine compound (IV) or the acylic compound (III) per se with the azido-acetyl reagent under the described conditions. When the acylic compound (III) per se is reacted with the azido-acetyl halide it is postulated that a cyclic intermdiate compound of the structure

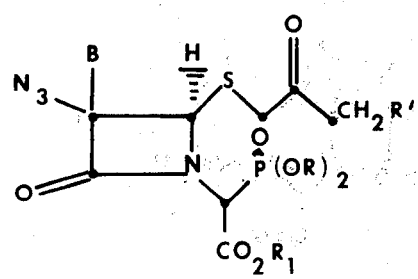

is formed, and that this product is then cyclized under the reaction conditions to the desired 7-azido compound (V).

It sould be noted that when B is hydrogen, the reaction involving the azido-acetyl reagent results in the production of a 7-α-azido cephalosporin whereas when B is $CH_3$ or $OCH_3$, the reaction of the azidomethoxyacetyl halide or azidomethylacetyl halide produces a 7-β-azido compound.

As indicated above, the acyclic precursor of the thiazine, or a mixture of the acyclic and thiazine compounds, may be used to produce the 7-azido cephalosporin. However, it is generally preferred to react the azidoacetyl reagent with the thiazine since maximum yields of the desired cephalosporin compounds are obtained under such conditions.

In the above described series of reactions the phosphonate group is used as an activating group and is finally cleaved in the preparation of the thiazine intermediate. Other starting compounds having activating groups such as

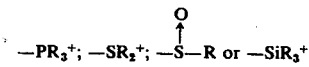

wherein R is lower alkyl (preferably methyl) or aryl (e.g., phenyl, etc.) may be employed as the starting material (I) in reaction with a thionoformate ester and ultimately cleaved in the preparation of the thiazine intermediate.

In accordance with a further embodiment of the invention, when B is hydrogen, dl-7α-azido compound (V) is reduced to obtain the corresponding novel dl-7α-amino compound (VI) as follows:

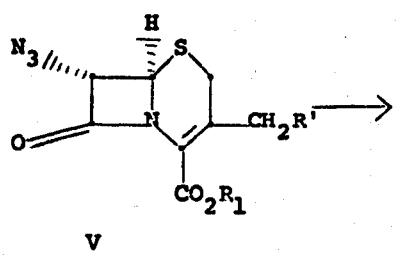

V

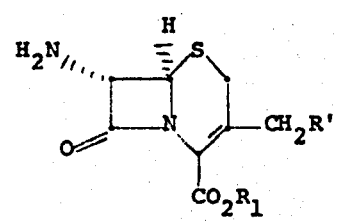

VI

For example, reduction to the amino is conveniently effected with hydrogen in the presence of a noble metal catalyst such as platinum oxide, aluminum amalgam, zinc and acetic acid or copper and thiophenone in accordance with methods known in this art. The carboxy blocking group may be readily removed to afford the 7-amino-3-$CH_2R'$-3-cephem-4-carboxylic acids in accordance with processes known in this art. For example, the benzhydryl, tertiary butyl, p-methoxybenzyl and p-methoxyphenoxmethyl groups are cleaved with an acid such as trifluoroacetic acid and the 2,2,2-trichloroethyl and phenacyl groups are cleaved by reaction with zinc and acetic acid. The term "blocking group" as utilized herein is employed in the same manner and in accordance with the teaching of U.S. Pat. 3,697,515; the contents therein with respect to said blocking group being incorporated herein by reference.

The novel 7α-azido and 7α-aminocephalosporin compounds otained therefrom (wherein B is hydrogen) are obtained as mixtures of the d and l enantiomers which can be resolved in accordance with methods known in this art to obtain the optically-active forms. The novel dl 7α-amino compounds or the enantiomers thereof can be converted to the corresponding novel dl 7β-aminocephalosporin compounds by procedures hreinafter described and these 7β-substituted compounds can be acylated to produce novel dl cephalosporins having valuable antibiotic properties. Alternatively, as is hereinafter shown, the dl 7α-azido compounds can be converted to obtain antibiotically active 7-substituted, for example 7-methoxy, or 7-methyl, cephalosporins.

A method by which the dl 7-α-azido compounds can be converted to obtain antibiotically active 7-methoxy or 7-methyl cephalosporins is as follows:

FLOW SHEET

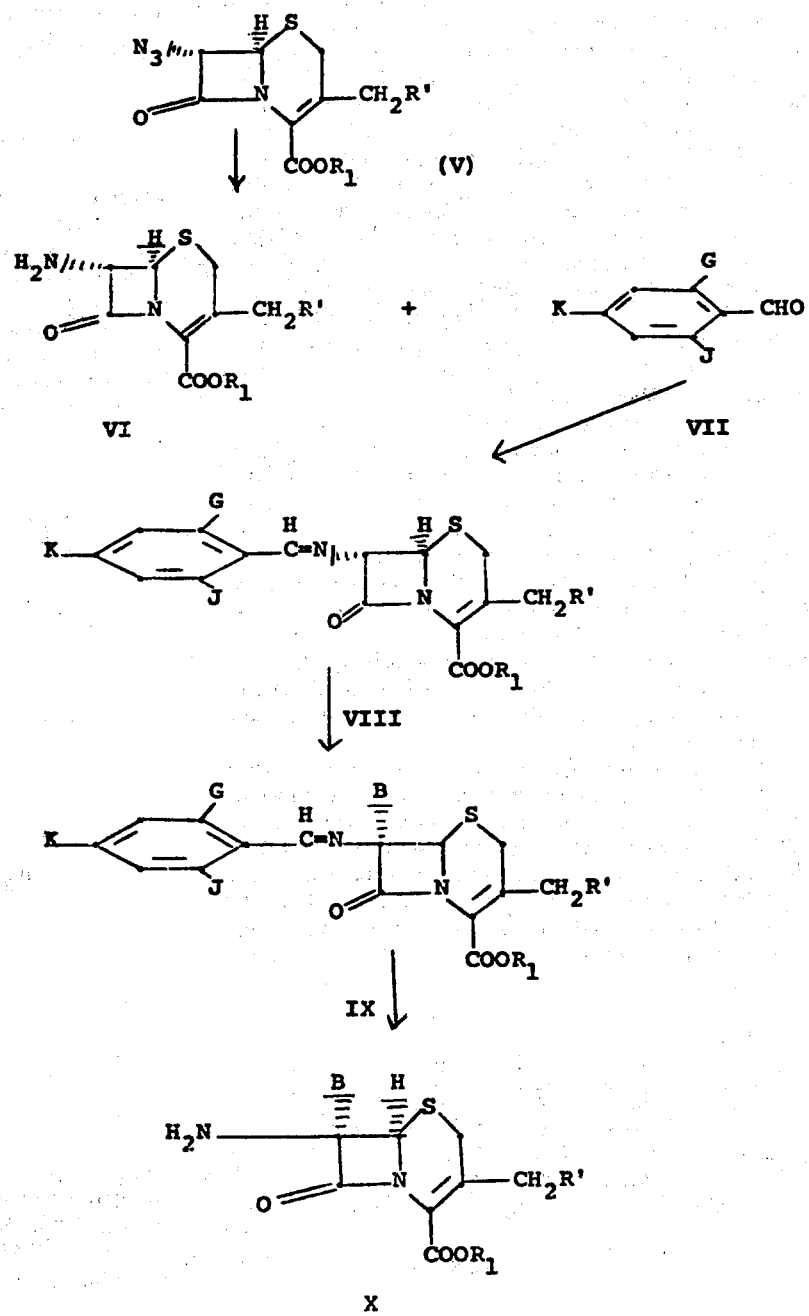

The process can be summarized briefly as having three major steps: the first is the preparation of the imino derivative of the 7-amino cephalosporin. This imino derivative is then substituted with the chosen reactant supplying the B group desired ($CH_3$ or $OCH_3$). The specific reactant depends on the identity of the B group. The third step is then the regeneration of the amino group.

The dl 7-$\alpha$-azido starting material is reduced via methods known to the art to the dl 7-$\alpha$-amino cephalosprin. The reactant VII employed in the reaction with the 7$\alpha$-amino is an aromatic aldehyde, optionally having at least one o- or p-electronegative substituent. In other words, at least one of J, G, and K may be a substituent selected from the group consisting of nitro, halo, sulfonyl, carboxyl derivatives such as esters or amides, cyano, and the like. The other two of J, G, and K can either be one of the above electronegative substituents, or hydrogen. The preferred reactants are p-nitrobenzaldehyde, where J=nitro, and G and H-hydrogen, and banzaldehyde.

Other carbonyl containing compounds, e.g., aldehydes and ketones such as acetone, hexafluoroacetone or chloral which will form stable imino derivatives will also be operable in this invention. Also, polycyclic aromatic aldehydes can be used, i.e., having 2-3 fused ring nuclei.

The dl 7$\alpha$-amino cephalosporin VI and the aromatic aldehyde VII are mixed together in approximately equimolar amounts in an inert solvent. Suitable solvents are ethanol, dioxane, acetonitrile, dimethylformamide, tetrahydrofuran, dimethylsulfoxide, benzene, toluene, methylene chloride, chloroform, and the like. The reaction proceeds readily at temperatures ranging from ambient to reflux temperature of the solvent. Since this condensation is an equilibrium reaction and since water is one of the products of the reaction, water is removed from active participation in further reactions by any of a number of usual methods, including azeotropic distillation, molecular sieves, chemical entrapment using potassium carbonate, magnesium sulfate, etc., or borate esters. The particular method is dependent upon the exact parameters of the reaction. The reaction is terminated by evaporation of the solvent. The imino derivative VIII is then recovered and used in the next step.

The latter involves the substitution of the B group at the carbon atom adjacent to the imino nitrogen. This reaction takes place in the presence of an inert solvent, such as those listed above, and in the additional presence of an activating agent which is an organic or inorganic base.

The activating agent can be any of a number of organic or inorganic basis. Tertiary (loweralkyl) amines are suitable, such as triethylamine, diisopropyl ethylamine; lower alkyl is used as having 1-4 carbon atoms and can be the same or different. Pyridine is also used. Lithium alkyls and lithium aryls, such as lithium alkyls having 1-4 carbon atoms, e.g., t-butyl lithium or phenyl lithium, could be used. Sodium hydride, lithium amides such as lithium diisopropylamide, and potassium t-butoxide are also suitable.

The activating agent is added to the solution of compound VIII at a low temperature ($-100°$ to $0°C$. and preferably $-100°$ to $60°C$.) and under an inert atmosphere. The amount of activating agent employed is sufficient to produce a strong color change in the solution. The color is an indicator that the activated form of compound VIII is present.

The activated compound VIII is not isolated, but the next reagent is added directly to the reaction mixture.

The specific reagent which is employed in the reaction with the activated compound VIII to result in the substitution of the chosen B group obviously depends on the B group desired.

In the case of B = $OCH_3$ the reagent can be dimethyl peroxide, methyl t-butyl peroxide, methylphenylsulfenate, o-methyldimethyl sulfoxonium methoxulfate, or N-methoxy pyridinium methosulfate. It may be noted that an alternative method for the inroduction of the $OCH_3$ group involves reaction of activated VIII with a halogenating agent such as N-bromosuccinimide followed by methanolysis. Where B = $CH_3$ the following reagents may be employed: methyl sulfate, methyl chloride, methyl bromide and methyl iodide.

Once the compounds IX have been prepared, the imino moiety is converted to the amino moiety of compound X.

The regeneration of X from IX takes place by the reaction of IX with an amine in the presence of an acid catalyst. The amine employed can be aniline, hydrazine, or hydrazine derivatives such as phenylhydrazine, 2,4-dinitrophenyl hydrazine, and the like. The acid catalyst can be any commonly used strong organic or inorganic acid such as hydrochloric acid or p-toluene sulfonic acid. One preferable combination utilizes aniline hydrochloride, which serves as both acid and amine. Another preferred combination is 2,4-dinitrophenyl hydrazine and p-toluene sulfonic acid. The reaction conditions of the regeneration are chosen such that no undesired hydrolysis or ring damage occurs, and is preferably carried out in a lower alkanol medium (1-5 carbon atoms), such as methanol, ethanol, and the like, although other solvents including dimethoxyethane or dimethyl formamide may also be used. The temperature is that of the surroundings. The relative amounts of acid and amine employed depends on the specific aldehyde VII and amine used, since the regeneration involves an equilibrium. The choice of amounts of the reagents is within the skill of one in the art. IX can be hydrolyzed with $PaCl_2$ in the presence of $H_2O$.

Compounds VIII and IX prepared in the reactions can be used to prepare valuable antibacterial agents useful against gram-positive and gram-negative bacteria. When the amino group of compound X is acylated as illustrated below the resulting products have activity against gram-negative organisms.

An alternative procedure by which the novel dl-7-azido compounds may be converted to useful antibiotically active 7-methoxy cephalosporins is as follows:

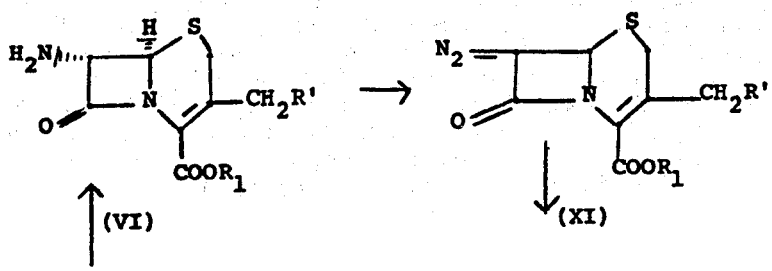

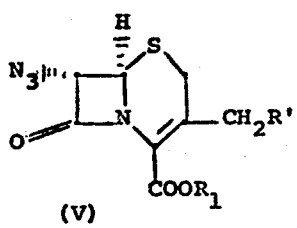

(V)

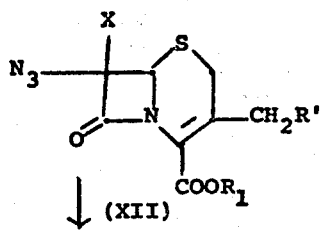

↓ (XII)

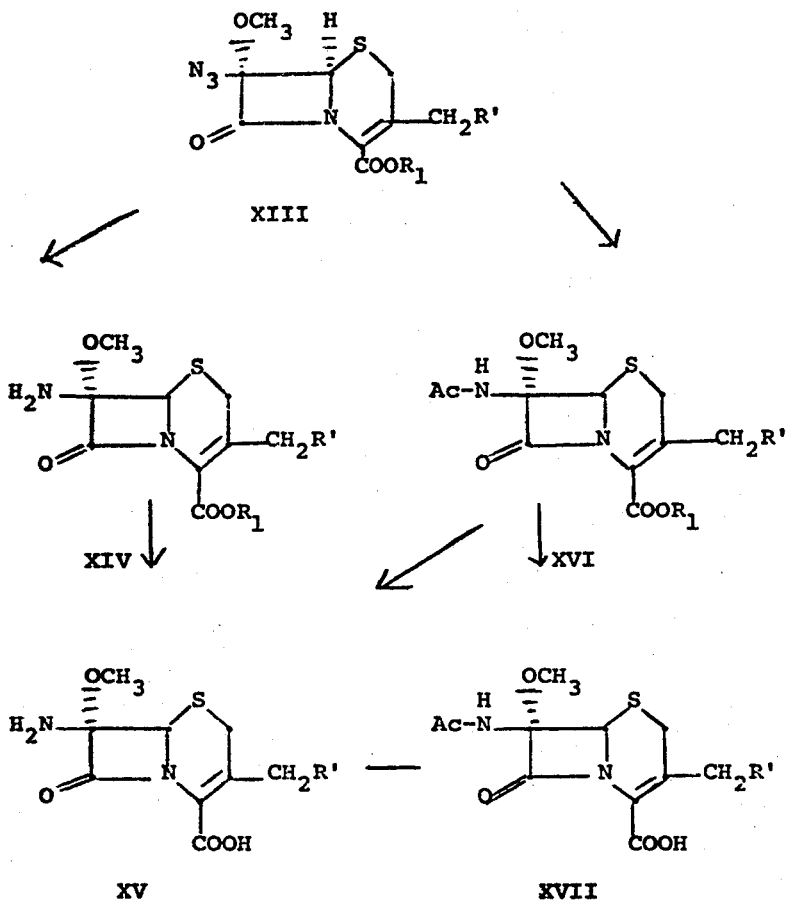

where the substituents are as defined above.

In the above process the novel dl 7-azido compound V is reduced to the 7-amino cephalosporin VI. The 7-amino compound is converted to the corresponding 7-diazocephalosporin acid ester by reaction with nitrite. It should be noted that although the 7α-amino compound is illustrated in the above flow sheet, it will be appreciated that the 7β-cephalosporin formed by epimerization of the 7α-amino compound can also be employed in the above sequence of reactions leadding to antibiotically active 7-methoxy cephalosporins. The 7-diazocephalosporanic acid ester XI is then reacted with a halo azide from the group consisting of bromine, chlorine or iodine azide, preferably in the presence of a tertiary amine azide, to produce the intermediate 7-halo-7-azidocephalosporanic acid ester XIi which on reaction with a suitable nucleophilic reagent is converted to the desired 7-OCH$_3$-7-azidocephalosporanic acid ester XIII. This intermediate product is reduced and acylated in one step to form the substituted cephalosporanic ester XVI which can then be cleaved to remove the blocking group and obtain the cephalosporanic acid or a salt thereof XVII. Alternatively, as shown in the flowsheet, the 7-OCH$_3$-7-azidocephalosporanic acid ester XIII is reduced to the 7-OCH$_3$-7-aminocephalosporanic acid ester XIV which can be acylated to produce the 7-OCH$_3$-7-acylaminocephalosporanic acid ester XVI. Alternatively, the ester group of compound XIV can be cleaved to obtain the free acid XV which can be acylated to form the desired substituted cephalosporin or a salt thereof. The step of cleaving the blocking group is readily effected in accordance with methods known in this art. For example, an aralkyl group such as the benzyl ester is removed by reduction, a silyl ester can be removed by hydrolysis to form the free acid or a salt thereof and a benzhydryl group is readily cleaved by reaction with trifluoroacetic acid in the presence of anisole. In this process other esters which are readily cleaved to form the free acid such as trichloroethyl, phthalimidomethyl, succinimidomethyl, p-metoxybenzyl, p-nitrobenzyl, phenacyl and t-butyl and the like can be used. Also, as is discussed above, the 3-substituent on the Δ³-cepham nucleus can be varied following the procedures known in this art to obtain the useful cephalosporins.

The diazotization of the 7-amino ester is carried out in accordance with processes well known in this art. Thus, it is conveniently effected in aqueous or aqueous-organic solvent medium, for example by reaction with sodium nitrite in the presence of an acid or by reaction with an organic nitrite. Organic solvents suitable for carrying out this reaction are those which do not contain an active hydrogen. Examples of such solvents that might be mentioned are methylene chloride, ether, benzene, toluene, chloroform, and the like. The reaction is preferably carried out at temperatures between about 0° and 50°C.; usually it is most conveniently effected at room temperature. The isolation of the desired diazo compoumd is readily accomplished in accordances with methods known in the art.

The step of producing the halo azide intermediate is carried out by reacting the diazo compound with a halo azide at a temperature between about −25° and 50°C. for sufficient time to complete the formation of the desired compound. The reaction is preferably carried out in a suitable organic solvent medium which is inert to the reactants. Various solvents which do not contain an active hydrogen such as methylene chloride, chloroform, benzene, toluene, ether and the like, or mixtures thereof provide suitable mediums for carrying out the reaction. Generally, it is preferred to effect the reaction in the presence of a second azid such as lithium azide or a tertiary ammonium azide, for example triethylammonium azide, since under these conditions the formation of the undesired 7-dibromo compound is avoided. The halo azide is used in an amount in slight excess of stoichemetric requirements. The amount of second azide is not critical and it is generally desirable to use an excess in order to obtain maximum yields of the desired halo azido compound under optimum conditions. After completion of the formation of the halo azide the product is recovered and can be purified further, for example by chromatography, in accordance with processes well known in this art.

The next step of the process comprising the replacement of the halo substituent by a methoxyl group is effected by reacting the halo azide with a substance capable of furnishing an OCH₃ group to replace the halo. This reaction is preferably carried out in the presence of a suitable non-reactant solvent such as methylene chloride, chloroform, benzene, toluene, ether, petroleum ether and the like; again it is desirable to avoid using any solvents containing an active hydrogen. Thus, the nucleophilic displacement reagent can be methanol which results in the displacement of the halo group and the introduction of a methoxy group. The reaction is preferably carried out in the presence of a heavy metal cation such as a silver salt.

In the next step of the above-described process the 7-azido-7-OCH-hd 3 compound is then reduced to afford the corresponding 7-amino-7-OCH₃ compound. Various methods of carrying out this reduction can be employed, but it is generally preferred to carry out the reduction of the azido to the amino group by catalytic hydrogenation employing a noble metal catalyst such as platinum, palladium or oxides thereof. These processes are carried out in accordance with procedures well known in this art. Alternatively, the reduction can be effected in the presence of a suitable acylating agent to produce the desired 7-acylamido-7-OCH₃ compound. The 7-amino compound can be reacted with suitable acylating agents using procedures well known in this art as described hereinafter to obtain the desired 7-acylamido compounds.

In accordance with a further embodiment of this invention the novel dl 7β-aminocephalosporin compounds of the invention may be acylated to obtain the corresponding novel dl 7β-acylamido cephalosporin compounds which are active against pathogenic gram-negative and gram-positve bacteria. Acylation of the novel dl 7α-amino cephalosporins results in the preparation of novel dl 7α-acylamido compounds which may be converted by known methos to novel anitbiotically active dl-7β-acylamido cephalosporins. The novel dl 7-acylamido cephalosporins may be resolved into the respective d- and l-isomer utilizing resolution techniques well known to the art. As indicated above, the novel dl 7α-azido or dl 7α-amino cephalosporin compounds may be resolved to produce the corresponding d- or l-isomer which may be converted to known useful cephalosporins employing techniques well known in the art.

The novel dl 7α- or 7α-cephalosporins of the invention have the following formula:

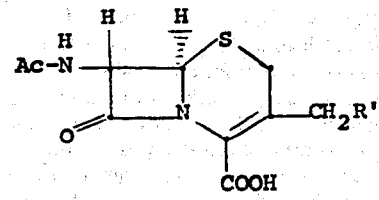

and salts and esters thereof wherein R' is as defined above; and Ac is an acyl group, for example an acyl group such as those of useful penicillins and cephalosporins known in this art. Pursuant to a preferred embodiment Ac is represented by the formula

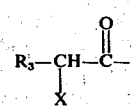

wherein X is hydrogen, halogen, amino, guanidine, phosphono, hydroxy, tetrazolyl, carboxy, sulfo, or sulfamino; R₃ is hydrogen, phenyl, substituted phenyl, an N-substituted acetimidoyl amino such as N-(phenylacetimidoyl)amino, a moncyclic heterocyclic 5- or 6-membered ring containing one or more oxygen, sulfur or nitrogen atoms in the ring, substituted heterocycles, phenylthio, phenyloxy, heterocyclic or substituted heterocyclic thio groups, lower alkyl (1–6 carbon atoms), or cyano; the substituents on the R₃ group being halo, carboxymethyl, guanidino, guanidinomethyl carboxamidomethyl, aminomethyl, nitro, methoxy or methyl. Paricularly preferred are acyl groups where X is hydrogen, hydroxy, amino or carboxy and R₃ is phenyl, lower alkyl or a 5- or 6-membered heterocyclic ring having one or two sulfur, oxygen or nitrogen hetero atoms. Thus, specific $R_3$ sustituents that might be mentioned as preferred substituents are thiazolyl, thienyl, furyl, N-(phenylacetimidoyl)amino and phenyl.

In accodance with this invention, it is now found that novel dl 7β-azido-7-methoxy cephalosporin compounds and 7β-azido-7-methyl cephalosporin compounds are prepared by reacting a 5-substituted-6H-1,3-thiazine-4-carboxylic acid ester with a 2-azido-2-methoxyacetyl halide or a 2-azido-2-methylacetyl halide as shown in the following equation:

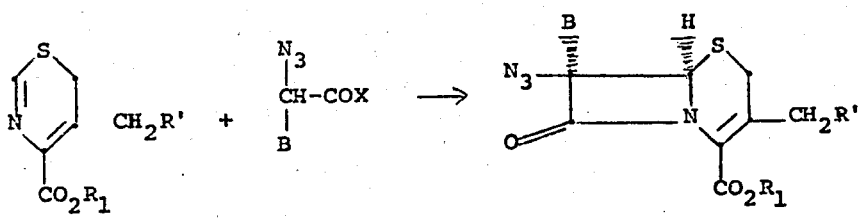

wherein $R_1$, R' and X are as set forth above and B is -$CH_3$ or -$OCH_3$.

Pursuant to a further embodiment of our invention, the novel dl-7β-azido-7methoxy and dl-7β-azido-7-methyl cephalosporin compounds of this invention are reduced, for example by hydrogenation in the presence of a catalyst, preferably a noble metal catalyst such as platinum oxide, to produce the corresponding dl-7β-amino-7-methoxy and dl-7β-amino-7-methyl cephalosporin compounds. The racemic 7β-azido compounds of this invention can be resolved to obtain the individual isomers in accordance with methods known in the art for the resolution of racemates. Alternatively, the dl-cephalosporin compounds obtained by acylation of the dl-7β-amino compounds can be resolved.

The novel dl-7β-azido-7-methoxycephalosporin and dl-7β-azido-7-methyl cephalosporin compounds of the present invention can be converted to novel racemic 7β-acylamido-7-methoxy or 7-methyl cephalosporin compounds. This involves reducing the azide to the corresponding 7β-amino compound and acylating this intermediate product to obtain the corresponding novel dl 7β-acylamido-7-methoxycephalosporin ester or 7β-acylamido-7-methyl cephalosporin ester which is then deblocked to obtain the free acid and salts thereof. Thus, the new racemic compounds of this invention can be used to prepare racemic cephalosporins such as 7-methoxy-7β-phenylacetamidocephalosporanic acid, 7-methyl-7β-(2-thienylacetamido)-3-carbamoyloxymethyl3-cephem-4-carboxylic acid, and 7-methoxy-7β-(2-thienylacetamido)-3-carbamoyloxymethyl-3-cephem-4-carboxylic acid and their salts. These products are antibiotics which are active against various gram-negative and gram-positive pathogens. These racemates can also be resolved by procedures known in the art to obtain the individual isomers.

Thus, in accordance with a further embodiment of this invention, the novel dl-7β-aminocephalosporin compounds can be acylated to obtain new dl cephalosporin compounds of the formula:

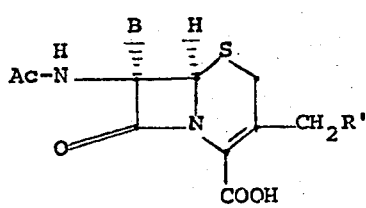

and salts and esters thereof wherein R' is as defined above, B is -$CH_3$ or -$OCH_3$, and Ac is an acyl group as defined above, such as those of penicillins and cephalosporins known in this art. The above dl-cephalosporin compounds are active against gram-negative and gram-positive bacteria. It should be noted that the racemates of the invention which have approximately one-half the activity of the particular isomer of interest may be resolved to obtain the active enantiomer in accordance with techniques well known to the art.

Thus, the novel dl cephalosporins of this invention are prepared by the acylation of the corresponding substituted novel dl 7-aminocephalosporanic acid compounds. This embodiment of the present invention can be illustrated by the following reactions:

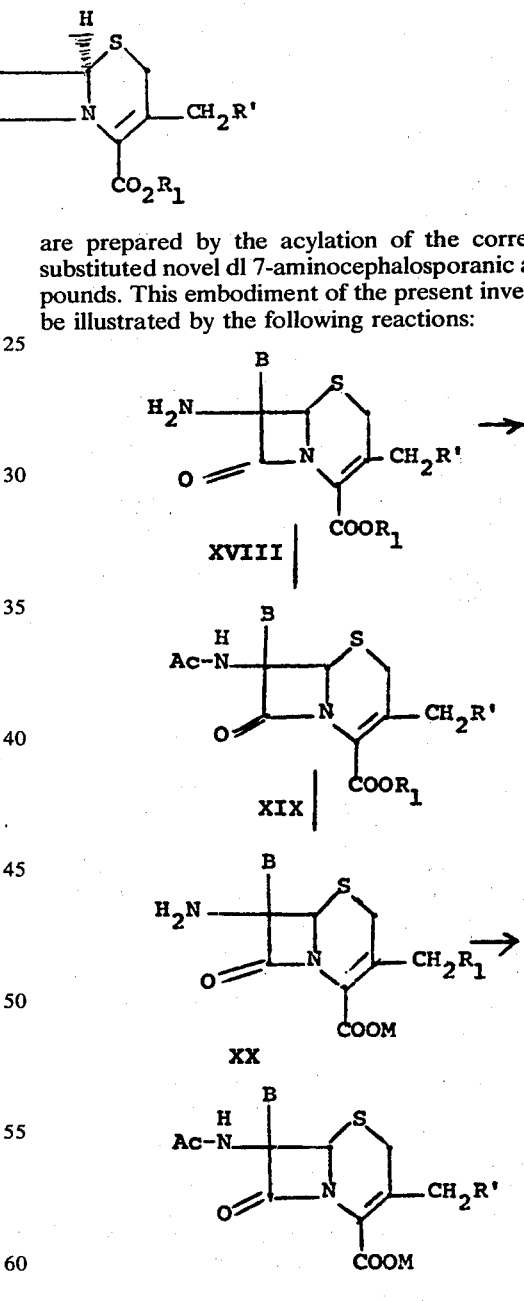

wherein B is H, $OCH_3$ or $CH_3$, M represents hydrogen, a metal cation or an amine, R', Ac are the same as defined above and $R_1$ represents a blocking group. In accordance with the foregoing flowsheet, the dl 7α- or 7β-aminocephalosporanate XVIII is acylated to form the corresponding cephalosporin derivative XIX which is deblocked to form the desired cephalosporin XXI or a salt thereof. Alternatively, the amino-cephalosporin can first be deblocked to produce the corresponding acid or a salt thereof XX, and this intermediate can then be acylated to obtain the desired cephalosporin or a salt thereof.

The acylation of the 7-amino-cephalosporanic acid compound is readily effected by reaction with an acylating agent such as an acyl halide (chloride or bromide) or a functional equivalent thereof such as an acid anhydride, a mixed acid anhydride with other carboxylic acids and particularly lower aliphatic esters of carboxylic acid, a carboxylic acid in the presence of a carbodiimide such as 1,3-dicyclohexylcarbodiimide, an activated ester and the like, or enzymatic acylation pursuant to acylation methods used for the preparation of cephalosporins which are well known in this art.

As discussed above, the 7-substituted-7-aminocephalosporanic acid compound acylated can be a suitably blocked ester, such as the benzhydryl, trichloroethyl, trimethylsilyl, phenacyl or methoxymethyl ester which is removed in accordance with the procedures known in the art to produce the desired cephalosporin or a salt thereof. Thus for example, when the blocking group is benzhydryl, it can be readily removed by reaction with trifluoroacetic acid in the presence of anisole. Alternatively, the 7-aminocephalosporanic acid ester can first be converted to the free acid by this procedure and the salt of the free acid such as the sodium salt or an amine salt can be acylated pursuant to procedures well known in the art which are used for the conversion of 6-aminopenicillanic acid and 7-aminocephalosporanic acid to produce various penicillins and cephalosporins.

It may be noted that the substituent at the 3-position of the cephalosporin nucleus may be converted to or readily replaced by other R' substitutents pursuant to methods well known in this art. For example, upon treating the 3-acetoxymethyl substituted cephalosporanates of this invention with a suitable reagent or combination of reagents, it is possible to substitute various substitutents for acetoxy at the 3-position of the cephalosporin nucleus. Suitable reagents include, for example, phosgene and a secondary amine, isocyanates, alkali metal toluenesulfinates, alkali metal azide, polyhydroxybenzene, N-loweralkyl indole, thiourea, mercaptans, phosphorus pentachloride, thiocyanates, cycloalkyl xanthates, pyridine, thiobenzoic acid, N-alkyl and N,N-dialkylthioureas or alkali metal N-alkyl and N,N-dialkylthiocarbamates and the like.

Thus, by reaction with a quaternary ammonium compound, for example pyridine, the 3-acetoxy cephalosporin is converted to the corresponding 3-pyridinomethyl compound. Alternatively, the 3-acetoxy cephalosporins upon treatment with citrus acetylesterase are converted to the corresponding 3-hydroxymethyl compounds which can be acylated to produce other 3-acyloxymethyl including carbamoyloxymethyl, or acylthiomethyl compounds. Similarly, other 3-substituted cephalosporin compounds are prepared following procedures well known in this art.

One method for the introduction of an N,N-diloweralkylcarbamoyloxymethyl or heterocyclic aminocarbonyloxymethyl moiety at position 3 of the instant products connsists in treating a 3-hydroxymethyl analog and a 3-hydroxymethyl-7-methoxy-7-(2-thienylacetamido)cephalosporanic acid with phosgene and a diloweralkylamine in the presence of a base. In this manner the following products can be obtained: sodium dl-3-(N,N-dimethylcarbamoyloxymethyl)-7-methoxy-7-(2-thienylacetamido)decephalosporanate and sodium dl-3-(pyrrolidinylcarbonyloxymethyl)-7-methoxy-7-(2-thienylacetamido)decephalosporanate.

The N-mono substituted carbamoyloxymethylcephalosporin products are obtained by treating a 3-hydroxymethyl-7-amidodecephalosporanate with a suitable isocyanate. In this manner sodium dl-3-(N-methylcarbamoyloxymethyl)-7-methoxy-7-(2-thienylacetamido)decephalosporante is obtained by treating sodium dl-3-hydroxymethyl-7-methoxy-7-(2-thienylacetamido)decephalosporante with methylisocyanate in the presence of sodium bicarbonate.

The unsubstituted carbamoyloxymethyl may be obtained by cleaving an N mono- or di-substituted carbamoyloxymethyl material such as N,N-di-p-methoxybenzylcarbamoyloxymethyl or N-2,2,2-trichloroethyl carbamoyloxymethyl. An alternative method for obtaining the carbamoyloxymethyl group at the 3-position involves treating the 3-hydroxymethyl analog with trichloroacetylisocyanate or chlorosulfonylisocyanate, followed by hydrolysis.

In accordance with a further embodiment of this invention, it is found that the α-aminophosphonoacetate ester (I) used as the starting material in the process described above is obtained by the processes shown in the following flowsheet:

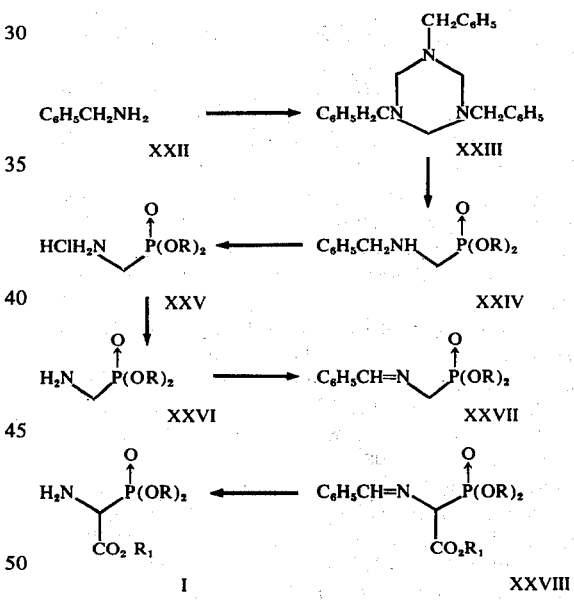

wherein R and $R_1$ are as defined above.

In accordance with the above-depicted reactions, benzylamine is first reacted with formaldehyde to obtain the 1,3,5-tribenzyl-sym-hexahydrotriazine XXIII. The latter compound on reaction with a di-substituted phosphite is converted to the phosphonate XXIV. This reaction is conveniently effected by heating a mixture of the di-substituted phosphite with the triazine at 100°C. for sufficient time to complete the formation of the desired intermediate product which is conveniently isolated as an acid salt, such as the hydrochloride. Reduction of the intermediate N-benzylaminomethylphosphonate acid salt in the presence of palladium on carbon affords the salt of the corresponding amino compound XXV. The acid salt is converted to the amine by reacting it with ammonia in a suitable solvent medium such as chloroform. After removing the precipitated ammonium salt, the desired product is readily recovered by evaporating the solvent to obtain the aminomethylphosphonate ester XXVI. Alternatively, the acid salt XXV is neutralized with aqueous $K_2HPO_4$ and the free amine XXVI is extracted into an organic solvent such as $CH_2Cl_2$. This latter product on reaction with an aldehyde such as benzaldehyde is converted to the corresponding Schiff base XXVIII, which on reaction with a strong base eg. an organolithium compound such as phenyllithium and then a haloformate ester is converted to the imine XVIII. Treatment of this imine with 2,4-dinitrophenyl hydrazine in the presence of p-toluenesulfonic acid monohydrate or with p-toluenesulfonic acid hydrate in ether followed by neutralization of the amine acid salt affords the desired α-aminophosphonoacetate ester (I).

The following examples are presented as illustrative emboidments of the various processes described above.

EXAMPLE 1

1,3,5-Tribenzyl-sym-hexahydrotriazine

To a stirring solution of benzylamine (110 ml., 1 mole) in absolute ethanol (100 ml.) is added rapidly 37% aqueous formaldehyde (75 ml., 1 mole). The temperature of the mixture rises to 83°C., then subsides. After having been stirred for 2 hours, the reaction mixture is added to petroleum ether (1000 ml.), washed with water (2 × 300 ml.) and saturated brine (300 ml.), dried over $MgSO_4$, and evaporated under reduced pressure to yield a clear oil (117.5 g.) which solidifies upon scratching. Recrystallization of the crude product from petroleum ether gives 1,3,5-tribenzyl-sym-hexahydrotriazine (103.0 g.), m.p. 48°–50°C. ir ($CCl_4$) 1495, 1456, 1362, 1172, 1124, 1020, 924 and 699 cm$^{-1}$; nmr ($CDCl_3$) τ 6.62 (s, 6, C$\underline{H}_2$), 6.38 (s, 6, C$\underline{H}_2$) and 2.78 (s, 15, Ar$\underline{H}$).

EXAMPLE 2

Diethyl N-benzylaminomethylphosphonate

A mixture of diethyl phosphite (57.5 g., 0.416 mole) and 1,3,5-tribenzyl-sym-hexahydrotriazine (49.6 g., 0.139 mole) is heated at 100°C. for 6 hours in a flask protected from moisture by a drying tube, and then allowed to cool gradually to room temperature overnight. Chromatography of the crude product on silica gel (2270 g., packed under methylene chloride) using 3% methanol in methylene chloride as eluting solvent gives diethyl N-benzylaminomethylphosphonate (63.2 g.) as a pale yellow, mobile liquid. ir ($CCl_4$) 1244, 1062, 1034, 966 and 698 cm$^{-1}$; nmr ($CDCl_3$)τ8.70 (t, 6, J=7Hz, C$\underline{H}_3$), 8.33 (brs, 1, N$\underline{H}$), 7.08 (d, 2, J=13Hz, C$\underline{H}_2$), 6.15 (s, 2, PhC$\underline{H}_2$), 5.88 (p, 4, J=7Hz and J=7Hz, C$\underline{H}_2$CH$_3$), 2.72 (s,5,Ar$\underline{H}$).

EXAMPLE 3

Diethyl aminomethylphosphonate hydrochloride

A solution of diethyl N-benzylaminomethylphosphonate (30.1 g., 0.117 mole) in absolute ethanol (400 ml.) is treated with 0.9 N HCl in ethanol (130 ml.) and hydrogenated at 45 psi with 10% palladium on carbon (6.6 g.) for 19 hours. The resulting mixture is filtered through a packed pad of diatomaceous earth to remove the catalyst. Evaporation of the filtrate under reduced pressure gives a clear residue which is successively dissolved in ethanol and benzene and evaporated in vacuo to give diethyl aminomethylphosphonate hydrochloride (23.2 g.) as a white powder. nmr (DMSO-$d_6$)τ8.73 (t, 6, J=7Hz, CH$_2$C$\underline{H}_3$), 6.76 (d, 2, J=13.5Hz, C$\underline{H}_2$), 5.87 (d of q, 4, J=7Hz and J=8Hz, C$\underline{H}_2$) and 1.42 (br s, 3, N$\underline{H}_3$).

EXAMPLE 4

Diethyl aminomethylphosphonate

Diethyl aminomethylphosphonate hydrochloride (4.965 g.) is stirred in chloroform (25 ml.) at 0°C. while ammonia is bubbled through the mixture for 4 minutes. The resulting ammonium chloride is filtered off and the filtrate dried briefly over $MgSO_4$. Evaporation of the solvent at reduced pressure affords diethyl aminomethylphosphonate (4.031 g.) as a clear liquid. ir ($CCl_4$) 1240, 1062, 1032, and 966 cm$^{-1}$; nmr ($CDCl_3$)τ8.67 (t, 6, J=7Hz, C$\underline{H}_3$), 7.03 (d, 2, J=11Hz, C$\underline{H}_2$), and 5.86 (p, 4, J=7Hz and J=7Hz, C$\underline{H}_2$CH$_3$).

EXAMPLE 5

Diethyl N-benzylidene-aminomethylphosphonate

Diethyl aminomethylphosphonate (4.03 g., 24.1 mmole) is stirred in an ice bath while benzaldehyde (2.50 ml., 24.5 mMol) is added dropwise over a period of 5 minutes. After having been stirred an additional 15 minutes at 0°C., the mixture is diluted with absolute ethanol (20 ml.) and evaporated in vacuo. The residue is dissolved in dry benzene (20 ml.) and evaporated to give diethyl N-benzylidene-aminomethylphosphonate (6.073 g.) as a pale yellow oil: ir ($CCl_4$) 1639, 1250, 1062, 1037, and 971 cm$^{-1}$; nmr ($CDCl_3$)τ8.68 (t, 6, J=7 Hz, C$\underline{H}_3$), 5.93 (d of d, 2, J=17.5 Hz and J=1 Hz, C$\underline{H}_2$), 5.85 (d of q, 4, J=8 Hz and J=7 Hz, C$\underline{H}_2$CH$_3$), 2.65 (m, 3, Ar$\underline{H}$), 2.29 (m, 2, Ar$\underline{H}$), and 1.75 (t of d, 1, J=1 Hz and J=5 Hz, =C$\underline{H}$).

EXAMPLE 6

Trichloroethyl N-benzylidene-α-amino-diethylphosphonoacetate

Phenyllithium (12.5 ml. of a 2.0M solution in 7:3 benzene-ethyl ether) is added to a dry-ice cooled, stirring solution of diethyl N-benzylidene-aminomethylphosphonate (6.073 g., 23.8 mMol) in dry tetrahydrofuran (130 ml.). After having been stirred for 30 minutes at −78°C. under a $N_2$ atmosphere, the solution is treated dropwise over 25 minutes with a solution of trichloroethyl chloroformate (5.04 g., 23.8 mMol) in dry tetrahydrofuran (25 ml.). The resulting solution is stirred an additional 2 hours at −78°C., then allowed to warm to 3°C. over a period of 30 minutes. Evaporation of the solvent in vacuo yields a yellow foam which is partitioned between ethyl ether (150 ml.) and 0.5M pH3 phosphate buffer (50 ml.). The aqueous phase is separated and extracted with two additional portions of ether (25 ml.). The combined ethereal solution is washed with saturated brine (100 ml.), dried over $MgSO_4$, and evaporated under reduced pressure to give a cloudy, yellow oil. Chromatography of the crude product on silica gel (200 g.) using 9:1 ethyl acetate-acetone as eluting solvent gives trichloroethyl N-benzylidene-α-amino-diethylphosphonoacetate as a pale yellow oil.

The corresponding methyl ester is obtained in a similar manner as a pale yellow oil, using methylchloroformate instead of trichloroethyl chloroformate: ir ($CCl_4$) 1748, 1638, 1261, 1160, 1057, 1029, 977, 912, and 691 cm$^{-1}$; nmr (CDCl$_3$)τ8.68 (t, 6, J=7 Hz, CH$_2$C$\underline{H}_3$), 6.22 (s, 3, C$\underline{H}_3$), 5.77 (d of q, 4, J=9 Hz and J=7 Hz, C$\underline{H}_2$CH$_3$), 5.25 (d, 1, J=21 Hz, C$\underline{H}$), 2.56 (m, 3, Ar$\underline{H}$), 2.16 (m, 2, Ar$\underline{H}$), and 1.60 (d, 1, J=5Hz,=C$\underline{H}$).

EXAMPLE 7

Trichloroethyl α-amino-diethylphosphonoacetate

A mixture of 2,4-dinitrophenyl hydrazine (1.875 g., 9.47 mMol) and p-toluenesulfonic acid monohydrate (1.800 g., 9.47 mMol) in ethanol (200 ml.) is stirred at room temperature for 45 minutes. To the resulting orange suspension is added trichloroethyl N-benzylidene-α-amino-diethylphosphonoacetate (3.881 g., 9.02 mMol) in a small volume of chloroform. The mixture is stirred for 30 minutes at room temperature, then filtered to remove benzaldehyde 2,4-dinitrophenyl hydrazone. The filtrate is evaporated in vacuo to an orange oil which is taken up in water (50 ml.) and washed with chloroform (4 × 25 ml.) to remove the remainder of the hydrazone. The aqueous phase (pH 2) is cooled in ice, adjusted to pH 10 with 2 N NaOH, saturated with NaCl, and extracted with methylene chloride (2 × 25 ml). The combined extracts are dried over MgSO$_4$ and evaporated in vacuo to give trichloroethyl α-amino-diethylphosphonoacetate as a pale yellow liquid.

The methyl ester, prepared in a similar manner from the methyl ester starting material, exhibits the following spectral characteristics: ir (CCl$_4$) 3400, 1747, 1256, 1164, 1055, 1031, and 969 cm$^{-1}$; nmr (CDCl$_3$)τ8.67 (t, 6, J=7 Hz, CH$_2$C$\underline{H}_3$), 8.17 (br s, 2, N$\underline{H}_2$), 6.20 (s, 3, C$\underline{H}_3$), 6.06 (d, 1, J=20 Hz, C$\underline{H}$), 5.82 (d of q, 4, J=8 Hz and J=7 Hz, C$\underline{H}_2$CH$_3$).

EXAMPLE 8

Trichloroethyl α-thioformamido-diethylphosphono-acetate

A solution of trichloroethyl α-amino-diethylphosphonoacetate (2.224 g, 6.5 mMol) in carbon tetrachloride (2.5 ml.) is added dropwise over 20 minutes to an ice-cold, stirring solution of ethyl thionoformate (0.640 g., 7.1 mMol) in carbon tetrachloride (1.0 ml.). The resulting solution is stirred an additional 2 hours at 0°C. then for 15 hours at room temperature. Evaporation of the solvent in vacuo leaves a yellow oil. The crude product is chromatographed on silica gel (50 g.) using 8:2 ethyl ether-acetone as eluting solvent to give trichloroethyl α-thioformamido-diethylphosphonoacetate as an oil.

The corresponding methyl ester is prepared in the same manner from methyl α-amino-diethylphosphonoacetate: ir (CCl$_4$) 3195, 1751, 1427, 1295, 1239, and 1031 cm$^{-1}$; nmr (CDCl$_3$)τ8.65 (splintered t, 6, J=7 Hz, CH$_2$C$\underline{H}_3$), 6.18 (s, 3, C$\underline{H}_3$), 5.80 (splintered p, 4, C$\underline{H}_2$CH$_3$), 3.96 (d of d, 1, J=22 Hz and J=8.5 Hz, C$\underline{H}$), 0.50 (d, 1, J=6 Hz, S=C$\underline{H}$), and 0.27 (br m, 1, N$\underline{H}$).

EXAMPLE 9

2-Oxo-propyl N-(trichloroethoxycarbonyl-diethylphosphonomethyl)-thioformimidate

A solution of chloro-2-propanone (0.470 q., 5.08 mMol) in acetone (4 ml.) is added dropwise during 15 minutes to a rapidly stirring mixture of trichloroethyl α-thioformamido-diethylphosphonoacetate (1.783 g., 4.62 mMol), K$_2$CO$_3$ (0.702 g., 5.08 mMol), and acetone (6 ml.). After having been stirred for 15 hours at room temperature, the mixture is diluted with methylene chloride (30 ml.) and filtered to remove salts. The filtrate is evaporated under reduced pressure to yield 2-oxo-propyl N-(trichloroethoxycarbonyl-diethylphosphonomethyl)-thioformimidate.

The corresponding methyl ester is prepared from methyl α-thioformamido-diethylphosphonoacetate in an analogous manner: ir (CCl$_4$) 1751, 1733, 1597, 1263, 1155, 1055, 1028, and 972 cm$^{-1}$; nmr (CDCl$_3$)τ8.67 (t, 6, J=7 Hz, CH$_2$C$\underline{H}_3$), 7.66 (s, 3, COC$\underline{H}_3$), 6.20 (s, 3, C$\underline{H}_3$), 6.16 (s, 2, COC$\underline{H}_2$), 5.83 (d of q, 4, J=8 Hz and J=7 Hz, C$\underline{H}_2$CH$_3$), 5.36 (d, 1, J=21 Hz, C$\underline{H}$), and 1.59 (d, 1, J=4Hz, =C$\underline{H}$).

EXAMPLE 10

Trichloroethyl dl-7α-azido-3-methyl-3-cephem-4-carboxylate

To an ice-cold, stirring solution of 2-oxo-propyl N-(trichloroethoxycarbonyl-diethylphosphonomethyl) thioformimidate (1.821 g., 4.43 mMol) and triethylamine (0.496 g., 4.9 mMol) in dry methylene chloride (25 ml.) is added dropwise over 2 hours azidoacetyl chloride (0.585 g., 4.9 mMol) in methylene chloride (15 ml.). The resulting solution is stirred under a nitrogen atmosphere for 1 more hour at 0°C., then washed with water (3 × 25 ml.) and saturated brine (25 ml.), and dried over MgSO$_4$. Evaporation of the solvent under reduced pressure leaves an oil which is chromatographed on silica gel (40 g.) using an ethyl acetate-benzene solvent gradient to afford trichloroethyl dl-7α-azido-3-methyl-3-cephem-4-carboxylate.

The corresponding methyl ester is prepared in an analogous manner from 2-oxo-propyl N-(methoxycarbonyldiethylphosphonomethyl)thioformimidate. ir (CCl$_4$) 2115, 1790, 1735, 1370, 1300, 1241, 1209, and 1125 cm$^{-1}$; nmr (CDCl$_3$) τ7.85 (s, 3, 3-C$\underline{H}_3$), 6.75, 6.48 (ABq, 2, J=17Hz, 2-C$\underline{H}_2$), 6.08 (s, 3, CO$_2$C$\underline{H}_3$), 5.45 (d,1, J=2Hz, H$_6$ or H$_7$), and 5.33 (d, 1 J=2Hz, H$_6$or H$_7$); mass spectrum m/e 254, 226 and 171.

EXAMPLE 11

Trichloroethyl dl-7α-amino-3-methyl-3-cephem-4-carboxylate

A mixture of 250 mg. of trichloroethyl dl-7α-azido-3-methyl-3-cephem-4-carboxylate, 250 mg. of platinum oxide and 15 ml. of benzene is hydrogenated at 40 psi for 4 hours. The catalyst is removed by filtration through diatomaceous earth and the solvent is evaporated under reduced pressure to give trichloroethyl dl-7α-amino-3-methyl-3-cephem-4-carboxylate as an oil.

The corresponding methyl ester is prepared in an analogous manner from methyl dl-7α-azido-3-methyl-3-cephem-4-carboxylate. ir (film) 5.69, 5.81, 7.34, 8.09 and 8.94μ; nmr (CDCl$_3$)τ8.12 (m, 2, N$\underline{H}_2$), 7.93 (s, 3, C$\underline{H}_3$), 6.86 and 6.56 (AB q, 2, J=18Hz, C$\underline{H}_2$), 6.15 (s, 3, CO$_2$C$\underline{H}_3$), 5.93 (d, 1, H$_6$ or H$_7$), and 5.58 (d, 1, H$_7$ or H$_6$).

EXAMPLE 12

Trichloroethyl dl-7-diazo-3-methyl-3-cephem-4-carboxylate

A mixture of 250 mg. of sodium nitrite, 200 mg. of trichloroethyl dl-7α-amino-3-methyl-3-cephem-4-carboxylate, 15 ml. of methylene chloride and 15 ml. of water/ice is shaken in a separatory funnel. p-Toluenesulfonic acid monohydrate (225 mg.) is added in three portions during 20 minutes. The separatory funnel is shaken vigorously during this period. The methylene chloride layer is separated, dried over sodium sulfate and evaporated under reduced pressure to give trichloroethyl dl-7-diazo-3-methyl-3-cephem-4-carboxylate.

The corresponding methyl ester is prepared in an analogous manner from methyl 7α-amino-3-methyl-3-cephem-4-carboxylate.

EXAMPLE 13

Diethyl N-benzylaminomethylphosphonate hydrochloride

A mixture of 288 g. of diethylphosphite and 248.2 g. of 1,3,5-tribenzyl-sym-hexahydrotriazine is stirred for 6 hours in an oil bath at 100°C.; a drying tube being used to protect the reaction mixture from moisture. After allowing the resulting reaction mixture to come to room temperature overnight, the mixture is dissolved in ethyl ether, placed in an ice bath and treated with 32 g. of HCl in 100 ml. of ether. The resulting solid is filtered off and the filtrate is treated with 56.7 g. of HCl in 200 ml. of ether, and the solution is filtered to remove the solid. The resulting filtrate is treated with 31.2 g. of HCl in ether, and the ether is evaporated to afford an oil. The solid obtained above is recrystallized from a mixture of tetrahydrofuran and ethyl ether; the ethyl ether being added to the tetrahydrofuran solution at room temperature. In this manner, 157 g. of crystalline product are obtained from the first solid and 191.8 g. from the second solid. The filtrates obtained from the two recrystallizations are combined and an additional 34.8 g. of solid obtained by the addition of more ether. The diethyl N-benzylaminomethylphosphonate hydrochloride so obtained is hygroscopic.

nmr ($D_2O$) τ: 2.4, s ($C_6\underline{H}_5$); 5.58, s ($C_6H_5C\underline{H}_2$); 5.68, m ($CH_3C\underline{H}_2O$); 6.4, d (NH—$C\underline{H}_2$—P); 8.8, t ($C\underline{H}_3$—$CH_2O$).

EXAMPLE 14

Diethyl aminomethylphosphonate hydrochloride

A solution of 148.4 g. of diethyl N-benzylaminomethylphosphonate hydrochloride is dissolved in 1500 ml. of ethanol and hydrogenated in the presence of 6.1 g. of palladium on charcoal at 40 psi for 6 hours. The resulting reaction mixture is filtered through diatomaceous earth and the filtrate evaporated. The resulting residue is treated with dry benzene and then dried in vacuo overnight to afford 102 g. of diethyl aminomethylphosphonate hydrochloride.

nmr ($CDCl_3$) τ: 2.7 ($NH^+$); 5.7, m ($CH_3$—$C\underline{H}_2O$—P); 6.43, d (NH—$C\underline{H}_2$—P); 8.61, t ($C\underline{H}_3CH_2$—O).

EXAMPLE 15

Diethyl N-benzylidene-aminomethylphosphonate

A solution of 15 g. of diethyl aminomethylphosphonate hydrochloride is dissolved in about 100 ml. of chloroform and cooled in an ice bath. Ammonia gas is bubbled through the solution for about 15 minutes with stirring. The ammonium chloride is filtered off and washed with chloroform and the combined filtrate and washings are dried over magnesium sulfate, filtered and evaporated to afford 12 g. of diethyl aminomethylphosphonate as a yellowish liquid.

The free amine is cooled in an ice bath and 7.8 ml. of benzaldehyde is added dropwise over 10 minutes followed by 10 ml. of absolute ethanol. The solution is stirred for 30 minutes at 0°C. and then diluted with 60 ml. of ethanol. The solvent is evaporated and the residue dried twice with benzene after which the solution is evaporated in vacuo to give 17.8 g. of diethyl N-benzylidene-aminomethylphosphonate as a light yellow liquid.

ir μ: 6.07 (C=N), 9.7 (P—O).

EXAMPLE 16 p-Methoxybenzyl N-benzylidene-α-amino-diethylphosphonoacetate

A solution of 15.8 g. of diethyl N-benzylideneaminomethylphosphonate in dry tetrahydrofuran is placed in a 500 ml. three-neck flask fitted with two dropping funnels, a nitrogen inlet and magnetic stirrer. The flask is placed in a dry ice-acetone bath at −78°C. and 27 ml. of 2.3 M phenyllithium solution (7:3 benzene-ether) is added dropwise over about 10 minutes. The solution is then stirred for 15 minutes and 24.8 ml. of p-methoxybenzylchloroformate is added dropwise over 45 minutes. After stirring for 20 minutes at −78°C., the cooling bath is removed and the solution added to come to room temperature. The solvent is removed in vacuo and the oily residue partitioned between 600 ml. of ethyl ether and 160 ml. of pH 3 phosphate buffer plus 160 ml. of water. The aqueous phase is separated and washed twice with ether. The combined ether extracts are washed with brine, dried over magnesium sulfate, filtered and evaporated to afford 30 g. of crude p-methoxybenzyl N-benzylidene-α-amino-diethylphosphonoacetate as a yellow liquid. The product so obtained is placed on a column of 400 g. of silica gel packed with 1:3 ethyl acetate-ether with a 600 ml. forerun. Two fractions of 50 ml. each followed by 26 fractions of 25 ml. each and then 50 ml. fractions are collected. Fractions 29–45 contain 6.845 g. of pure product.

ir ($CHCl_3$) μ: 5.75 (COOMe), 6.10 (C=N), 8–8.3 and 9.5–9.75 (P—O).

nmr ($CDCl_3$) τ: 8.74 (d of t, J=7Hz, J=2Hz, 6H), 6.23 (s, 3H), 5.83 (d of p, J=7Hz, J=2Hz, 4H), 5.24 (d, J=20Hz, 1H), 4.79 (s, 2H), 2–3.3 (aromatic multiplets, 9H), 1.63 (d, J=4.5Hz, 1H).

The pH 3 phosphate buffer used above is prepared by diluting 58 g. of 85% phosphoric acid to 500 ml. with water and adding 50% sodium hydroxide to pH 3.

The p-methoxybenzylchloroformate used in this example is prepared as follows: To a solution of 28 ml. of phosgene in 200 ml. of ethyl ether is added dropwise a solution of 27.6 g. of p-anisyl alcohol in 140 ml. of ether over a period of 1½ hours. The resulting mixture is evaporated under vacuum to 80 ml. The resulting p-methoxybenzylchloroformate solution has a concentration of 2.5 mmoles per ml.

EXAMPLE 17 p-Methoxybenzyl N-benzylidene-α-amino-diethylphosphonoacetate

The reaction is run under nitrogen atmosphere in a flame-dried 50 ml. three-neck round bottom flask fitted with a magnetic stirrer, a nitrogen inlet and septum. The flask is charged with a solution of 1.02 g. of diethyl N-benzylideneaminomethylphosphonate in 8 ml. of tetrahydrofuran and cooled in a dry ice-acetone bath.

Phenyllithium (2.0 ml. of a 2.0 M solution in 7:3 benzene-ether) is added and the burgundy solution is stirred for 15 minutes at −78°C. To the solution is then added dropwise over a 15-minute period 0.80 ml. of 2.5 M solution of p-methoxybenzylchloroformate in ether, and the resulting solution is stirred for 15 minutes at −78° C. The phenyllithium p-methoxybenzylchloroformate treatment is repeated twice more, each time decreasing the amounts by half. After the final addition of the p-methoxybenzylchloroformate, the reaction mixture is allowed to warm to room temperature over a period of one hour. The solvents are then evaporated in vacuo to afford a gold foam which is partitioned between 50 ml. of ether and 0.5 M pH 3 phosphate buffer (40 ml.). The aqueous phase is separated and extracted with 25 ml. of ether. The combined ether phases are washed with saturated brine (25 ml.), dried over magnesium sulfate and evaporated under reduced pressure to afford 1.71 g. of a gold oil. Chromatography of the crude product on silica gel (25 g.) using 9:1 ether-ethyl acetate as eluting solvent affords the title product as a yellow oil in 39% yield.

EXAMPLE 18 p-Methoxybenzyl α-amino-diethylphosphonoacetate

A solution of 16.4 g. of p-methoxybenzyl N-benzylidene-α-amino-diethylphosphonoacetate in 100 ml. of ether is added over 30 minutes with stirring to a solution of 8.25 g. of p-toluenesulfonic acid monohydrate in 150 ml. of ether. To the reaction mixture is added 60 ml. of cyclohexane and the solvent layer is separated by decantation. The residue is washed with additional 2:1 ether-cyclohexane and is again decanted. The resulting oil is dissolved in about 25 ml. of 1 M dipotassium phosphate (final pH about 7), and this solution is extracted 4 times with methylene chloride. The methylene chloride solution is then dried with magnesium sulfate, filtered and evaporated to give 12 g. of p-methoxybenzyl α-amino-diethylaminophosphonoacetate as an orange oily product. ir (neat) $\mu$: 2.95 (NH), 5.75 (C=O), and 9.75 (P—O); nmr (CDCl$_3$) $\tau$: 8.73 (t, 6, J=7Hz, CH$_2$CH$_3$), 8.12 (s, 2, NH$_2$), 6.18 (s, 3, ArOCH$_3$), 6.03 (d, 1, J=21Hz, CH), 5.86 (p, 4, J=7Hz, CH$_2$CH$_3$), 4.80 (s, 2, ArCH$_2$), 3.11 (d, 2, J=8Hz, arH), and 2.64 (d, 2, J=8Hz, ArH).

EXAMPLE 19 p-Methoxybenzyl α-thioformamido-diethylphosphonoacetate p-Methoxybenzyl α-amino-diethylphosphonoacetate (0.11 g.) is dissolved in methylene chloride and placed in a sealable thick-walled tube. The methylene chloride is removed by blowing with nitrogen. Ethylthionoformate (0.1 ml.) is added to the tube and with nitrogen passing into the tube it is placed in a dry ice-acetone bath. Hydrogen sulfide is condensed in the tube to give about 0.1 ml. The seal is then placed on the tube, and it is removed from the ice bath. After about one-half hour, the tube is shaken to mix the contents and then allowed to stand overnight. The tube is cooled in a dry ice-acetone bath and the seal removed. The resulting reaction mixture is allowed to slowly come to room temperature, nitrogen being bubbled in to remove the final traces of hydrogen sulfide. The residue is dissolved in methylene chloride and filtered. The resulting solution is evaporated to afford 0.166 g. of crude p-methoxybenzyl α-thioformamido-diethylphosphonoacetate.

A larger preparation comprising 4 g. of crude material is placed on a column of 60 g. of silica gel and eluted with ethyl acetate. 10 Ml. fractions are taken following a forerun of about 100 ml. Fractions 10–22 contain 2.8 g. of product. ir (CCl$_4$) $\mu$: 3.14, 5.72, 6.61, 7.00, 8.01 and 9.65; nmr (CDCl$_3$) $\tau$: 8.78 (t, 3, J=7Hz, CH$_2$CH$_3$), 8.73 (t, 3, J=7Hz, CH$_2$CH$_3$), 6.20 (s, 3, ArOCH$_3$), 5.88 (m, 4, CH$_2$CH$_3$), 4.81 (s, 2, ArCH$_2$), 3.96 (d of d, 1, J=8.5 and J=22Hz, CH), 3.11 (d, 2, J=9Hz, ArH), 2.66 (d, 2, J=9Hz, ArH), and 0.55 (d, 1, J=5Hz, HCS).

EXAMPLE 20

2-Oxo-propyl N-(p-methoxybenzyloxycarbonyl-diethylphosphonomethyl)thioformimidate A solution of p-methoxybenzyl α-thioformamidodiethylphosphonoacetate (58 mg., 0.155 mmole) in acetone (0.5 ml.) is treated successively with potassium carbonate (23 mg., 0.166 mmole) and chloro-2-propanone (13.5 $\mu$l., 0.168 mmole). The resulting mixture is stirred in a capped flask at room temperature for 14.5 hours, then diluted with dry methylene chloride (2 ml.) and filtered. Evaporation of the filtrate under reduced pressure gives 2-oxo-propyl N-(p-methoxybenzyloxycarbonyl)-diethylphosphonomethyl)thioformimidate (60 mg.) as an oil. ir (CCl$_4$) $\mu$: 5.75, 6.20, 6.28, 6.62, 8.00, 8.50, 8.68, 9.71 and 10.24. nmr (CDCl$_3$) $\tau$: 8.73 (t, 6, J=7Hz, CH$_2$CH$_3$), 7.73 (s, 3, COCH$_3$), 6.20 (s, 5, OCH$_3$ and OCH$_2$), 5.90 (d of d, 4, J=7Hz and J=7.5Hz, CH$_2$CH$_3$), 5.35 (d, 1, J−21Hz, CH), 4.83 (s, 2, CH$_2$Ar), 3.14 (d, 2, J=9Hz, ArH), 2.66 (d, 2, J=9Hz, ArH), and 1.60 (d, 1, J=4Hz, —N=CH—).

EXAMPLE 21 p-Methoxybenzyl 5-methyl-6H-1,3-thiazine-4-carboxylate and methyl 5-methyl-6H-1,3-thiazine-4-carboxylate p-Methoxybenzyl 5-methyl-6H-1,3-thiazine-4-carboxylate A. A solution of 2-oxo-propyl N-(p-methoxybenzyloxycarbonyl-diethylphosphonomethyl)thioformimidate (59 mg.) in acetone (0.5 ml.) is stirred with powdered potassium carbonate (25 mg.) for 21 hours at room temperature and under a nitrogen atmosphere. The resulting mixture is diluted with methylene chloride and filtered. Evaporation of the filtrate in vacuo yields an oil which is dissolved in carbon tetrachloride (4 ml.), washed with water (2 × 2 ml.) and saturated brine (4 ml.), dried over magnesium sulfate, and evaporated in vacuo to yield p-methoxybenzyl 5-methyl-6H-1,3-thiazine-4-carboxylate (35 mg.) as a yellow oil. ir (CCl$_4$) $\mu$: 5.81, 6.20, 6.61, 7.68, 8.03, 8.49, 9.38 and 9.58. nmr (CDCl$_3$) $\tau$: 7.80 (s, 3, CH$_3$), 6.73 (splintered s, 2, CH$_2$), 6.18 (s, 3, OCH$_3$), 4.73 (s, 2, ArCH$_2$), 3.10 (d, 2, J=9Hz, ArH). 2.93 (d, 2, J=9Hz, ArH), and 1.72 (s, 1, —N=CH—).

B. A mixture of p-methoxybenzyl α-thioformamidodiethylphosphonoacetate (188 mg., 0.5 mmole), powdered potassium carbonate (1.52 mg., 1.1 mmole) and chloro-2-propanone (44$\mu$l., 0.55 mmole) in acetone (2.5 ml.) is stirred at room temperature and under a nitrogen atmosphere. After 22 hours stirring, the mixture is filtered and the salts washed with acetone. The combined filtrate and washings are evaporated in vacuo to a dark residue which is shaken with csrbon tetrachloride (3 × 2 ml.). The combined extracts are washed with water (2 × 2 ml.) and saturated brine (2 ml.), dried over magnesium sulfate and evaporated in vacuo to give p-methoxybenzyl 5-methyl-6H-1,3-thiazine-4-carboxylate (116 mg.) as an orange oil.

Methyl 5-methyl-6H-1,3-thiazine-4-carboxylate

By analogous procedures, methyl 5-methyl-6H-1,3-thiazine-4-carboxylate is prepared from either 2-oxopropyl N-(methoxycarbonyl-diethylphosphonomethyl)thioformimidate or methyl α-thioformamido-diethylphosphonoacetate.

ir (CCl$_4$) μ: 5.81, 6.39, 6.97, 7.66, 8.00 and 9.29.
nmr (CDCl$_3$) τ: 7.70 (s, 3, C$\underline{H}_3$), 6.63 (splintered s, 2, C$\underline{H}_2$), 6.10 (s, 3, CO$_2$C$\underline{H}_3$) and 1.60 (s, 1, —N=C$\underline{H}$—).

EXAMPLE 22 p-Methoxybenzyl
dl-7α-azido-3-methyl-decephalosporanate

A solution of p-methoxybenzyl 5-methyl-6H-1,3-thiazine-4-carboxylate (34 mg., 0.123 mmole) in dry methylene chloride (1 ml.) is stirred in an ice bath under a nitrogen atmosphere. Triethylamine (19 μl., 0.136 mmole) is added to the solution via syringe. A solution of azidoacetyl chloride (12 μl., 0.136 mmole) in dry methylene chloride (1 ml.) is then added dropwise over 30 minutes. The resulting solution is stirred in additional 1.5 hours at 0°C., then diluted with methylene chloride (4 ml.), washed with water (2× 2 ml.) and saturated brine (4 ml.), dried over magnesium sulfate, and evaporated in vacuo to give a yellow-brown oil (42 mg.). The crude product is purified by preparative thin layer chromatography on a 0.5 mm. silica gel GF plate. Development with 10% ethyl acetate in benzene gives a sharp UV visible band which affords p-methoxybenzyl dl-7α-azido-3-methyl-decephalosporanate (10 mg.) after ethyl ether extraction.

ir (CCl$_4$) μ: 4.74, 5.59, 5.80, 6.20, 6.61, 7.22, 7.34, 7.69, 8.01, 8.12, 8.29, 8.50, 8.91 and 9.59.
nmr (CDCl$_3$) τ: 7.92 (s, 3, C$\underline{H}_3$), 6.82, 6.55 (AB q, 2, J=18Hz, 2-C$\underline{H}_2$), 6.18 (s, 3, OC$\underline{H}_3$), 5.52 (d, 1, J=1.6Hz, 7H or 6H), 5.40 (d, 1, J=1.6Hz, 6H or 7H), 4.76 (s, 2, C$\underline{H}_2$Ar), 3.10 (d, 2, J=9Hz, Ar$\underline{H}$), and 2.61 (d, 2, J=9Hz, Ar$\underline{H}$).

The corresponding methyl ester is prepared in a similar manner from methyl 5-methyl-6H-1,3-thiazine-4-carboxylate.

Following the procedures described above, p-methoxybenzyl 5-methoxymethyl-6H-1,3-thiazine-4-carboxylate, 2,2,2-trichloroethyl 5-methyl-6H-1,3-thiazine-4-carboxylate or methoxymethyl 5-isobutyryloxymethyl-6H-1,3-thiazine-4-carboxylate are reacted with azido acetyl chloride to obtain p-methoxybenzyl dl-3-methoxymethyl-7α-azido-3-cephem-4-carboxylate, 2,2,2-trichloroethyl dl--3-methyl-7α-azido-3-cephem-4-carboxylate and methoxymethyl dl-3-isobutyryloxymethyl-7α-azido-3-cephem-4-carboxylate, respectively.

EXAMPLE 23 p-Methoxybenzyl
5-acetoxymethyl-6H-1,3-thiazine-4-carboxylate

To a stirring solution of p-methoxybenzyl α-thioformamido-diethylphosphonoacetate (114 mg., 0.3 mmole) in acetone (1.5 ml) is added powdered potassium carbonate (124 mg, 0.9 mmole). The resulting mixture is stirred for 5 minutes at room temperature and under a nitrogen atmosphere, then treated with a solution of 1-acetoxy-3-chloro-2-propanone (48 mg, 0.32 mmole) in acetone (0.5 ml). After having been sitrred for 3 hours at room temperature, the mixture is filtered to remove the salts which are washed with acetone. The combined filtrate and washings are evaporated in vacuo to a dark oil. The residue is dissolved in CCl$_4$ (6 ml), washed with aqueous phosphate (1 ml of 1M dipotassium phosphate + 2 ml water) and water (2 × 3 ml)., dried over magnesium sulfate, and evaporated in vacuo to give crude p-methoxybenzyl 5-acetoxymethyl-6H-1,3-thiazine-4-carboxylate (106 mg) as an orange oil.

ir (CCl$_4$) μ: 5.71, 5.82 (sh), 6.21, 6.61 7.67, 8.01, 8.17, 8.49 and 9.58.
nmr (CDCl$_3$) τ: 7.95 (s, 3, OCOC$\underline{H}_3$), 6.63 (s, 2, 5-C$\underline{H}_2$), 6.20 (s, 3, OC$\underline{H}_3$), 4.86 (s, 2, C$\underline{H}_2$), 4.75 (s, 2, C$\underline{H}_2$), 3.13 (d, 2, J=8Hz, Ar$\underline{H}$), 2.63 (d, J=8Hz, Ar$\underline{H}$) and 1.65 (s, 1, N=C$\underline{H}$—).

In an analogous manner, methyl α-thioformamidodiethylphosphonoacetate affords methyl 5-acetoxymethyl-6H-1,3-thiazine-4-carboxylate.

EXAMPLE 24 p-Methoxybenzyl dl-7α-azido-cephalosporanate

A solution of crude p-methoxybenzyl 5-acetoxymethyl-6H-1,3-thiazine-4-carboxylate (100 mg., 0.3 mmole) in dry methylene chloride (3 ml.) is stirred in an ice bath and under a nitrogen atmosphere. Triethylamine (56 μl., 0.4 mmole) is added via syringe followed by the dropwise addition of a solution of azido acetyl chloride (35 μl., 0.4 mmole) in dry methylene chloride (2 ml.) over a period of 90 minutes. The resulting solution is stirred an additional 60 minutes at 0°C., then diluted with methylene chloride (5 ml.) washed with water (2 × 5 ml.), dried over magnesium sulfate, and evaporated in vacuo to a dark oil (115 mg.). The oil is shaken with carbon tetrachloride (2 × 5 ml.) and the carbon tetrachloride solution is dried over magnesium sulfate and evaporated in vacuo to a yellow oil (110 mg.). Chromatography of the crude product on silica gel (3 g., packed under 5% ethyl acetate in benzene) using 5 % ethyl acetate in benzene as eluting solvent gives p-methoxybenzyl dl-7α-azido-cephalosporanate (13 mg.) as a clear oil.

ir (CCl$_4$) μ: 4.73, 5.58, 5.73, 6.20, 6.61, 7.20, 7.38, 8.15, 8.47, 8.92, and 9.57.
nmr (CDCl$_3$) τ: 7.97 (s, 3, OCOC$\underline{H}_3$), 6.65, 6.42 (AB q, 2, J=18Hz, 2-C$\underline{H}_2$), 6.13 (s, 3, OC$\underline{H}_3$), 5.45 (d, 1, J=1.8Hz, 7H or 6H), 5.38 (d, 1, J=1.8Hz, 6H or 7H), 5.20, 5.00 (AB q, 2, J=13Hz, C$\underline{H}_2$OAc), 3.08 (d, 2, J=9Hz, Ar$\underline{H}$) and 2.60 (d, 2, J=9Hz, Ar$\underline{H}$).

In an analogous procedure, methyl 5-acetoxymethyl-6H-1,3-thiazine-4-carboxylate gives methyl dl-7α-azido-cephalosporanate.

ir (CCl$_4$) μ: 4.74, 5.56, 5.72, 6.10, 6.96, 7.23, 8.14, 8.93 and 9.67.
nmr (CDCl$_3$) τ: 7.90 (s, 3, OCOC$\underline{H}_3$), 6.58, 6.32 (AB q, 2, J=18Hz, 2-C$\underline{H}_2$), 6.04 (s, 3, CO$_2$C$\underline{H}_3$), 5.30 (m, 2, 6H and 7H), and 5.13, 4.90 (AB q, 2, J=13Hz, C$\underline{H}_2$OAc).

EXAMPLE 25

Trichloroethyl
N-benzylidene-α-amino-diethylphosphonoacetate

A solution of diethyl N-benzylidene-aminomethylphosphonate (12.738 g., 50 mmole) in dry tetrahydrofuran (250 ml.) is stirred in a dry ice-acetone bath and under a nitrogen atmosphere. Phenyllithium (25 ml. of a 2.0 M solution in 7:3 benzene-ethyl ether) is added via syringe. The resulting burgundy solution is stirred for 30 minutes at −78°C., then treated dropwise over 45 minutes with a solution of 2,2,2-trichloroethyoxycarbonyl chloride (5.30 g., 25 mmole) in dry tetrahydrofuran (50 ml.). After stirring the mixture for an additional 2 hours at −78°C., the dry ice bath is replaced by an ice water bath and stirring is continued for 1 hour. Evaporation of the solvent in vacuo leaves a yellow foam which is partitioned between ethyl ether (250 ml.) and aqueous phosphate (50 ml. of 1M pH 3 phosphate + 50 ml. water). The aqueous portion is separated and extracted with ethyl ether (2 × 50 ml.). The combined ethereal solution is washed with saturated brine (100 ml.), dried over magnesium sulfate, and evaporated in vacuo to yield a cloudy, yellow oil (17.1 g.). The crude product is purified by chromatography on silica gel (430 g., packed under ethyl ether). Elution with ethyl ether affords trichloroethyl N-benzylidene-α-amino-diethylphosphonoacetate (7.058 g.) as a yellow oil.

ir (CCl$_4$) μ: 5.68, 6.10, 7.90, 8.73, 9.48, 9.70, and 10.22.

nmr (CDCl$_3$) τ: 8.65 (d of t, 6, J=7Hz and J=0.6Hz, CH$_2$CH$_3$), 5.72 (d of q, 4, J=8Hz, and J=7Hz, CH$_2$CH$_3$), 5.11 (d, 1, J=21Hz CH), 5.10 (s, 2, CH$_2$CCl$_3$), 2.50 (m, 3, ArH), 2.12 (m, 2, ArH), and 1.56 (d, 1, J=5Hz, —N=CH—).

EXAMPLE 26

Trichloroethyl α-amino-diethylphosphonoacetate

A. Trichloroethyl α-amino-diethylphosphonoacetate, p-toluenesulfonate

A solution of trichloroethyl N-benzylidene-α-amino-diethylphosphonoacetate (5.69 g., 13.2 mmole) in ethyl ether (25 ml.) is added to a rapidly stirring solution of p-toluenesulfonic acid monohydrate (2.76 g., 14.5 mmole) in ethyl ether (75 ml.). A white precipitate appears immediately. The mixture is stirred for 10 minutes at room temperature, then cooled in ice. The product is collected by suction filtration, washed with cold ethyl ether, and dried in vacuo to give trichloroethyl α-aminodiethylphosphonoacetate, p-toluenesulfonate (6.03 g.) as a white powder.

ir (Nujol) μ: 5.64, 7.86, 8.37, and 9.81.

nmr (DMSO-d$_6$) τ: 8.73 (t, 3, J=7Hz, CH$_2$CH$_3$), 8.70 (t, 3, J=7Hz, CH$_2$CH$_3$), 7.70 (s, 3, ArCH$_3$), 5.78 (two overlapping quintets, 4, J=7Hz, CH$_2$CH$_3$), 4.92 (s, 2, CH$_2$CCl$_3$), 4.85 (d, 1, J=21Hz, CH), 2.87 (d, 2, J=8Hz, ArH), and 2.46 (d, 2, J=8Hz, ArH).

B. Trichloroethyl α-amino-diethylphosphonoacetate

Trichloroethyl α-amino-diethylphosphonoacetate p-toluenesulfonate (1.03 g., 2 mmole) is partitioned between methylene chloride (20 ml.) and aqueous phosphate (4 ml. 1M dipotassium phosphate + 6 ml. water). The aqueous phase (pH 6.8) is separated and extracted with an additional portion of methylene chloride (10 ml.). The combined organic solution is washed with saturated brine (10 ml.), dried over magnesium sulfate, and evaporated in vacuo to give trichloroethyl α-amino-diethylphosphonoacetate (0.67 g.) as a pale yellow oil.

ir (CCl$_4$) μ: 5.67, 7.93, 8.65, 9.46, 9.70, and 10.24.

nmr (CDCl$_3$) τ: 8.65 (splintered t, 6, J=7Hz, CH$_2$CH$_3$), 8.08, (s, 2, NH$_2$), 5.92 (d, 1, J=22Hz, CH), 5.78 (m, 4, CH$_2$CH$_3$), and 5.15 (s, 2, CH$_2$CCl$_3$).

EXAMPLE 27 p-Methoxybenzyl dl-7α-amino-cephalosporanate

A mixture of p-methoxybenzyl dl-7α-azido-cephalosporanate (31 mg.), platinum oxide (25 mg.) and benzene (3ml.) is hydrogenated at 40 psi for 60 minutes. The catalyst is removed by filtration through diatomaceous earth, and the solvent is evaporated in vacuo to give p-methoxybenzyl dl-7α-amino-cephalosporanate (19 mg.) as a pale yellow oil.

ir (CHCl$_3$) 2.94, 5.62, 5.75, 6.20, 6.61, 7.16, 7.37, 8.02, 8.48, 8.94, 9.62, and 10.92μ;

nmr (CDCl$_3$) τ 8.18 (br s, 2, NH$_2$, 7.96 (s, 3, O=CCH$_3$), 6.70 and 6.46 (ABq, 2, J=19Hz, 2-CH$_2$), 6.18 (s, 3, ArOCH$_3$), 5.87 (d, 1, J=2Hz, H$_6$ or H$_7$), 5.57 (d, 1, J=2Hz, H$_7$ or H$_6$), 5.30 and 5.03 (ABq, 2, J=13Hz, CH$_2$OAc), 4.75 (splintered s, 2, ArCH$_2$), 3.11 (d, 2, J=9Hz, ArH), and 2.61 (d, 2, J=9Hz, ArH).

EXAMPLE 28

When other haloacetones are used in place of chloro-2-propanone, in accordance with the process set forth in Example 9, the corresponding S-substituted thioformimidate is obtained.

Representative of the substituted halo acetones that may be employed in the practice of the invention to afford the corresponding thioformimidate of the formula:

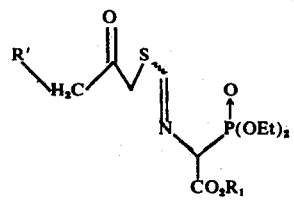

are the following:

wherein X = chloro and

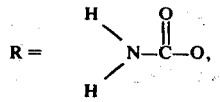

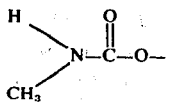

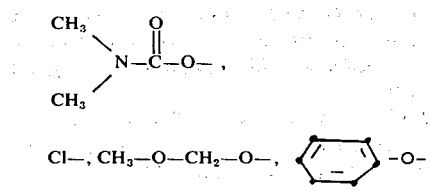

Other examples are:

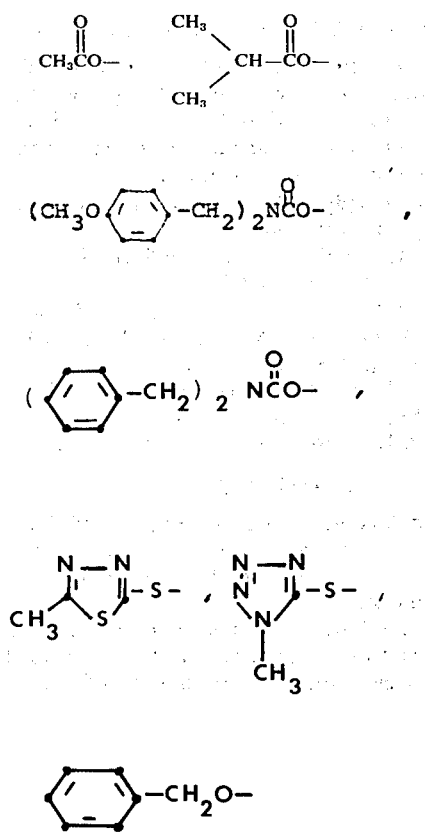

EXAMPLE 29

2-Azido-2-methoxyacetylchloride

A mixture of methyl 2-chloro-2-methoxyacetate (13.86 g., 0.1 mole), powdered sodium azide (8.46 g., 0.13 mole) and dry dimethoxyethane (80ml.) is stirred and heated at reflux for 39 hours. After cooling to room temperature, the mixture is filtered to remove salts which are washed with dry ether. Evaporation of the solvents at aspirator pressure leaves a yellow liquid which is distilled to give methyl 2-azido-2-methoxyacetate (10.5 g.) as a water-white liquid (b.p. 75°–77°C./17 mm.).

Aqueous sodium hydroxide (30 ml. of a 2.5 N solution) is added dropwise over 15 minutes to a stirring solution of methyl 2-azido-2-methoxyacetate (10.40 g., 72 mmole) in methanol (8.5 ml.). The mixture becomes warm and cloudy during the addition. The methanol is removed under reduced pressure and the aqueous residue is acidified to pH 1 with concentrated sulfuric acid and extracted with ether. The combined ethereal extracts are dried over sodium sulfate and evaporated in vacuo to leave 2-azido-2-methoxyacetic acid (8.82 g.) as a clear liquid.

A solution of 2-azido-2-methoxyacetic acid (4.2 g.) in thionyl chloride (10 ml.) is heated in an oil bath maintained at 80°C. for 20 minutes. After cooling to room temperature, the mixture is evaporated in vacuo to remove excess thionyl chloride and the residue is distilled to yield 2-azido-2-methoxyacetyl chloride (2.26 g.) as a water-white liquid (b.p. 64°–66°C./27 mm.).

EXAMPLE 30

Azidoacetyl trifluoromethylsulfonate

1. Silver oxide (4.65 g) is suspended in 20 ml acetonitrile and the mixture is cooled to 0°. To another 20 ml acetonitrile, cooled to 0°, is added 6.64 g of trifluoromethyl sulfonic acid dropwise and this solution is then added over 15 minutes to the suspension of Ag$_2$O in acetonitrile. After another 30 minutes, the slight excess of Ag$_2$O is filtered off. The filtrate is evaporated under reduced pressure. The residue is taken up in 20 ml C$_6$H$_6$ and evaporated under reduced pressure. The residue crystallizes on pumping and is dried under vacuum to give the silver trifluoromethyl sulfonate. 2. Silver trifluoromethylsulfonate (0.149 g) is dissolved in 5 ml CH$_2$Cl$_2$ and cooled to 0°. Azido-acetyl chloride (0.059 g) is then added and the mixture is stirred for 2 minutes. The silver chloride rapidly precipitates out. The reaction mixture containing azidoacetyl trifluoromethylsulfonate is cooled to −78° and maintained at that temperature until ready to use.

EXAMPLE 31

Azidoacetyl methane sulfonate

1. Isopropenyl axidoacetate

Azidoacetic acid (5.35 g, 0.05 mole) and mercuric acetate (1.82 g, 5.7 mMoles) are added to 50 ml of methylene chloride containing 0.1 ml of boron trifluoride etherate. Propyne, which had been passed through Linde Co. Molecular Sieves 4A, is bubbled slowly through the mixture for 3 hours. Sodium bicarbonate (0.5 g) is added and the mixture is filtered through a short Florisil column. The eluent is concentrated in vacuo and the residue obtained is purified by vacuum distillation to give isopropenyl azidoacetate.

2. Azidoacetyl methanesulfonate

Isopropenyl azidoacetate (1.41 g, 0.01 mole) and anhydrous methanesulfonic acid (0.96 g, 0.01 mole) in 15 ml of methylene chloride is allowed to stand at room temperature for three hours. The solvent is removed in vacuo to give azidoacetyl methanesulfonate.

EXAMPLE 31 A p-Methoxybenzyl d,1-7α-azido-deacetoxycephalosporanate

5-Methyl-4-(p-methoxybenzyloxycarbonyl)-6H-1,3-thiazine (0.028 g) is dissolved in 1 ml of CH$_2$Cl$_2$ and cooled to 0°. Triethylamine (0.016 ml) is added and the mixture is treated dropwise over 30 minutes with 1 ml of the solution of the azidoacetyl trifluoromethylsulfonate. The reaction mixture is stirred for 5 minutes, and then diluted with CH$_2$Cl$_2$, washed once with pH 7 buffer, dried, and evaporated to a residue which is purified by preparative tlc to give p-methoxybenzyl d,1-7α-azido-deacetoxycephalosporanate.

When azidoacetyl methanesulfonate is used in the above process in place of azidoacetyl trifluoromethylsulfonate, p-methoxybenzyl dl-7α-azidodeacetoxycephalosporanate is also obtained.

EXAMPLE 32

Diethyl N-benzylaminomethylphosphonate hydrochloride

A mixture of 288 g. of diethylphosphite and 248.2 g. of 1,3,5-tribenzyl-sym-hexahydrotriazine is stirred for 6 hours in an oil bath at 100°C.; a drying tube being used to protect the reaction mixture from moisture. After allowing the resulting reaction mixture to come to room temperature overnight, the mixture is dissolved in ethyl ether, placed in an ice bath and treated with 32 g. of HCl in 100 ml. of ether. The resulting solid is filtered off and the filtrate is treated with 56.7 g. of HCl in 200 ml. of ether, and the solution is filtered to remove the solid. The resulting filtrate is treated with 31.2 g. of HCl in ether, and the ether is evaporated to afford an oil. The solid obtained above is recrystallized from a mixture of tetrahydrofuran and ethyl ether; the ethyl ether being added to the tetrahydrofuran solution at room temperature. In this manner, 157 g. of crystalline product are obtained from the first solid and 191.8 g. from the second solid. The filtrates obtained from the two recrystallizations are combined and an additional 34.8 g. of solid obtained by the addition of more ether. The diethyl N-benzylaminomethylphosphonate hydrochloride so obtained is hygroscopic,

EXAMPLE 33

Diethyl aminomethylphosphonate hydrochloride

A solution of 148.4 g. of diethyl N-benzylaminomethylphosphonate hydrochloride is dissolved in 1500 ml. of ethanol and hydrogenated in the presence of 6.1 g. of palladium on charcoal at 40 psi for 6 hours. The resulting reaction mixtue is filtered through diatomaceous earth and the filtrate evaporated. The resulting residue is treated with dry benzene and then dried in vacuo overnight to afford 102 g. of diethyl aminomethylphosphonate hydrochloride.

EXAMPLE 34

Diethyl aminomethylphosphonate

A solution of 15 g. of diethyl aminomethylphosphonate hydrochloride is dissolved in about 100 ml. of chloroform and cooled in an ice bath. Ammonia gas is bubbled through the solution for about 15 minutes with stirring. The ammonium chloride is filtered off and washed with chloroform and the combined filtrate and washings are dried over magnesium sulfate, filtered and evaporated to afford 12 g. of diethyl aminomethylphosphonate as a yellowish liquid.

EXAMPLE 35

Diethyl N-benzylidene-aminomethylphosphonate

Diethyl aminomethylphosphonate (12.0 g) is cooled in an ice bath and 7.8 ml. of benzaldehyde is added dropwise over 10 minutes followed by 10 ml. of absolute ethanol. The solution is stirred for 30 minutes at 0°C. and then diluted with 60 ml. of ethanol. The solvent is evaporated and the residue dried twice with benzene after which the solution is evaporated in vacuo to give 17.8 g. of diethyl N-benzylideneaminomethylphosphonate as a light yellow liquid.

EXAMPLE 36 p-Methoxybenzyl N-benzylidene-α-aminodiethylphosphonoacetate and

The reaction is run under nitrogen atmosphere in a flame-dried 50 ml. three-neck round bottom flask fitted with a magnetic stirrer, a nitrogen inlet and septum. The flask is charged with a solution of 1.02 g. of diethyl N-benzylidene-aminomethylphosphonate in 8 ml. of tetrahydrofuran and cooled in a dry ice-acetone bath. Phenyllithium (2.0 ml. of a 2.0 M solution in 7.3 benzene-ether) is added and the burgundy solution is stirred for 15 minutes at −78°C. To the solution is then added dropwise over a 15-minute period 0.80 ml. of 2.5 M solution of p-methoxybenzylchloroformate in ether, and the resulting solution is stirred for 15 minutes at −78°C. The phenyllithium p-methoxybenzylchloroformate treatment is repeated twice more, each time decreasing the amounts by half. After the final addition of the p-methoxybenzylchloroformate, the reaction mixture is allowed to warm to room temperature over a period of one hour. The solvents are then evaporated in vacuo to afford a gold foam which is partitioned between 50 ml. of ether and 0.5 M pH 3 phosphate buffer (40 ml.). The aqueous phase is separated and extracted with 25 ml. of ether. The combined ether phases are washed with saturated brine (25 ml.), dried over magnesium sulfate and evaporated under reduced pressure to afford 1.71 g. of a gold oil. Chromatography of the crude product on silica gel (25 g.) using 9:1 ether-ethyl acetate as eluting solvent affords p-methoxybenzyl N-benzylidene-α-amino-diethylphosphonoacetate as a yellow oil in 39% yield.

EXAMPLE 37 p-Methoxybenzyl α-amino-diethylphosphonoacetate

A solution of 16.4 g. of p-methoxybenzyl N-benzylidene-α-amino-diethylphosphonoacetate in 100 ml. of ether is added over 30 minutes with stirring to a solution of 8.25 g. of p-toluenesulfonic acid in 150 ml. of ether. To the reaction mixture is added 60 ml. of cyclohexane and the solvent layer is separated by decantation. The residue is washed with additional 2:1 ether-cyclohexane and is again decanted. The resulting oil is dissolved in about 25 ml. of 1 M dipotassium phosphate (final pH about 7), and this solution is extracted 4 times with methylene chloride. The methylene chloride solution is then dried with magnesium sulfate, filtered and evaporated to give 12 g. of p-methoxybenzyl α-amino-diethylphosphonoacetate as an orange oily product.

EXAMPLE 38 p-Methoxybenzyl α-thioformamido-diethylphosphonoacetate p-Methoxybenzyl α-amino-diethylphosphonoacetate (0.11 g.) is dissolved in methylene chloride and placed in a sealable thick-walled tube. The methylene chloride is removed by blowing with nitrogen. Ethylthionoformate (0.1 ml.) is added to the tube and with nitrogen passing into the tube it is placed in a dry ice-acetone bath. Hydrogen sulfide is condensed in the tube to give about 0.1 ml. The seal is then placed on the tube, and it is removed from the ice bath. After about one-half hour, the tube is shaken to mix the contents and then allowed to stand overnight. The tube is cooled in a dry ice-acetone bath and the seal removed. The resulting reaction mixture is allowed to slowly come to room temperature, nitrogen being bubbled in to remove the final traces of hydrogen sulfide. The residue is dissolved in methylene chloride and filtered. The resulting solution is evaporated to afford 0.166 g. of crude p-methoxybenzyl α-thioformamidodiethylphosphonoacetate.

A larger preparation comprising 4 g. of crude material is placed on a column of 60 g. of silica gel and eluted with ethyl acetate. 10 Ml. fractions are taken following a forerun of about 100 ml. Fractions 10-22 contain 2.8 g. of product.

EXAMPLE 39 p-Methoxybenzyl 5-acetoxymethyl-6H-1,3-thiazine-4-carboxylate

To a stirring solution of p-methoxybenzyl α-thioformamido-diethylphosphonoacetate (114 mg., 0.3 mmole) in acetone (1.5 ml.) is added powdered potassium carbonate (124 mg., 0.9 mmole). The resulting mixture is stirred for 5 minutes at room temperature and under a nitrogen atmosphere, then treated with a solution of 1-acetoxy-3-chloro-2-propanone (48 mg., 0.32 mmole) in acetone (0.5 ml.). After having been stirred for 3 hours at room temperature, the mixture is filtered to remove the salts which are washed with acetone. The combined filtrate and washings are evaporated in vacuo to a dark oil. The residue is dissolved in carbon tetrachloride (6 ml.), washed with aqueous phosphate (1 ml. of 1M dipotassium phosphate + 2 ml. water) and water (2 × 3 ml.), dried over magnesium sulfate, and evaporated in vacuo to give crude p-methoxybenzyl 5-acetoxymethyl-6H-1,3-thiazine-4-carboxylate (106 mg.) as an organic oil.

EXAMPLE 40 p-Methoxybenzyl dl-7β-azido-7-methoxycephalosporanate and p-methoxybenzyl dl-7α-azido-7-methoxycephalosporanate To a solution of p-methoxybenzyl 5-acetoxymethyl-6H-1,3-thiazine-4-carboxylate (241 mg., 0.72 mmole) in dry methylene chloride (5 ml.) is added all at once a solution of triethylamine (110 μl., 0.79 mmole) in methylene chloride (1 ml.). The resulting mixture is stirred under a nitrogen atmosphere with ice-bath cooling while a solution of 2-azido-2-methoxyacetyl chloride (119 mg., 0.8 mmole) in dry methylene chloride (3 ml.) is added dropwise over a period of 50 minutes. After stirring an additional 1 hour at 0°C. and 2 hours at room temperature, the reaction mixture is diluted with methylene chloride (10 ml.), washed with water (2 × 5 ml.) and saturated brine (10 ml.), dried over magnesium sulfate, and evaporated in vacuo to give a yellow oil. Chromatography of the crude product on silica gel (9.0 g.) using 10 % ethyl acetate in benzene as eluting solvent affords p-methoxybenzyl dl-7β-azido-7-methoxycephalosporanate and p-methoxybenzyl dl-7α-azido-7-methoxycephalosporanate.

In an analogous procedure, methyl 5-methyl-6H-1,3-thiazine-4-carboxylate affords methyl dl-7β-azido-7-methoxy-3-methyl-decephalosporanate and methyl dl-7α-azido-7-methoxy-3-methyl-decephalosporanate in a 3:1 ratio. ir (CCl$_4$) of 7β-azido isomer 4.73, 5.60, 5.78, 6.97, 7.30, 8.05, 8.79 and 9.42μ; nmr (CDCl$_3$) of 7β-azido isomer τ 7.80 (s, 3, CH$_3$), 6.76 (s, 2, CH$_2$), 6.33 (s, 3, OCH$_3$), 6.13 (s, 3, CO$_2$CH$_3$) and 5.12 (s, 1, 6H). In addition to signals at τ 7.80, 6.76 and 6.13, the nmr spectrum of the 7α-azido isomer shows absorptions at τ6.30 (OCH$_3$) and 5.20 (6H).

EXAMPLE 41

Following the procedures described in Example 40 p-methoxybenzyl 5-methoxymethyl-6H-1,3-thiazine-4-carboxylate, 2,2,2-trichloroethyl 5-methyl-6H-1,3-thiazine-4-carboxylate or methoxymethyl 5-isobutyryloxymethyl-6H-1,3-thiazine-4-carboxylate are reacted with 2-azido-2-methoxyacetyl chloride to obtain p-methoxybenzyl dl-3-methoxymethyl-7β-azido-7α-methoxy-3-cephem-4-carboxylate, 2,2,2-trichloroethyl dl-3-methyl-7β-azido-7α-methoxy-3-cephem-4-carboxylate and methoxymethyl dl-3-isobutyryloxymethyl-7β-azido-7α-methoxy-3-cephem-4-carboxylate, respectively.

EXAMPLE 42 d,1-7β-Azido-7-methoxycephalosporanic acid p-Methoxybenzyl d,1-7β-azido-7-methoxycephalosporanate (250 mg) is treated with anisole (1.0 ml) and trifluoroacetic acid (5.0 ml) with ice-bath cooling. The resulting mixture is kept at 0° for 1 minute, and then evaporated in vacuo to remove trifluoroacetic acid. The residue is taken up in dilute aqueous sodium bicarbonate and extracted twice with ethyl ether. The aqueous portion is layered with ethyl acetate and acidified to pH 2.5 with 6 N hydrochloric acid. The ethyl acetate layer is separated, dried with magnesium sulfate, filtered, and evaporated in vacuo to give d,1-7β-azido-7-methoxycephalosporanic acid.

EXAMPLE 43 d,1-7β-Amino-7-methoxycephalosporanic acid

A mixture of d,1-7β-azido-7-methoxycephalosporanic acid (190 mg), dioxane (20 ml), and platinum oxide (200 mg) is hydrogenated at 40 psi for 2 hours. The catalyst is then removed by filtration through diatomaceous earth which is washed with water. The filtrate and washings are evaporated in vacuo to dryness, affording d,1-7β-amino-7-methoxycephalosporanic acid.

EXAMPLE 44

2,2,2-Trichloroethyl α-thioformamido-diethylphosphonoacetate 2,2,2-Trichloroethyl α-amino-diethylphosphonoacetate (6.85 g) and ethyl thionoformate (6 ml.) are placed in a sealable thick-walled tube. The tube is flushed with nitrogen and cooled in a dry-ice bath. Hydrogen sulfide (6 ml.) is condensed in the tube. The tube is sealed, shaken to mix its contents, and kept at room temperature overnight. The tube is cooled in dry-ice and the seal removed. A boiling chip is placed in the solution and it is allowed to slowly come to room temperature. Last traces of hydrogen sulfide are removed under a stream of nitrogen. The residue is taken up in chloroform, filtered and evaporated in vacuo to an oil. This material is chromatographed on silica gel yielding 2,2,2-trichloroethyl α-thioformamido-diethylphosphonoacetate.

EXAMPLE 45

2,2,2-Trichloroethyl 5-methoxymethyloxymethyl-6H-1,3-thiazine-4-carboxylate

A solution of 2,2,2-trichloroethyl α-thioformamidodiethylphosphonoacetate (3.87 g.) in acetone (50 ml.) is treated with powdered potassium carbonate (4.15 g) and 1-chloro-3-methoxymethyloxy-propan-2-one (1.60 g.). The mixture is stirred for 4 hrs. at room temperature under a nitrogen atmosphere, then filtered. Evaporation of the filtrate leaves a residue which is dissolved in methylene chloride. The solution is washed with dilute aqueous dipotassium hydrogen phosphate and water, dried over magnesium sulfate, filtered and evaporated in vacuo affording 2,2,2-trichloroethyl 5-methoxymethyloxymethyl-6H-1,3-thiazine-4-carboxylate.

The above thiazine is also obtained by a two step sequence. Thus, reaction of 2,2,2-trichloroethyl α-thioformamido-diethylphosphonoacetate with 1-chloro-3-methoxymethyloxy-propan-2-one in the presence of one equivalent of potassium carbonate affords 3-methoxymethyloxy-2-oxo-propyl N-(2,2,2-trichloroethyloxycarbonyl-diethylphosphonomethyl)thioformimidate. This material is cyclized to the thiazine utilizing potassium carbonate in acetone. Alternatively sodium hydride in dimethoxyethane may be employed as the cyclizing agent.

EXAMPLE 46

1-Chloro-3-methoxymethyloxy-propan-2-one is prepared from methyl glycolate as described below

STEP 1. Methyl methoxymethyloxyacetate

A solution of methyl glycolate (18.02 g) and triethylamine (20.24 g) in anhydrous methylene chloride (100 ml.) is added dropwise over 40 minutes to an ice-cold, stirring solution of chloromethyl methyl ether (17.7 g) in methylene chloride (200 ml.). The resulting mixture is allowed to stand overnight in a flask protected from moisture by a drying tube. The mixture is washed with water, 5% aqueous sodium bicarbonate, water, and brine, dried over sodium sulfate, filtered, and concentrated under reduced pressure. Distillation of the residue yields methyl methoxymethyloxyacetate.

STEP 2. Methoxymethyloxyacetyl chloride

Methyl methoxymethyloxyacetate (19.06 g) in methanol (20 ml.) is treated with aqueous sodium hydroxide (57 ml. of a 2.5 N solution) over a period of 30 minutes. The methanol is evaporated under reduced pressure and the aqueous residue lyophilized giving sodium methoxymethyloxyacetate. The sodium salt is dispersed in benzene (250 ml.) and treated with pyridine (1 ml.). Oxalyl chloride (30 ml.) is added with ice-bath cooling. The resulting mixture is stirred in the cold until gas evolution ceases, then at room temperature for 5 minutes. The mixture is filtered and evaporated under reduced pressure to remove excess oxalyl chloride and benzene. Distillation of the residue gives methoxymethyloxyacetyl chloride.

STEP 3. 1-Chloro-3-methoxymethyloxy-propan-2-one

A solution of methoxymethyloxy acetyl chloride (13.86 g) in anhydrous ether (50 ml.) is added dropwise to an ice-cold, stirring solution of diazomethane (4.2 g) and triethylamine (10.1 g) in ether (200 ml.). The mixture is kept an additional 5 hours in the cold, then filtered through a pad of magnesium sulfate. The ethereal filtrate of diazoketone is cooled in an ice bath. Anhydrous hydrogen chloride is bubbled through the solution until nitrogen evolution ceases. The resulting solution is washed with ice-cold water, dried over magnesium sulfate, and concentrated under reduced pressure. Distillation of the residue at reduced pressure affords 1-chloro-3-methoxymethyloxy-propan-2-one.

EXAMPLE 47

2,2,2-Trichloroethyl d,1-7α-azido-3-methoxymethyloxymethyl-3-cephem-4-carboxylate A solution of 2,2,2-trichloroethyl 5-methoxymethyloxymethyl-6H-1,3-thiazine-4-carboxylate (4.33 g) and triethylamine (1.38 g) in anhydrous methylene chloride (100 ml) is stirred at 0° under nitrogen. Azidoacetyl chloride (1.63 g) in methylene chloride (50 ml.) is added dropwise over a period of 2 hours. After having been stirred an additional 1 hour in the cold, the reaction mixture is washed with water and brine, dried with magnesium sulfate, filtered, and evaporated to an oil. This material is chromatographed on silica gel to yield 2,2,2-trichloroethyl d,1-7α-azido-3-methoxymethyloxymethyl-3-cephem-4-carboxylate.

EXAMPLE 48

2,2,2-Trichloroethyl d,1-7α-amino-3-methoxymethyloxymethyl-3-cephem-4-carboxylate 2,2,2-Trichloroethyl d,1-7α-azido-3-methoxymethyloxymethyl-3-cephem-4-carboxylate (1.63 g) is hydrogenated at 40 psi in benzene (80 ml.) with platinum oxide (0.8 g) for 1 hour. The mixture is filtered and evaporated, leaving an oil, which is 2,2,2-trichloroethyl d,1-7α-amino-3-methoxymethyloxymethyl-3-cephem-4-carboxylate.

EXAMPLE 49

2,2,2-Trichloroethyl d,1-7α-benzylideneamino-3-methoxymethyloxymethyl-b 3-cephem-4-carboxylate A mixture of 2,2,2-trichloroethyl d,1-7α-amino-3-methoxymethyloxymethyl-3-cephem-4-carboxylate (1.8 g), benzaldehyde (0.37 g), and magnesium sulfate (7.50 g) in methylene chloride (75 ml) is stirred at room temperatue for 96 hours. The mixture is filtered and the filtrate is evaporated in vcuo to an oil. This material is triturated with five portions of petroleum ether, diluted with benzene, and evaporated to give 2,2,2-trichloroethyl d,1-7α-benzylideneamino-3-methoxymethyloxymethyl-3-cephem-4-carboxylate.

EXAMPLE 50

2,2,2-Trichloroethyl d,1-7β-benzylideneamino-3-methoxymethyloxymethyl-3-cephem-4-carboxylate A solution of 2,2,2-trichloroethyl d,1-7α-benzylideneamino-3-methoxymethyloxymethyl-3-cephem-4-carboxylate (494 mg) in anhydrous tetrahydrofuran (15 ml) is purged with nitrogen and cooled in a dry ice-acetone bath. Phenyllithium (435 μl of a 2.3 M solution in 7:3 benzene-ether) is added, giving the anion. Dimethyl formamide (19 ml) is then added dropwise over a period of 10 minutes. The reaction is quenched by addition of a solution of water (0.18 ml) and acetic acid (0.14 ml) in tetrahydrofuran (10 ml). After warming to room temperature, the reaction mixture is diluted with benzene and washed six times with water. The second wash is acidified with pH 3 phosphate buffer and the fifth basified with pH 9 phosphate buffer. The benzene solution is dried with magnesium sulfate, filtered, and evaporated in vacuo leaving a mixture of 2,2,2-trichloroethyl d,1-7α-benzylideneamino-3-methoxymethyloxymethyl-3-cephem-4-carboxylate and 2,2,2-trichloroethyl d,1-7β-benzylideneamino-3-methoxymethyloxymethyl-3-cephem-4-carboxylate.

EXAMPLE 51

2,2,2-Trichloroethyl d,1-7β-amino-3-methoxymethyloxymethyl-3-cephem-4-carboxylate 2,4-Dinitrophenyl hydrazine (172 mg) is added to a stirring solution of p-toluenesulfonic acid monohydrate (166 mg) in absolute ethanol (25 ml). After having been stirred at room temperature for 45 minutes, the reaction mixture is treated with 2,2,2-trichloroethyl d,1-7-benzylideneamino-3-methoxymethyloxymethyl-3-cephem-4-carboxylate (430 mg., mixture of 7α- and 7β-isomers) in a small volume of chloroform (3 ml). The mixture is stirred at room temperature for 10 minutes, filtered, and the filtrate is evaporated in vacuo. The residue is treated with 1 M dipotassium hydrogen phosphate (2 ml) and water (15 ml) and extracted with ether (3 × 20 ml). The ethereal solution is dried with magnesium sulfate, filtered, and evaporated in vacuo to yield a mixture of 2,2,2-trichloroethyl d,1-7α-amino-3-methoxymethyloxymethyl-3-cephem-4-carboxylate and 2,2,2-trichloroethyl d,1-7β-amino-3-methoxymethyloxymethyl-3-cephem-4-carboxylate.

EXAMPLE 52

2,2,2-Trichloroethyl d,1-7α-(D-α-azido-phenylacetamido)-3-methoxymethyloxymethyl-3-cephem-4-carboxylate ad 2,2,2-trichloroethyl d,1-7β-(D-α-azido-phenylacetamido)-3-methoxymethyloxymethyl-3-cephem-4-carboxylate To an ice-cold, stirring solution of 2,2,2trichloroethyl d,1-7-amino-3-methoxymethyloxymethyl-3-cephem-4-carboxylate (325 mg., mixture of 7α- and 7β-isomers) in anhydrous methylene chloride (10 ml) is added successively pyridine (0.3 ml) and D-α-azido-phenylacetyl chloride (157 mg). After having been stirred at 0° for 15 minutes, the reaction mixture is diluted with more methylene chloride and washed with water, 1% aqueous phosphoric acid, 5% aqueous sodium bicarbonate, and water. The organic phase is dried over magnesium sulfate, filtered, and evaporated under reduced pressure. The residue is chromatographed on silica gel to yield 2,2,2-trichloroethyl d,1-7β-(D-α-azido-phenylacetamido)-3-methoxymethyloxymethyl-3-cephem-4-carboxylate and the corresponding 7α-isomer.

EXAMPLE 53

2,2,2-Trichloroethyl d,1-7β-(D-α-azido-phenylacetamido)-3-hydroxymethyl-3-cephem-4-carboxylate 2,2,2-Trichloroethyl d,1-7β-(D-α-azido-phenylacetamido)-3-methoxymethyloxymethyl-3-cephem-4-carboxylate (120 mg) is dissolved in dioxane (4 ml). The solution is diluted with water (1 ml) and treated with a small drop of 1 N perchloric acid. After being kept at room temperature for 2 hours, the reaction mixture is diluted with ethyl acetate and washed with water containing pH 9 phosphate buffer. The organic phase is separated, dried over magnesium sulfate, filtered, and evaporated to yield 2,2,2-trichloroethyl d,1-7β-(D-α-azido-phenylacetamide)-3-hydroxymethyl-3-cephem-4-carboxylate.

EXAMPLE 54

2,2,2-Trichloroethyl d,1-7β-(D-α-amino-phenylacetamide)-3-(N-2,2,2-trichloroethyl)carbamoyloxymethyl-3-cephem-4-carboxylate A solution of 2,2,2-trichloroethyl d,1-7β-(D-α-amino-phenylacetamido)-3-hydroxymethyl-3-cephem-4-carboxylate (100 mg) in anhydrous pyridine (0.2 ml) is treated with 2,2,2-trichloroethylisocyanate (27 μl). The reaction mixture is kept in a stoppered flask for 1 hour at room temperature, then evaporated in vacuo. The residue is dissolved in ethyl acetate (10 ml), washed with 0.5 M pH 2 phosphate buffer (2 × 2 ml) and water (2 × 4 ml), dried with magnesium sulfate and evaporated in vacuo to a foam. Chromatography of this material on silica gel affords 2,2,2-trichloroethyl d,1-7β-(D-α-amino-phenylacetamido)-3-(N-2,2,2-trichloroethyl)-carbamoyloxymethyl-3-cephem-4-carboxylate.

2,2,2-Trichloroethylisocyanate is prepared in the following manner: 2,2,2-trichloroethylamine (15.0 g) in anhydrous benzene (75 ml) is added dropwise to phosgene in benzene (435 ml of a 12.5% solution). The resulting suspension is heated overnight at 70° to give a solution, and then at reflux for 2 hours. Benzene (300 ml) is distilled off. The remainder of the solution is evaporated under reduced pressure to remove excess phosgene and solvent. Distillation of the residue yields 2,2,2-trichloroethylisocyanate (10.2 g) as a clear liquid, b.p. 63°–65° (28 mm).

EXAMPLE 55 d,1-7β-(D-α-Amino-phenylacetamido)-3-carbamoyloxymethyl-3-cephem-4-carboxylic acid 2,2,2-Trichloroethyl d,1-7β-(D-α-azido-phenylacetamido)-3-(N-2,2,2-trichloroethyl)carbamoyloxymethyl-3-cephem-4-carboxylate (119 mg) in 88% formic acid (2.0 ml) is treated with zinc dust (600 mg) in portions over 10 minutes. The mixture is stirred an additional 20 minutes. The zinc is filtered and washed with cold water (20 ml). The combined filtrate and washings are saturated at 0° with hydrogen sulfide and filtered through super cel, which is washed with water. The filtrate is washed with ethyl acetate (3 × 10 ml), pumped at high vacuum to remove dissolved ethyl acetate, and lyophilized, affording d,1-7β-(D-α-amino-phenylacetamido)-3-carbamoyloxymethyl-3-cephem-4-carboxylic acid as a powder.

EXAMPLE 56

2,2,2-Trichloroethyl d,1-7β-benzylideneamino-7-methoxy-3-methoxymethyloxymethyl-3-cephem-4-carboxylate 2,2,2-Trichloroethyl d,1-7α-benzylideneamino-3-methoxymethyloxymethyl-3-cephem-4-carboxylate (0.494 g) is dissolved in anhydrous tetrahydrofuran (12 ml) under nitrogen. The solution is cooled to −78° and phenyllithium (0.52 ml of a 2.3 M solution in 7:3 benzene-ether) is added dropwise over 0.5 minutes. After having been stirred for 1 minute, the mixture is treated with N-bromosuccinimide (0.214 g) in tetrahydofuran (8 ml). The reaction mixture is stirred at −78° for 2 minutes and then allowed to warm to room temperature. The solvent is removed under reduced pressure until the volume is 5 ml. The residue is taken up in methylene chloride (50 ml) and washed twice with pH 7 phosphate buffer. The organic phase is dried and evaporated to 10 ml and used directly below.

To a stirring suspension of silver oxide (0.464 g) in methanol (20 ml) is added over 10 minutes the above methylene chloride solution of bromo-Schiff's base. The reaction mixture is stirred for another 45 minutes. The silver salts are filtered off and the filtrate is evaporated in vacuo. The residue in methylene chloride is washed twice with pH 7 phosphate buffer, dried with magnesium sulfate, filtered and evaporated in vacuo to a gum. This is chromatographed on silica gel to give 2,2,2-trichloroethyl d,1-7β-benzylideneamino-7-methoxy-3-methoxymethyloxymethyl-3-cephem-4-carboxylate.

EXAMPLE 57

2,2,2-Trichloroethyl d,1-3-methoxymethyloxymethyl-7-methoxy-7β-(2-thienylacetamido)-3-cephem-4-carboxylate A solution of 2,2,2-trichloroethyl d,1-7β-benzylideneamino-7-methoxy-3-methoxymethyloxymethyl-3-cephem-4-carboxylate (0.304 g) in tetrahydrofuran (12 ml) is treated with water (2 ml) and palladium chloride (0.052 g). The mixture is stirred at room temperature for 4 hours. Evaporation of the solvent under reduced pressure leaves a residue which is triturated with three portions of petroleum ether, taken up in methylene chloride, and dried with magnesium sulfate. The solution is filtered and evaporated to an oil. This material is taken up in methylene chloride (8 ml), cooled to 0°, and treated successively with pyridine (0.30 ml) and 2-thienylacetyl chloride (0.086 ml). The reaction mixture is stirred at 0° for 15 minutes and then allowed to warm up in the next 15 minutes. The reaction mixture is diluted with methylene chloride, washed with pH 2 phosphate buffer and water, dried with magnesium sulfate, and concentrated in vacuo. The residue is purified by silica gel chromatography, affording 2,2,2-trichloroethyl d,1-3-methoxymethyloxymethyl-7-methoxy-7β-(2-thienylacetamido)-3-cephem-4-carboxylate.

EXAMPLE 58

2,2,2-Trichloroethyl d,1-3-hydroxymethyl-7-methoxy-7β-(2-thienylacetamido)-3-cephem-4-carboxylate A solution of 2,2,2-trichloroethyl d,1-3-methoxymethyloxymethyl-7-methoxy-7β-(2-thienylacetamido)-3-cephem-4-carboxylate (0.28 g) in dioxane (8 ml) is diluted with water (2 ml) and treated with 1N perchloric acid (0.05 ml). The resulting solution is kept at room temperature for 2 hours, then diluted with ethyl acetate and washed with water containing pH 9 phosphate buffer. The organic portion is separated, dried with magnesium sulfate, filtered, and evaporated in vacuo giving 2,2,2-trichloroethyl d,1-3-hydroxymethyl-7-methoxy-7β-(2-thienylacetamido)-3-cephem-4-carboxylate.

EXAMPLE 59

2,2,2-Trichloroethyl d,1-3-carbamoyloxymethyl-7-methoxy-7β-(2-thineylacetamido)-3-cephem-4-carboxylate Trichloroacetylisocyanate (0.087 g) is added to a solution of 2,2,2-trichloroethyl d,1-3-hydroxymethyl-7-methoxy-7β-(2-thienylacetamido)-3-cephem-4-carboxylate (0.217 g) in acetone (2.5 ml). The reaction mixture is kept overnight in a stoppered flask. The solvent is removed under vacuum and replaced by methanol (2 ml). Sodium carbonate (0.004 g) is added to the methanolic solution and the mixture is stirred at room temperature for 2 hours. The reaction mixture is diluted with ethyl acetate, washed with water, dried with magnesium sulfate, and evapoated in vacuo. Chromotography of the residue on silica gel gives 2,2,2-trichloroethyl d,1-3-carbamoyloxymethyl-7-methoxy-7β-(2-thienylacetamido)-3-cephem-4-carboxylate.

EXAMPLE 60 d,1-3-Carbamoyloxymethyl-7-methoxy-7β-(2-thienylacetamido)-3-cephem-4-carboxylic acid 2,2,2-Trichloroethyl d,1-3-carbamoyloxymethyl-7-methoxy-7β-(2-thienylacetamido)-3-cephem-4-carboxylate (0.112 g) is dissolved in 90% acetic acid (4 ml), and zinc dust (0.30 g) is added with stirring. The reaction mixture is stirred at room temperature for 15 minutes, filtered, and the residual zinc is washed with ethyl acetate. The filtrate is evaporated in vacuo to a solid residue which is partitioned between cold dilute aqueous sodium bicarbonate and ethyl acetate. The aqueous portion is separated, acidified to pH 2 with dilute hydrochloride acid, and extracted with ethyl acetate. The combined extracts are dried and evaporated in vacuo to yield d,1-3-carbamoyloxymethyl-7-methoxy-7β-(2-thineylacetamido)-3-cephem-4-carboxylic acid.

The free acid is dissolved in water containing an equivalent of sodium bicarbonate. Lyophilization of the solution yields sodium d,1-3-carbamoyloxymethyl-7-methoxy-7β-(2-thienyllacetamido)-3-cephem-4-carboxylate.

EXAMPLE 61

3-[2-(5-Methyl-1,3,4-thiadiazolyl)thio]-2-oxy-propyl N-(p-methoxybenzyloxycarbonyl-diethylphosphonomethyl)thioformimidate A solution of p-methoxybenzyl α-thioformamidediethylphosphonoacetate (1.876 g) in acetone (30 ml) is treated successively with potassium carbonate (0.725 g) and 1-chloro-3-[2-(5-methyl-1,3,4-thiadiazolyl)thio]-2-propanone (1.158 g). The resulting mixture is stirred under nitrogen for 14.5 hours at room temperature. The mixture is filtered and the filtrate is evaporated under reduced pressure yielding 3-[2-(5-methyl-1,3,4-thiadiazolyl)thiol]-2-oxo-propyl N-(p-methoxybenzyloxycarbonyl-diethylphosphonomethyl)thioformimimate.

When three equivalents of potassium carbonate are used in the foregoing example, the isolated product is predominantly p-methoxybenzyl 5-[2-(5-methyl-1,3,4-thiadiazolyl)thiomethyl]-6H-1,3-thiazine-4-carboxylate.

1-Chloro-3-[2-(5-methyl-1,3,4-thiadiazolyl)thio]-2-propanone is prepared as described below STEP 1.
Methyl[2-(5-methyl-1,3,4-thiadiazolyl)thio]acetate 2-Mercapto-5-methyl-1,3,4-thiadiazole (13.21 g) is added to a suspension of sodium hydride (4.22 g of a 57% dispersion in mineral oil, washed three times with hexane) in dimethyoxyethane (200 ml). The mixture is stirred at room temperature until hydrogen evolution ceases. Methyl chloroacetate (10.85 g) is then added dropwise over a period of 30 minutes. The reaction mixture is stirred at room temperature for 4 hours and is refluxed for 0.5 hours. After cooling, the mixture is diluted with a large excess of water and the product is extracted with ether. The ethereal solution is dried with magnesium sulfate, filtered, and evaporated in vacuo to give methyl [2-(5-methyl-1,3,4-thiadiazolyl)thio]acetate.

STEP 2. [2-(5-methyl-1,3,4-thiadiazolyl)thio]acetic acid

A mixture of methyl[2-(5-methyl-1,3,4-thiadiazolyl)thio]acetate (10.20 g), methanol (300 ml), and 1N aqueous sodium hydroxide (50 ml) is stirred at room temperature for 18 hours. The mixture is evaporated in vacuo to dryness and the residue is taken up in water (200 ml) and filtered. The aqueous filtrate is layered with ethyl acetate (100 ml) and acidified to pH 3 with concentrated hydrochloric acid. The organic phase is separated, dried with magnesium sulfate, and evaporated in vacuo to afford [2-(5-methyl-1,3,4-thiadiazolyl)thio]acetic acid.

STEP 3. [2-(5-methyl-1,3,4-thiadiazolyl)thio]-acetyl chloride

Oxalyl chloride (4.25 ml) and dimethyl formamide (0.4 ml) are added to a cold (ice bath), stirring suspension of [2-(5-methyl-1,3,4-thiadiazolyl)thio]acetic acid (4.76 g) in dry benzene (100 ml). The reaction mixture is stirred for 1 hour at 5° followed by 1 hour at room temperature, then washed with ice-cold saturated brine, dried over magnesium sulfate, and concentrated in vacuo. The residue is diluted with dry benzene and evaporated again, affording [2-(5-methyl-1,3,4-thiadiazolyl)thio]acetyl chloride.

STEP 4.
1-Chloro-3-[2-(5-methyl-1,3,4-thiadiazolyl)thio]-2-propanone

The acid chloride obtained in the previous step (5.3 g) is dissolved in ether (100 ml) and added over 30 minutes to an ice-cold, stirring solution of diazomethane (1.1 g) and triethylamine (2.53 g) in ether (50 ml). The mixture is stirred at 0° for 6 hours. Triethylamine hydrochloride is filtered off and washed with ether. The combined filtrate and washings are cooled in an ice-bath and treated with anhydrous hydrogen chloride for 5 minutes. The resulting solution is washed with cold water, cold 5% aqueous sodium bicarbonate, and brine, dried over magnesium sulfate, and evaporated in vacuo to yield 1-chloro-3-[2-(5-methyl-1,3,4-thiadiazolyl)thio]-2-propanone.

EXAMPLE 62 p-Methoxybenzyl 5-[2-(5-methyl-1,3,4-thiadiazolyl)thiomethyl]-6H-1,3-thiazine-4-carboxylate A suspension of sodium hydride (0.25 g of a 50% dispersion in mineral oil, washed three times with hexane) in anhydrous dimethoxyethane (10 ml) is added to a solution of 3-[2-(5-methyl-1,3,4-thiadiazolyl)thio]-2-oxo-propyl N-(p-methoxybenzyloxycarbonyl-diethylphosphonomethyl)thioformimidate (2.75 g) in dimethoxyethane (30 ml). After stirring for 5 minutes, the reaction mixture is diluted with benzene and washed with water. The organic phase is dried with magnesium sulfate, filtered, and evaporated in vacuo, leaving p-methoxybenzyl 5-[2-(5-methyl-1,3,4-thiadiazolyl)thiomethyl]-6H-1,3-thiazine-4-carboxylate.

EXAMPLE 63 p-Methoxybenzyl d,1-7α-azido-3-[2-(5-methyl-1,3,4-thiadiazolyl)thiomethyl]-3-cephem-4-carboxylate Triethylamine (0.61 g) in methylene chloride (5 ml) is added to a solution of p-methoxybenzyl 5-[2-(5-methyl-1,3,4-thiadiazolyl)thiomethyl]-6H-1,3,-thiazine-4-carboxylate (1.63 g) in dry methylene chloride (40 ml). The resulting solution is stirred under nitrogen, with ice-bath cooling, while azidoacetyl chloride (0.72 g) in methylene chloride (20 ml) is added dropwise over a period of 2 hours. After warming to room temperature, the reaction mixture is washed with four portions of water, dried with magnesium sulfate, filtered, and evaporated in vacuo to a dark oil. This material is purified by silica gel chromatography, affording p-methoxybenzyl d,1-7α-azido-3-[2-(5-methyl-1,3,4-thiadiazolyl)thiomethyl]-3-cephem-4-carboxylate.

EXAMPLE 64 p-Methoxybenzyl d,1-7α-amino-3-[2-(5-methyl-1,3,4-thiadiazolyl)thiomethyl]-3-cephem-4-carboxylate p-Methoxybenzyl d,1-7α-azido-3-[2-(5-methyl-1,3,4-thiadiazolyl)thiomethyl]-3-cephem-4-carboxylate (0.78 g) in benzene (40 ml) is hydrogenated at 40 psi with platinum oxide (0.50 g) for 1 hour. The mixture is evaporated in vacuo to a black gum. This material, in ethyl acetate, is filtered through a pad of silica gel G-super cel (1:1 ratio) which is washed with more ethyl acetate. The combined filtrate and washings are evaporated in vacuo to give p-methoxybenzyl d,1-7α-amino-3-[2-(5-methyl-1,3,4-thiadiazolyl)thiomethyl]-3-cephem-4-carboxylate.

EXAMPLE 65 p-Methoxybenzyl d,1-7α-benzylideneamino-3-[2-(5-methyl-1,3,4-thiadiazolyl)thiomethyl]-3-cephem-4-carboxylate A mixture of p-methoxybenzyl d,1-7α-amino-3-[2-(5-methyl-1,3,4-thiadiazolyl)thiomethyl]-3-cephem-4-carboxylate (0.557 g), p-nitrobenzaldehyde (0.181 g), methylene chloride (25 ml), and magnesium sulfate (2.50 g) is stirred at room temperature for 15 hours. The mixture is filtered and the filtrate evaporated in vacuo to dryness. The residue is twice diluted with benzene and evaporated, affording p-methoxybenzyl d,1-7α-benzylideneamino-3-[2-(5-methyl-1,3,4-thiadiazolyl)thiomethyl]-3-cephem-4-carboxylate.

EXAMPLE 66 p-Methoxybenzyl d,1-7β-benzylideneamino-3-[2-(5-methyl-1,3,4-thiadiazolyl)thiomethyl]-3-cephem-4-carboxylate A solution of p-methoxybenzyl d,1-7α-benzylideneamino-3-[2-(5-methyl-1,3,4-thiadiazolyl)thiomethyl]-3-cephem-4-carboxylate (0.688 g) in anhydrous tetrahydrofuran (10 ml) is cooled to —78° under nitrogen. Phenyllithium (0.50 ml. of a 2.3 M solution in benzene-ether) is added rapidly with stirring. Dimethylformamide (12.5 ml) is then added dropwise over 5 minutes. After stirring 1 more minute at —78°, the reaction is quenched with a solution of water (0.21 ml) and acetic acid (0.16 ml) in tetrahydrofuran (5 ml). The mixture is allowed to warm to room temperature, then it is diluted with benzene and washed with six portions of water. The second wash is treated with pH 3 phosphate buffer and the fifth with pH 9 phosphate buffer. The benzene solution, after being dried with magnesium sulfate, is evaporated in vacuo to yield a mixture of p-methoxybenzyl d,1-7α-benzylideneamino-3-[2-(5-methyl-1,3,4-thiadiazolyl)thiomethyl]-3-cephem-4-carboxylate and p-methoxybenzyl d,1-7β-benzylideneamino-3-[2-(5-methyl-1,3,4-thiadiazolyl)thiomethyl]-3-cephem-4-carboxylate.

EXAMPLE 67 p-Methoxybenzyl d,1-7β-amino-3-[2-(5-methyl-1,3,4-thiadiazolyl)thiomethyl]-3-cephem-4-carboxylate p-Methoxybenzyl d,1-7-benzylideneamino-3-[2-(5-methyl-1,3,4-thiadiazolyl)thiomethyl]-3-cephem-4-carboxylate (0.633 g, mixture of 7α- and 7β-isomers) in chloroform (5 ml) is added to a mixture of p-toluenesulfonic acid monohydrate (0.202 g) and 2,4-dinitrophenylhydrazine (0.210 g) in ethanol (30 ml, mixture stirred previously for 45 minutes). After stirring 30 minutes at room temperature, the mixture is filtered and the filtrate is evaporated in vacuo to dryness. The residue is treated with water (15 ml) containing 1 M dipotassium hydrogen phosphate (2 ml) and extracted with ether (3 × 10 ml). The ethereal extracts are dried with magnesium sulfate, filtered, and evaporated in vacuo. The residual oil is a mixture of p-methoxybenzyl d,1-7α-amino-3-[2-(5-methyl-1,3,4-thiadiazolyl)thiomethyl]-3-cephem-4-carboxylate and p-methoxybenzyl d,1-7β-amino-3-[2-(5-methyl-1,3,4-thiadiazolyl)thiomethyl]-3-cephem-4-carboxylate.

EXAMPLE 68 p-Methoxybenzyl d,1-7α-[1-(1H)-tetrazoylacetamido]-3-[2-(5-methyl-1,3,4-thiadiazolyl)thiomethyl]-3-cepham-4-carboxylate and p-methoxybenzyl d,1-7β-[1-(1H)-tetrazolylacetamido]-3-[2-(5-methyl-1,3,4-thiadiazolyl)thiomethyl]-3-cephem-4-carboxylate A solution of p-methoxybenzyl d,1-7-amino-3-[2-(5-methyl-1,3,4-thiadiazolyl)thiomethyl]-3-cephem-4-carboxylate (0.46 g, mixture of 7α- and 7β-isomers) in dry methylene chloride (8 ml) is cooled in an ice-bath under nitrogen. Pyridine (0.45 ml) and 1-(1H)-tetrazolylacetyl chloride (0.145 g) are added in quick succession. The reaction mixture is stirred for 15 minutes at 0°, then diluted with benzene and washed five times with water. The first and second washes are acidified with pH 2 buffer and the fourth is basified with pH 9 buffer. The benzene solution is dried over magnesium sulfate, filtered, and evaporated in vacuo to an oil. This material is separated by silica gel chromatography into p-methoxybenzyl d,1-7α-[1-(1H)-tetrazolylacetamido]-3-[2-(5-methyl-1,3,4-thiadiazolyl)-thiomethyl]-3-cephem-4-carboxylate and p-methoxybenzyl d,1-7β-[1-(1H)-tetrazolylacetamido]-3-[2-(5-methyl-1,3,4-thiadiazolyl)thiomethyl]-3-cephem-4-carboxylate.

EXAMPLE 69 d,1-7β-[1-(1H)-Tetrazolylacetamido]-3-[2-(5-methyl-1,3,4-thiadiazolyl)thiomethyl]-3-cephem-4-carboxylic acid Ice-cold trifluoroacetic acid (2.5 ml) is added to a cold mixture of anisole (0.5 ml) and p-methoxybenzyl d,1-7β-[1-(1H)-tetrazolylacetamido]-3-[2-(5-methyl-1,3,4-thiadiazolyl)thiomethyl]-3-cephem-4-carboxylate (0.106 mg). The resulting solution is kept at 0° for 5 minutes, then evaporated in vacuo at 0° to remove excess trifluoroacetic acid. The oily residue is diluted with toluene and evaporated in vacuo to dryness. The resulting semi-solid is taken up in dilute aqueous sodium bicarbonate and extracted with methylene chloride. The aqueous portion is acidified to pH 2.5 and extracted with ethyl acetate. Evaporation of the ethyl acetate, after drying over magnesium sulfate, affords d,1-7β-[1-(1H)-tetrazolylacetamido]-3-[2-(5-methyl-1,3,4-thiadiazolyl)thiomethyl]-3-cephem-4-carboxylic acid. This acid is dissolved in a slight excess of aqueous sodium bicarbonate. Dilution of the solution with ethanol gives a precipitate of sodium d,1-7β-[1-(1H)-tetrazolylacetamido]-3-[2-(5-methyl-1,3,4 -thiadiazolyl)-thiomethyl]-3-cephem-4-carboxylate.

EXAMPLE 70

Dibutyl N-benzyl-aminomethylphosphonate hydrochloride

A mixture of 1,3,5-tribenzyl-sym-hexahydrotriazene (59.6 g) and dibutyl phosphite (97.1 g) is heated with stirring at 100° for 6 hours. After cooling to room temperature the reaction mixture is diluted with ethyl ether (1000 ml). This solution is cooled in an ice-bath and treated with anhydrous hydrochloric acid until no further precipitate separates. The crude product is collected, washed with ether, and recrystallized to afford dibutyl N-benzyl-aminomethylphosphonate hydrochloride.

EXAMPLE 71

Dibutyl aminomethylphosphonate hydrochloride

A mixture of dibutyl N-benzyl-aminomethylphosphonate hydrochloride (122.4 g) and 10% palladium on powdered charcoal (5.0 g) in ethanol (1000 ml) is hydrogenated at 40 psi for 2 hours. The catalyst is removed by filtration and the filtrate is evaporated under reduced pressure to yield dibutyl aminomethylphosphonate hydrochloride.

EXAMPLE 72

Dibutyl aminomethylphosphonate

A solution of dibutyl aminomethylphosphonate hydrochloride (88.4 g) in water (400 ml) is treated with dipotassium hydrogen phosphate (183.0 g) and water (800 ml). The mixture is stirred until clear, then extracted with four portions of methylene chloride. The combined extracts are dried over magnesium sulfate, filtered, and evaporated under reduced pessure to leave dibutyl aminomethylphosphonate.

EXAMPLE 73

Dibutyl N-benzylidene-aminomethylphosphonate

A mixture of dibutyl aminomethylphosphonate (69.7 g) and benzaldehyde (33.0 g) in benzene (600 ml) is stirred with magnesium sulfate (150 g) for 3 hours. The mixture is filtered and the salts washed with benzene. Concentration of the filtrate in vacuo leaves dibutyl N-benzylideneaminomethylphosphonate.

EXAMPLE 74 p-Bromophenacyl N-benzylidene-α-amino-dibutylphosphonoacetate

Dibutyl N-benzylidene-aminomethylphosphonate (31.1 g) is dissolved in anhydrous tetrahydrofuran (500 ml) and the solution is cooled to −78° under a nitrogen atmosphere. Butyllithium (46 ml of a 2.2 M solution in hexane) is added over a period of 5 minutes. The resulting solution is stirred an additional 30 minutes at −78°, then treated dropwise over a period of 45 minutes with p-bromophenacyl chloroformate (13.9 g) in tetrahydrofuran (100 ml). The reaction mixture is stirred an additiona 2 hours at −78° followed by gradual warming to 3° over a period of 30 minutes. Evaporation of the solvent in vacuo leaves a gum which is partitioned between ether (500 ml) and 0.5 M pH 3 phosphate buffer (100 ml). The ethereal phase is separated, washed with water and saturated brine, dried over magnesium sulfate filtered, and evaporated in vacuo to an oil. Chromatographic purification of this material on silica gel gives p-bromophenacyl N-benzylidene-α-amino-dibutylphosphonoacetate.

The p-bromophenacyl chloroformate used in the above example is prepared as follows: A solution of p-bromophenacyl alcohol (21.4 g) and triethylamine (10.1 g) in anhydrous benzene (50 ml) is added dropwise over 30 minutes to a cooled (ice-bath) stirring solution of phosgene in benzene (170 ml of a 12.5% solution). The flask is stoppered and the reaction mixture is allowed to stand at room temperature overnight. The triethylamine hydrochloride is filtered off and the filtrate is concentrated in vacuo to remove excess phosgene and solvent. Fresh benzene is added and evaporated in vacuo. This operation is repeated several times in order to remove the last traces of phosgene. The final evaporation affords crude p-bromophenacyl chloroformate.

EXAMPLE 75 p-Bromophenacyl α-amino-dibutylphosphonoacetate

A solution of p-bromophenacyl N-benzylidene-α-amino-dibutylphosphoneacetate (15.4 g) in ethyl ether (100 ml) is added dropwise over 25 minutes to a stirring solution of p-toluenesulfonic acid monohydrate (5.4 g) in ethyl ether (150 ml). A precipitate separates immediately. Cyclohexane (100 ml) is added to the mixture and the solvents are separated. The residue is washed with more 2:1 ethyl ether-cyclohexane which is again decanted off. The precipitate is diluted with 1 M dipotassium hydrogen phosphate (60 ml) and water and extracted with methylene chloride. The organic phase is dried over magnesium sulfate, filtered, and evaporated in vacuo to yield p-bromophenacyl α-amino-dibutylphosphonoacetate.

EXAMPLE 76 p-Bromophenacyl α-thioformamido-dibutylphosphonoacetate

A solution of p-bromophenacyl α-amino-dibutylphosphonoacetate (12.36 g) in carbon tetrachloride (15 ml) is added dropwise to an ice-cold, stirring solution of ethyl thionoformate (2.64 g) in carbon tetrachloride (5 ml). The cooling bath is removed and the solution is kept overnight in a stoppered flask. The solvent and excess reagent are evaporated under reduced pressure. Chromatography of the oily residue on silica gel affords p-bromophenacyl α-thioformamido-dibutylphosphonoacetate.

EXAMPLE 77 p-Bromophenacyl 5-isobutyryloxymethyl-6H-1,3-thiazine-4-carboxylate

A solution of p-bromophenacyl α-thioformamido-dibutylphosphonoacetate (6.10 g) in acetone (50 ml) is treated with powdered potassium carbonate (4.98 g). The mixture is stirred under a nitrogen atmosphere while 1-chloro-3-isobutyryloxy-2-propanone (2.32 g) in acetone (10 ml) is added dropwise over 10 minutes. The reaction mixture is stirred an additional 3 hours at room temperature, then filtered. Evaporaton of the filtrate under reduced pressure leaves a dark oil which is extracted with carbon tetrachloride (2 × 50 ml). The combined extracts are washed with 0.5 M dipotassium hydrogen phosphate, water, and saturated brine, dried over magnesium sulfate, and evaporaged in vacuo to give crude p-bromophenacyl 5-isobutyryloxymethyl-6H-1,3-thiazine-4-carboxylate.

The 1-chloro-3-isobutyryloxy-2-propanone utilized in the above example is prepared in the following manner. To a solution of lithium isobutyrate (9.4 g) in hexamethylphosphoric triamide (25 ml) is added 1,3-dichloropropanone (12.7 g). The resulting mixture is kept at room temperature for 3 hours, then diluted with benzene (200 ml) and washed six times with water. The organic solution is dried over magnesium sulfate, filtered, and evaporated under reduced pressure. Distillation of the residue under vacuum affords 1-chloro-3-isobutyryloxy-2-propanone.

EXAMPLE 78 p-Bromophenacyl d,1-7α-azido-3-isobutyryloxymethyl-3-cephem-4-carboxylate

Triethylamine (1.83 g) is added to a solution of p-bromophenacyl 5-isobutyryloxymethyl-6H-1,3-thiazine-4-carboxylate (5.35 g) in anhydrous methylene chloride (100 ml). The resulting solution is cooled in an ice-bath and stirred under a nitrogen atmosphere. Azidoacetyl chloride (2.15 g) in methylene chloride (50 ml) is added dropwise over 2 hours to the solution. The reaction mixture is washed repeatedly with water, dried over magnesium sulfate, and evaporated under reduced pressure to a dark oil. -isobutyryloxymethyl-material is purified by silica gel chromatography giving p-bromophenacyl d,1-7α-azido-3-isobutyryloxymethyl-3-cephem-4-carboxylate.

EXAMPLE 79 p-Bromophenacyl d,1-7α-amino-3-isobutyryloxymethyl-3-cephem-4-carboxylate

A mixture of p-bromophenacyl d,1-7α-azido-3-isobutyryloxymethyl-3-cephem-4-carboxylate (0.62 g), platinum oxide (0.25 g), and benzene (30 ml), is shaken under 40 psi of hydrogen for 30 minutes. The benzene is distilled under vacuum and the residue taken up in ethyl acetate. This mixture is passed through a filter pad of 1:1 silica gel G-super cel to remove the catalyst. Evaporation of the filtrate under reduced pressure gives p-bromophenacyl d,1-7α-amino-3-isobutyryloxymethyl- 3-cephem-4-carboxylate.

EXAMPLE 80 p-Bromophenacyl d,1-3-isobutyryloxymethyl-7α-(p-nitrobenzylideneamino)-3-cephem-4-carboxylate A mixture of p-bromophenacyl d,1-7α-amino-3-isobutyryloxymethyl-3-cephem-4-carboxylate (0.50 g), p-nitrobenzaldehyde (0.15 g), and magnesium sulfate (2.50 g) in methylene chloride (25 ml) is stirred in a stoppered flask for 16 hours at room temperature. The mixture is filtered and the filtrate is concentrated under reduced pressure. The residue is taken up in benzene and the solvent evaporated in vacuo. Repetition of this operation yields p-bromophenacyl d,1-3-isobutyryloxymethyl-7α-(p-nitrobenzylideneamino)-3-cephem-4-carboxylate.

EXAMPLE 81 p-Bromophenacyl d,1-3-isobutyryloxymethyl-7β-(p-nitrobenzylideneamino)-3-cephem-4-carboxylate p-Bromophenacyl d,1-3-isobutyryloxymethyl-7α-(p-nitrobenzylideneamino)-3-cephem-4-carboxylate (0.60 g) is dissolved in anhydrous tetrahydrofuran (15 ml) and the solution is cooled to −78° under nitroen. One equivalent of phenyllithium (0.41 ml of a 2.3 M solution in 7:3 benzene-ether) is added, forming the anion. Dimethylformamide (20 ml) is then added dropwise over 5 min. After one more minute at −78°, a solution of water (0.17 ml) and acetic acid (0.14 ml) in tetrahydrofuran (10 ml) is added. The reaction mixture is allowed to warm to room temperature; benzene (250 ml) is added, and the solution is washed six times with water. The second wash is acidified with pH 2 phosphate buffer and the fifth basified with pH 8 buffer. The benzene solution is dried with magnesium sulfate, filtered, and evaporated under reduced pressure leaving a mixture of p-bromophenacyl d,1-3-isobutyryloxymethyl-7α-(p-nitrobenzylideneamino)-3-cephem-4-carboxylate and p-bromophenacyl d,1-3-isobutyryloxymethyl-7β-(p-nitrobenzylideneamino)-3-cephem-4-carboxylate

EXAMPLE 82 p-Bromophenacyl d,1-7β-amino-3-isobutyryloxymethyl-3-cephem-4-carboxylate p-Bromophenacyl d,1-3-isobutyryloxymethyl-7-(p-nitrobenzylideneamino)-3-cephem-4-carboxylate (524 mg, mixture of 7α and 7β-isomers) is dissolved in chloroform (3 ml) and added to a solution of 2,4-dinitrophenylhydrazine p-toluenesulfonate in ethanol (prepared from 164 mg of 2,4-dinitrophenylhydrazine and 158 mg of p-toluenesulfonic acid monohydrate stirred in 30 ml of ethanol previously for 45 minutes). The mixture is stirred for 30 minutes, filtered, and evaporated. The residue is treated with aqueous pH 9.2 phosphate buffer and extracted three times with ether. The ether portions are dried over magnesium sulfate, filtered, and evaporated in vacuo providing p-bromophenacyl d,1-7α-amino-3-isobutyryloxymethyl-3-cephem-4-carboxylate and p-bromophenacyl d,1-7β-amino-3-isobutyryloxymethyl-3-cephem-4-carboxylate.

EXAMPLE 83 p-Bromophenacyl d,1-7α-(2-furylacetamido)-3-isobutyryloxymethyl-3-cephem-4-carboxylate and p-bromophenacyl d,1-7β-(2-furylacetamido)-3-isobutyryloxymethyl-3-cephem-4-carboxylate A mixture (200 mg) of p-bromophenacyl d,1-7α-amino-3-isobutyryloxymethyl-3-cephem-4-carboxylate and p-bromophenacyl d,1-7β-amino-3-isobutyryloxymethyl-3-cephem-4carboxylate is dissolved in anhydrous methylene chloride (4 ml). The solution is cooled in an ice-bath, treated with pyridine (0.2 ml) and 2-furylacetyl chloride (58 mg), and stirred in the cold for 15 minutes. Benzene (30 ml) is added to the reaction mixture and the resulting solution is washed with aqueous pH 2 phosphate buffer, water, aqueous pH 9 phosphate buffer, water, and saturated brine. The benzene portion is dried over magnesium sulfate, filtered, and evaporated under reduced pressure to an oil. Chromatography of the crude product on slica gel affords p-bromophenacyl d,1-7α-(2-furylacetamido)-3-isobutyryloxymethyl-3-cephem-4-carboxylate and p-bromophenacyl d,1-7β-(2-furylacetamido)-3-isobutyryloxymethyl-3-cephem-4-carboxylate.

EXAMPLE 84 d,l-7β-(2-Furylacetamido)-3-isobutyryloxymethyl-3-cephem-4-carboxlic acid p-Bromophenacyl d,1-7β-(2-furylacetamido)-3-isobutyryloxymethyl-3-cephem-4-carboxylate (78 mg) in 90% aqueous acetic acid (2 ml) is stirred with powdered zinc (390 mg) for 10 minutes at room temperature. The zinc is filtered and washed with ethyl acetate. The filtrate and washings are evaporated in vacuo to a gum which is taken up in water containing sodium bicarbonate (110 mg). The aqueous solution is extracted with methylene chloride, acidified to pH 2.5, and extracted with ethyl acetate. The ethyl acetate solution is dried over magnesium sulfate, filtered, and evaporated providing d,1-7β-(2-furylacetamido)-3-isobutyryloxymethyl-3-cephem-4-carboxylic acid.

The above acid (45 mg) is dissolved in 0.03 M aqueous sodium bicarbonate (4 ml) and the solution is lyophilized to give sodium d,1-7β-(2-furylacetamido)-3-isobutyryloxymethyl-3-cephem-4-carboxylate.

EXAMPLE 85

Diphenyl N-benzyl-aminomethylphosphonate hydrochloride

A mixture of 1,3,5-tribenzyl-sym-hexahydrotriazene (119.2 g) and diphenyl phosphite (234.2 g) is heated with stirring at 100° for 6 hours in a flask protected from moisture by a drying tube. The mixture is allowed to cool gradually to room temperature overnight, then dissolved in ethyl ether (2.5 l). The solution is cooled in ice and anhydrous hydrochloric acid is passed through it until no further precipitate forms. The precipitate is collected and recrystallized to afford pure diphenyl N-benzyl-aminomethylphosphonate hydrochloride.

EXAMPLE 86

Diphenyl aminomethylphosphonate hydrochloride

A mixture of diphenyl N-benzyl-aminomethylphosphonate hydrochloride (185.0 g), 10% palladium on carbon (7.0 g), and ethanol (1500 ml) is hydrogenated at 40 psi until hydrogen absorption ceases. The catalyst is removed by filtration through a pad of super cel and the filtrate is evaporated under reduced pressure to give diphenyl aminomethylphosphonate hydrochloride.

EXAMPLE 87

Diphenyl aminomethylphosphonate

To a solution of diphenyl aminomethylphosphonate hydrochloride (134.8 g) in water (500 ml) is added dipotassium hydrogen phosphate (235.5 g) and water (1000 ml). The mixture is stirred until clear, then extracted with four portions of methylene chloride. The organic phase is dried over magnesium sulfate, filtered, and evaporated in vacuo to afford diphenyl aminomethylphosphonate.

EXAMPLE 88

Diphenyl N-benzylidene-aminomethylphosphonate

A solution of diphenyl aminomethylphosphonate (102.8 g) and benzaldehyde (41.6 g) in benzene (1000 ml) is heated at reflux in a Dean-Stark apparatus until water separation ceases. The resulting solution is evaporated under reduced pressure to yield diphenyl N-benzylideneaminomethylphosphonate.

EXAMPLE 89 p-Nitrobenzyl N-benzylidene-α-amino-diphenylphosphonoacetate

Phenyllithium (45 ml of a 2.3 M solution in 7:3 benzene-ether) in added to a dry-ice-cooled, stirring solution of diphenyl N-benzylidene-aminomethylphosphonate (35.1 g) in anhydrous tetrahydrofuran (500 ml). After having been stirred for 15 minutes at −78° under a nitrogen atmosphere, the solution is treated dropwise over 1 hour with p-nitrobenzyl chloroformate (10.8 g) in tetrahydrofuran (100 ml). The resulting solution is stirred an additional 2 hours at −78°, then allowed to warm to 5° over a period of 30 minutes. Evaporation of the solvent under reduced pressure leaves a residue which is partitioned between ethyl ether (500 ml) and 0.5 pH 3 phosphate buffer (200 ml). The aqueous phase is separated and extracted with ethyl ether (2 × 100 ml). The combined ethereal solution is washed with saturated brine, dried over magnesium sulfate, filtered, and concentrated in vacuo. Chromatography of the residue on silica gel affords p-nitrobenzyl N-benzylidene-α-amino-diphenylphosphonoacetate as well as starting material.

EXAMPLE 90 p-Nitrobenzyl α-amino-diphenylphosphonoacetate

A solution of p-nitrobenzyl N-benzylidene-α-aminodiphenylphosphonoacetate (16.43 g) in ethyl ether (100 ml) is added dropwise over 30 minutes to a stirring solution of p-toluenesulfonic acid monohydrate (6.48 g) in ethyl ether (150 ml). Cyclohexane (100 ml) is added to the mixture and the solvents are decanted from the precipitate. The precipitate is washed with more 2:1 ethyl ether-cyclohexane which is again decanted off. The precipitate is treated with 1 M aqueous dipotassium hydrogen phosphate (60 ml) and extracted with four portions of methylene chloride. The methylene chloride solution is dried over magnesium sulfate, filtered, and evaporated to give p-nitrobenzyl α-aminodiphenylphosphonacetate.

EXAMPLE 91 p-Nitrobenzyl α-thioformamido-diphenylphosphonoacetate

A mixture of p-nitrobenzyl α-amino-diphenylphosphonoacetate (5.0 g), ethyl thionoformate (5 ml), and hydrogen sulfide (5 ml) in a sealed thick-walled tube is left standing overnight at room temperature. The tube is cooled in dry-ice and the seal removed. A boiling chip is placed in the solution and it is allowed to slowly come to room temperature. Nitrogen is bubbled in to remove final traces of hydrogen sulfide. The residue is dissolved in methylene chloride, filtered, and evaporated under reduced pressure. Chromatography of the residue on silica gel gives p-nitrobenzyl α-thioformamido-diphenylphosphonoacetate.

EXAMPLE 92 p-Nitrobenzyl 5-methoxymethyl-6H-1,3-thiazine-4-carboxylate

A mixture of p-nitrobenzyl α-thioformamidodiphenylphosphonoacetate (2.43 g), powdered anhydrous potassium carbonate (2.07 g), 1-chloro-3-methoxy-2-propanone (0.67 g), and acetone (25 ml) is stirred under a nitrogen atmosphere at room temperature for 16 hours. The mixture is filtered and the filtrate evaporated under reduced pressure. The residue is dissolved in methylene chloride, washed twice with water and saturated brine, dried over MgSO$_4$, filtered, and evaporated in vacuo to yield crude p-nitrobenzyl 5-methoxymethyl-6H-1,3-thiazine-4-carboxylate.

The thiazine is also obtained in two stages as described below.

EXAMPLE 93

3-Methoxy-2-oxo-propyl N-(p-nitrobenzyloxycarbonyldiphenylphosphonomethyl)thioformimidate A mixture of p-nitrobenzyl α-thioformamidodiphenylphosphonoacetate (2.43 g), powdered potassium carbonate (0.73 ), 1-chloro-3-methoxy-2-propanone (0.63 g), and acetone (25 ml) is stirred in a capped flask at room temperature for 16 hours. The mixture is filtered and the filtrate is evaporated in vacuo to afford 3-methoxy-2-oxopropyl N-(p-nitrobenzyloxycarbonyl-diphenylphosphonomethyl)thioformimidate.

EXAMPLE 94 p-Nitrobenzyl 5-methoxymethyl-6H-1,3-thiazine-4-carboxylate

A suspension of sodium hydride (0.23 g of a 57% dispersion in mineral oil, washed three times with hexane) in anhydrous dimethoxyethane (15 ml) is added to a solution of 3-methoxy-2-oxo-propyl N-(p-nitrobenzyloxycarbonyldiphenylphosphonomethyl)thioformimidate (2.81 g) in the same solvent (70 ml). The resulting mixture is stirred 5 minutes, quickly added to benzene, and washed with water. The organic phase is dried over magnesium sulfate, filtered, and evaporated in vacuo to give p-nitrobenzyl 5-methoxymethyl-6H-1,3-thiazine-4-carboxylate.

The 1-chloro-3-methoxy-2-propanone used in the above condensations is prepared as follows: A solution of methoxyacetyl chloride (10.85 g) in anhydrous ethyl ether (25 ml) is added dropwise during 30 minutes to a stirred cooled (ice-salt bath) solution of diazomethane (4.2 g) and triethylamine (10.1 g) in anhydrous ether (200 ml). The mixture is stirred an additional 3 hours in the cold, then filtered through a pad of magnesium sulfate. The ethereal filtrate of crude diazoketone is cooled in an ice bath, and a stream of anhydrous hydrogen chloride is bubbled through the solution for 10 minutes. The resulting mixture is washed with ice-cold water and ice-cold 5% aqueous sodium bicarbonate, dried over magnesium sulfate, filtered, and concentrated. Distillation of the residue under reduced pressure affords 1-chloro-3-methoxy-2-propanone.

EXAMPLE 95 p-Nitrobenzyl d,1-7α-azido3-methoxymethyl-3-cephem-4-carboxylate p-Nitrobenzyl 5-methoxymethyl-6H1,3-thiazine-4-carboxylate (2.35 g) in anhydrous methylene chloride (40 ml) is stirred under a nitrogen atmosphere at 0°. Triethylamine (0.81 g) in methylene chloride (10 ml) is added all at once, followed by the dropwise addition of a solution of azidoacetyl chloride (0.96 g) in methylene chloride (30 ml) over a period of 60 minutes. After having been stirred at 0°for an additional 60 minutes, the solution is washed with water and brine, dried over magnesium sulfate, and evaporated in vacuo to a dark oil. The crude product is chromatographed on silica gel to afford p-nitrobenzyl d,1-7α-3-methoxymethyl-3-cephem-4-carboxylate.

EXAMPLE 96 p-Nitrobenzyl d,1-7α-amino-3-methoxymethyl-3-cephem-4-carboxylate

Freshly prepared aluminum amalgam (2.0 g) is added to an ice-cold solution of p-nitrobenzyl d, 1-7α-azido-3-methoxymethyl-3-cephem-4-carboxylate (1.09 g) in 96% aqueous tetrahydrofuran (20 ml). The reaction mixture is stirred vigorously for 8 minutes, quenched with magnesium sulfate, and filtered with the aid of ethyl acetate (100 ml). The filtrate is washed twice with water and saturated brine, dried over magnesium sulfate, filtered and evaporated in vacuo to yield p-nitrobenzyl d,1-7α-amino-3-methoxymethyl-3-cephem-4-carboxylate.

EXAMPLE 97 p-Nitrobenzyl d,1-3-methoxymethyl-7α-(p-nitrobenzylideneamino)-3-cephem-4-carboxylate A mixture of p-nitrobenzyl d,1-7α-amino-3-methoxymethyl-3-cephem-4-carboxylate (0.96 g), p-nitrobenzaldehyde (0.38 g), magnesium sulfate (6.0 g), and methylene chloride (60 ml) is stirred in a capped flask at room temperature for 15 hours. This mixture is filtered and the filtrate is concentrated under reduced pressure. The residual gum is three times dissolved in benzene and evaporated in vacuo to afford p-nitrobenzyl d,1-3-methoxymethyl-7α-(p-nitrobenzylideneamino)-3-cephem-4-carboxylate.

EXAMPLE 98 p-Nitrobenzyl d,1-3-methoxymethyl-7β-(p-nitrobenzylideneamino)-3-cephem-4-carboxylate A solution of p-nitrobenzyl d,1-3-methoxymethyl-7α-(p-nitrobenzylideneamino)-3-cephem-4-carboxylate (1.23 g) in anhydrous tetrahydrofuran (35 ml) is cooled in a dry iceacetone bath under a nitrogen atmosphere. Phenyllithium (1.05 ml of a 2.3 M solution in 7:3 benzene-ether) is added rapidly with stirring to give an inky blue solution. Dimethyl formamide (45 ml) is added dropwise over a period of 10 minutes to the reaction mixture. After having been stirred an additional 1 minute at −78°, the reaction is quenched by addition of a solution of water (0.43 ml) and acetic acid (0.35 ml) in tetrahydrofuran (10 ml). The reaction mixture is allowed to warm to room temperature, then diluted with benzene (500 ml) and washed with five portions of water. The second wash is acidified with pH 3 phosphate buffer and the fourth basified with pH 9 phosphate buffer. The benzene solution is dried over magnesium sulfate, filtered, and evaporated in vacuo to give a mixture of p-nitrobenzyl d, 1-3-methoxymethyl-7α-(p-nitrobenzylideneamino)-3-cephem4-carboxylate and p-nitrobenzyl d,1-3-methoxymethyl-7β-(p-nitrobenzylideneamino)-3-cephem-4-carboxylate.

EXAMPLE 99 p-Nitrobenzyl d,1-7β-amino-3-methoxymethyl-3-cephem-4-carboxylate

A mixture of 2,4-dinitrophenylhydraxine (0.482 g) and p-toluenesulfonic acid monohydrate (0.434 g) in ethanol (65 ml) is stirred at room temperature for 45 minutes, then treated with a solution of p-nitrobenzyl-3-methoxymethyl-7-(p-nitrobenzylideneamino)-3-cephem-4-carboxylate (1.166 g, mixture of 7α- and 7β-isomers) in chloroform (5 ml). After having been stirred for 30 minutes at room temperature, the reaction mixture is filtered and the filtrate is evaporated under reduced pressure. The residue is treated with water (30 ml) and 1 M dipotassium hydrogen phosphate (4.6 ml) and extracted with ether. The combined extracts are dried over magnesium sulfate, filtered, and evaporated to afford a mixture of p-nitrobenzyl d,1-7α-amino-3-methoxymethyl-3-cephem-4-carboxylate and p-nitrobenzyl d,1-7β-amino-3-methoxymethyl-3-cephem-4-carboxylate.

EXAMPLE 100 p-Nitrobenzyl d,1-3-methoxymethyl-7α-(D-α-azido-phenylacetamido)-3-cephem-4-carboxylate and p-Nitrobenzyl d,1-3-methoxymethyl-7β-(D-α-azido-phenylacetamido)-3-cephem-4-carboxylate A solution of p-nitrobenzyl d,1-7-amino-3-methoxymethyl-3-cephem-4-carboxylate (0.76 g, mixture of 7α-and 7β-isomers) in methylene chloride (20 ml) at 0° is treated with a D-α-azido-phenylacetyl chloride (0.40 g) and pyridine (0.8 ml). After 15 minutes stirring at 0° the mixture is washed with cold water, 1% aqueous phosphoric acid, 5% aqueous sodium bicarbonate, and water. The solution is dried over magnesium sulfate, filtered, and concentrated in vacuo to an oil. This is chromatographed on silica gel yielding p-nitrobenzyl d,1-3-methoxymethyl-7α-(D-α-azido-phenylacetamido)-3-cephem-4-carboxylate and p-nitrobenzyl d,1-3-methoxymethyl-7β-(D-α-azido-phenylacetamido)-3-cephem-4-carboxylate.

EXAMPLE 101 d,1-7β-(D-α-amino-phenylacetamido)-3-methoxymethyl-3-cephem-4-carboxylic acid

A mixture of p-nitrobenzyl d,1-7β-(D-α-azido-phenylacetamido)-3-methoxymethyl-3-cephem-4-carboxylate (0.27 g), 10% palladium on carbon (0.30 g) and acetic acid (15 mls) is hydrogenated at 40 psi for 1 hour. The catalyst is filtered and washed with water (60 ml). The filtrate is washed with three portions of ethyl acetate, pumped at high vacuum to remove dissolved ethyl acetate, and lyophilized to affored d,1-7β-(D-α-amino-phenylacetamido)-3-methoxymethyl-3-cephem-4-carboxylic acid.

EXAMPLE 102

Dimethyl N-benzyl-aminomethylphosphonate hydrochloride

A mixture of dimethyl phosphite (55.0 g) and 1,3,5-tribenzyl-sym-hexahydrotriazene (59.6 g) is heated with stirring for 6 hours at 100°. A drying tube is used to protect the mixture from moisture. The reaction mixture is allowed to come to room temperature overnight. The mixture, dissolved in ether, is cooled in an ice-bath and treated with anhydrous hydrogen chloride. The resulting precipitate of dimethyl N-benzyl-aminomethylphosphonate hydrochloride is collected, washed with ether, and dried.

EXAMPLE 103

Dimethyl aminomethylphosphonate hydrochloride

Dimethyl N-benzyl-aminomethylphosphonate hydrochloride (80.0 g) in methanol (800 ml) is hydrogenated at 40 psi with 10% palladium on powdered charcoal (4.0 g). The catalyst is removed by filtration through a pad of super cel. Evaporation of the methanolic filtrate gives a clear residue which is taken up in benzene. Removal of the benzene in vacuo affords crystalline dimethyl aminomethylphosphonate hydrochloride.

EXAMPLE 104

Dimethyl aminomethylphosphonate

Dimethyl aminomethylphosphonate hydrochloride (17.6 g) is stirred in chloroform (100 ml) at 0°. Ammonia is bubbled through the mixture for 5 minutes. The ammonium chloride is filtered off and washed with a small portion of chloroform. The combined filtrate and washings are dried briefly over magnesium sulfate, filtered, and evaporated in vacuo to give dimethyl aminomethylphosphonate.

EXAMPLE 105

Dimethyl N-benzylidene-aminomethylphosphonate

Benzaldehyde (10.6 g) is added dropwise with stirring to ice-cold dimethyl aminomethylphosphonate (13.9 g). The resulting mixture is diluted with benzene (200 ml) and treated with magnesium sulfate (20 g). After stirring 30 minutes at room temperature, the mixture is filtered and the salts are washed with benzene. Evaporation of the filtrate under reduced pressure leaves dimethyl N-benzylideneaminomethylphosphonate.

EXAMPLE 106 p-Methoxybenzyl N-benzylidene-α-amino-dimethylphosphonoacetate

Dimethyl N-benzylidene-aminomethylphosphonate (22.72 g) is dissolved in anhydrous tetrahydrofuran (500 ml) under nitrogen. The solution is cooled to −78°, and phenyllithium (45 ml of a 2.3 M solution in benzene-ether) is added with stirring. The solution is stirred an additional 15 minutes at −78°. and then treated dropwise over 45 minutes with p-methoxybenzyl chloroformate (10.03 g) in tetrahydrofuran (100 ml). After stirring for 2 hours at −78°, the reaction mixture is allowed to warm to 0° over 30 minutes. The solvent is evaporated in vacuo and the residue is partitioned between ether (500 ml) and 0.5 M pH 3 phosphate buffer (100 ml). The ether portion is washed with water and saturated brine, dried over magnesium sulfate, filtered, and evaporated in vacuo to dryness. Chromatography of the residue on silica gel affords p-methoxybenzyl N-benzylidene-α-amino-dimethylphosphonoacetate.

EXAMPLE 107 p-Methoxybenzyl α-amino-dimethylphosphonoacetate p-Methoxybenzyl N-benzylidene-α-amino-dimethylphosphonoacetate (9.78 g) in ether (50 ml) is added over 20 minutes to a stirring solution of p-toluenesulfonic acid monohydrate (4.76 g) in ether (150 ml). Cyclohexane (100 ml) is added and the solvents are decanted off. The residue is washed with more 2:1 ether-cyclohexane, which is again decanted off. The residue is partitioned between methylene chloride and 1 M dipotassium hydrogen phosphate (50 ml). The organic portion is separated, washed with water, dried, and evaporated in vacuo to give p-methoxybenzyl α-aminodimethylphosphonoacetate.

EXAMPLE 108 p-Methoxybenzyl α-thioformamido-dimethylphosphonoacetate

Hydrogen sulfide (0.75 g) is passed into a cold (ice-bath) solution of p-methoxybenzyl α-amino-dimethyl-phosphonoacetate (6.06 g) in anhydrous methanol (5 ml). Hydrogen cyanide (0.53 g) is added and the ice-bath is removed. After standing overnight, the reaction mixture is added to water (50 ml) and extracted with ether (3 × 20 ml). The combined extracts are dried with magnesium sulfate, filtered, and evaporated in vacuo to dryness. The residue is chromatographed on silicon gel, affording p-methoxybenzyl α-thioformamido-dimethylphosphonoacetate.

EXAMPLE 109 p-Methoxybenzyl 5-(N,N-di-p-methoxybenzyl)carbamoyloxymethyl-6H-1,3-thiazine-4-carboxylate A mixture of p-methoxybenzyl α-thioformamidodimethylphosphonoacetate (3.04 g), acetone (50 ml), 1-chloro3-(N,N-di-p-methoxybenzyl)carbamoyloxy-2-propanone (3.62 g), and powdered potassium carbonate (3.64 g) is stirred at room temperatue in a stoppered flask for 5 hours. The mixture is filtered and the filtrate is evaporated in vacuo. The residue is taken up in carbon tetrachloride (200 ml), washed twice with phosphate buffer (30 ml 1 M dipotassium hydrogen phosphate + 70 ml water) and saturated brine (100 ml.), dried over magnesium sulfate, and filtered. Evaporation of the filtrate gives crude p-methoxybenzyl 5-(N,N-di-p-methoxybenzyl)carbamoyloxymethyl-6H-1,3-thiazine-4-carboxylate as a golden oil: ir (CCl$_4$) 5.87, 6.22, 6.63, 6.85, 7.68, 8.02, 8.51, 8.96, and 9.60 μ; nmr (CDCl$_3$) τ 6.82 (s, 2, SCH$_2$), 6.20 (s, 9, OCH$_3$), 5.65 (brs, 4, NCH$_2$), 4.74 (s, 4, OCH$_2$), 3.3–2.5 (m, 12, ArH) and 1.63 (s,1,CH=N).

1-Chloro-3-(N,N-di-p-methoxybenzyl)carbamoyloxy-2-propanone is prepared as described in the following sequence of examples.

STEP 1. Methyl (N,N-di-p-methoxybenzyl)carbamoyloxyacetate

A solution of methyl glycolate (6.15 g) and triethylamine (9.6 ml) in dry benzene (35 ml) is added dropwise over 30 minutes to an ice-cold, stirring solution of phosgene in benzene (57 g of a 12.5% solution). After warming to room temperature over 30 minutes, the mixture is purged with nitrogen to remove excess phosgene. The mixture is again cooled in an ice-bath and stirred while a solution of di-p-methoxybenzylamine (17.58 g) and triethylamine (9.6 ml) in dry benzene (70 ml) is added dropwise over 45 minutes. The cooling bath is removed and the mixture is stirred at room temperature overnight. Triethylamine hydrochloride is filtered off and washed with benzene. The filtrate is washed with water, 0.5 M pH 2 phosphate buffer, water, and saturated brine, dried with magnesium sulfate, filtered, and evaporated in vacuo to a semi-solid. Recrystallization of the crude product from methanol gives methyl (N,N-di-p-methoxybenzyl)carbamoyloxyacetate as a white powder: m.p. 66°–67°; ir (CHCl$_3$) 5.67, 5.87, 6.22, 6.66, 6.87, 6.99, 8.90, and 9.72 μ; nmr (CDCl$_3$) τ6.20 (s, 9, OCH$_3$), 5.63 (s, 4, NCH$_2$), 5.28 (s, 2, OCH$_2$), and 3.17, 2.82 (dd, 8, J=9Hz, ArH).

STEP 2: (N,N-di-p-Methoxybenzyl)carbamoyloxyacetic acid

A mixture of methyl (N,N-di-p-methoxybenzyl)carbamoyloxyacetate (12.66 g), methanol (300 ml), and 1 N aqueous sodium hydroxide (38 ml) is stirred at room temperature for 20 hours. The solvent is removed in vacuo. The residue is taken up in water (300 ml) and filtered to remove a small amount of insoluble material. The aqueous filtrate is layered with ethyl acetate (200 ml) and acidified to pH 2.5 with concentrated hydrochloric acid. The aqueous phase is separated and extracted with an additional portion of ethyl acetate. The combined organic extracts are dried over magnesium sulfate, filtered, and evaported in vacuo to yield (N,N-di-p-methoxybenzyl)carbamoyloxyacetic acid as a white powder: m.p., 122°–123°; ir (CHCl$_3$) 5.74 (sh), 5.87, 6.19, 6.61, 6.82, 8.83, and 9.64 μ; nmr (CDCl$_3$) τ6.20 (s, 6, OCH$_3$), 5.60 (s, 4, NCH$_2$), 5.20 (s, 2, OCH$_2$), 3.12, 2.77 (dd, 8, J=9Hz, ArH), and 0.07 (s, 1, OH).

STEP 3. (N,N-di-p-methoxybenzyl)carbamoyloxyacetyl chloride

A suspension of (N,N-di-p-methoxybenzyl)carbamoyloxyacetic acid (9.5 g) in anhydrous benzene (300 ml) is stirred and cooled in an ice-path. Oxalyl chloride (4.47 ml) and dimethylformamide (0.45 ml) are added, and the mixture is stirred for 1 hour at 5° and 1 hour at room temperature. The resulting solution is washed with ice-cold brine, dried over magnesium sulfate, filtered, and evaporated in vacuo to yield (N,N-di-p-methoxybenzyl)carbamoyloxyacetyl chloride as a clear oil: ir (neat) 5.53, 5.85, 6.20, 6.62, 6.85, 6.97, 8.02, 8.51, 8.87, and 9.67 μ; nmr (CDCl$_3$)τ6.19 (s, 6, OCH$_3$), 5.62 (s, 4, NCH$_2$), 4.98 (s, 2, OCH$_2$), and 3.10, 2.80 (dd, 8, J=9Hz, ArH).

STEP 4: 1-Chloro-3-(N,N-di-p-methoxybenzyl)carbamoyloxy-2-propanone (N,N-di-p-Methoxybenzyl)carbamoyloxyacetyl chloride (10.4 g) in anhydrous ether (125 ml) is added dropwise over 45 minutes to an ice-cold, stirring solution of triethylamine (3.7 ml) and excess diazomethane (from 15 g of N-methyl-N-nitrosourea) in ether (150 ml). The mixture is stirred an additional 1 hour in the cold, and then purged with nitrogen to expel excess diazomethane. The mixture is filtered and the filtarate is evaporated in vacuo to afford 1-diazo-3-(N,N-di-p-methoxybenzyl)carbamoyloxy-2-propanone as a yellow oil: ir (neat) 4.72, 5.86, 6.04, 6.62, 6.83, 7.32, 8.0, 8.50, 8.91, and 9.64 μ; nmr (CDCl$_3$) τ 6.20 (s, 6, OCH$_3$), 5.60 (s, 4, NCH$_2$), 5.30 (s, 2, OCH$_2$), 4.80 (s, 1, CHN$_2$), and 3.12, 2.78 (dd, 8, J=9Hz, ArH).

The above diazoketone in ether (300 ml) is cooled in an ice-bath and treated with anhydrous hydrogen chloride over 5 minutes. The resulting mixture is washed with cold water, cold 5% aqueous sodium bicarbonate, and saturated brine. Evaporation of the ether, after drying over magnesium sulfate, gives a white solid. Recrystalliztion of this material from ether-petroleum ether affords 1-cholro-3-(N,N-di-p-methoxybenzyl)carbamoyloxy-2-propanone as off-white flakes: m.p. 78–80°; ir (CHCl$_3$) 5.73, 5.88, 6.20, 6.63, 6.83, and 9.64 μ; nmr (CDCl$_3$) τ 6.20 (s, 6, OCH$_3$), 5.87 (s, 2, CH$_2$Cl), 5.62 (s, 4, NCH$_2$), 5.03 (s, 2, OCH$_2$), and 3.13, 2.80 (dd, 8, J=9Hz, ArH).

EXAMPLE 110 p-Methoxybenzyl d,1-7a-azido-3-(N,N-di-p-methoxybenzyl)carbamoyloxymethyl-3-cephem-4-carboxylate A solution of p-methoxybenzyl 5-(N,N-di-p-methoxybenzyl)carbamoyloxymethyl-6H-1,3-thiazine-4-carboxylate (6.5 g) in anhydrous methylene chloride (110 ml) is stirred under nitrogen with ice-bath cooling. Triethylamine (1.95 ml) is added all at once, followed by the dropwise addition of azidoacetyl chloride (1.22 ml) in methylene chloride (85 ml) over 90 minutes. The resulting dark solution is washed with water (4 × 100 ml), dried with magnesium sulfate, filtered, and evaporated in vacuo to a dark oil. This material is chromatographed on silica gel. Elution of the products with 5% ethyl acetate in benzene affords p-methoxybenzyl d,1-7a-azido-3-(N,N-di-p-methoxybenzyl)carbamoyloxymethy-3-cephem-4-carboxylate as a gum: ir (CHCl$_3$) 4.73, 5.60, 5.81, 5.91, 6.20, 6.64, 6.85, 7.68, 8.02, 8.94, and 9.64 μ; nmr (CDCl$_3$) τ 6.94, 6.58 (dd, 2, J=18Hz, SCH$_2$), 6.20 (s, 9, OCH$_3$), 5.67 (br s, 4, NCH$_2$), 5.47 (m, 2, H6 and H7), 5.17, 4.85 (dd, 2, J=13Hz, NCO$_2$CH$_2$), 4.77 (m, 2, OCH$_2$Ar) and 3.3–2.5 (m, 12, ArH).

EXAMPLE 111 p-Methoxybenzyl d,1-7α-amino-3-(N,N-di-p-methoxybenzyl)carbamoyloxymethyl-3-cepham-4-carboxylate A mixture of p-methoxybenzyl d,1-7α-azido-3-(N,N-di-p-methoxybenzyl)carbamoyloxymethyl-3-cephem-4-carboxylate (3.00 g), platinum oxide (1.50 g), and benzene (150 ml) is hydrogenated at 40 psi for 3 hours. The mixture is evaporated in vacuo to a black oil. This material is taken up in ethyl acetate and filtered through a pad of 1:1 super cel-silica gel G. The filtrate is dried over magnesium sulfate, filtered, and evaporated in vacuo affording p-methoxybenzyl d,17α-amino-3-(N,N-di-p-methoxybenzyl)carbamoyloxymethyl-3-cephem-4-carboxylate: ir (CHCl$_3$) 2.94, 5.62, 5.79, 5.81, 6.20, 6.62, 8.03, 8.51, 8.97, and 9.66 μ.

EXAMPLE 112 p-Methoxybenzyl d,1-7α-(p-nitrobenzylideneamino)-3-(N,N-di-p-methoxybenzyl)carbamoyloxymethyl-3-cephem-4-carboxylate A mixture of p-methoxybenzyl d,1-7α-amino-3-(N,N-di-p-methoxybenzyl)carbamoyloxymethyl-3-cephem-4-carboxylate (2.35 g), p-nitrobenzaldehyde (0.56 g), magnesium sulfate (10.0 g), and methylene chloride (100 ml) is stirred at room temperature for 15 hours. The mixture is filtered and the filtrate is evaporated in vacuo to a gum. This material is dissolved in benzene and the solvent evaporated to yield p-methoxybenzyl d,1-7α-(p-nitrobenzylideneamino)-3-(N,N-di-p-methoxybenzyl)carbamoyloxymethyl-3-cephem-4-carboxylate.

EXAMPLE 113 p-Methoxybenzyl d,1-7β-(p-nitrobenzylideneamino)-3-(N,N-di-p-methoxybenzyl)carbamoyloxymethyl-3-cephem-4-carboxylate A solution of p-methoxybenzyl d,1-7α-(p-nitrobenzylideneamino)-3-(N,N-di-p-methoxybenzyl)carbamoyloxymethyl-3-cephem-4-carboxylate (0.77 g) in anhydrous tetrahydrofuran (15 ml) is cooled to −78° under nitrogen. Phenyllithium (0.44 ml of a 2.3 M solution in 7:3 benzene-ether) is added rapidly with stirring. Dimethylformamide (19 ml) is then added dropwise over a period of 5 minutes. After stirring one more minutes at −78°, the reaction mixture is quenched by addition of water (0.18 ml) and acetic acid (0.14 ml) in tetrahydrofuran (10 ml). The mixture is allowed to warm to room temperature. Benzene (250 ml) is added and the solution is washed with water (6 × 100 ml). The second wash is acidified with pH 3 phosphate buffer and the fifth basified with pH 9 phosphate buffer. The benzene solution is dried with magnesium sulfate, filtered, and evaporated in vacuo to give a mixture of p-methoxybenzyl d,1-7α-(p-nitrobenzylideneamino)-3-(N,N-di-pmethoxybenzyl)carbamoyloxymethyl-3-cephem-4-carboxylate and p-methoxybenzyl d,1 -7β-(p-nitrobenzylideneamino)-3-(N,N-di-p-methoxybenzyl)carbamoyloxymethyl-3-cephem-4-carboxylate.

EXAMPLE 114 p-Methoxybenzyl d,1-7β-amino-3-(N,N-di-p-methoxybenzyl)-carbamoyloxymethyl-3-cephem-4-carboxylate A mixture of p-toluenesulfonic acid monohydrate (0.169 g) and 2,4-dinitrophenylhydrazine (0.175 g) in ethanol (25 ml) is stirred at room temperature for 45 minutes. p-Methoxybenzyl d,1-7-(p-nitrobenzylideneamino)-3-(N,N-di-p-methoxybenzyl)carbamoyloxymethyl-3-cephem-4-carboxylate (0.675 g, mixture of 7α- and 7β-isomers) in chloroform (5 ml) is added and the resulting mixture is stirred at room temperature for 30 minutes. The mixture is filtered and the filtrate is evaporated in vacuo. The residue is treated with 1 M dipotassium hydrogen phosphate (2 ml) and water (13 ml) and extracted with ether (3 × 20 ml). The ethereal extracts are washed with water and saturated brine, dried with magnesium sulfate, filtered, and evaporated in vacuo to yield a mixture of p-methoxybenzyl d,1-7α-amino-3-(N,N-di-p-methoxybenzyl)carbamoyloxymethyl-3-cephem-4-carboxylate and p-methoxybenzyl d,1-7β-amino-3-(N,N-di-p-methoxybenzyl)carbamoyloxymethyl-3-cephem-4-carboxylate.

EXAMPLE 115 p-Methoxybenzyl d,1-7α-(2-thienylacetamido)-3-(N,N-di-p-methoxybenzyl)carbamoyloxymethyl-3-cephem-4-carboxylate and p-methoxybenzyl d, 1-7β-(2-thienylacetamido)-3-(N,N-di-p-methoxybenzyl)carbamoyloxymethyl-3-cephem-4-carboxylate An ice-cold, stirring solution of p-methoxybenzyl d,1-7-amino-3-(N,N-di-p-methoxybenzyl)carbamoyloxymethyl-3-cephem-4-carboxylate (0.538 g, mixture of 7α- and 7β-isomers) in anhydrous methylene chloride (10 ml) is treated with pyridine (0.30 ml) and 2-thienylacetyl chloride (0.11 ml). After stirring for 15 minutes at 0°, the reaction mixture is diluted with benzene (50 ml). The benzene solution is washed with cold 1% aqueous phosphoric acid, cold 5% aqueous sodium bicarbonate, and water, dried with magnesium sulfate, and filtered. Evaporation of the solvents in vacuo leaves an oily residue. This material is purified by chromatography on silica gel, affording p-methoxybenzyl d,1-7α-(2-thienylacetamido)-3-(N,N-di-p-methoxybenzyl)carbamoyloxymethyl-3-cephem-4-carboxylate and p-methoxybenzyl d,1-7β-(2-thienylacetamido)-3-(N,N-di-p-methoxybenzyl)carbamoyloxymethyl-3-cephem-4-carboxylate.

EXAMPLE 116 d,1-7β-(2-Thienylacetamido)-3-carbamoyloxymethyl-3-cephem-4-carboxylic acid p-Methoxybenzyl d,1-7β-(2-thienylacetamido)-3-(N,N-di-p-methoxybenzyl)carbamoyloxymethyl-3-cephem-4-carboxylate (0.254 g) is taken up in anisole (2.5 ml) and treated with trifluoroacetic acid (12.5 ml). The resulting solution is kept at room temperature for 30 minutes, and then evaporated in vacuo to dryness. The residue is taken up in aqueous sodium bicarbonate and extracted with methylene chloride. The aqueous phase is acidified to pH 2.5 and extracted with ethyl acetate. Evaporation of the ethyl acetate, after drying over magnesium sulfate, affords d,1-7β-(2-thienylacetamido)-3-carbamoyloxymethyl-3-cephem-4-carboxylic acid.

EXAMPLE 117 p-Methoxybenzyl d,1-7-azido-7-bromo-3-(N,N-di-p-methoxybenzyl)carbamoyloxymethyl-3-cephem-4-carboxylate A solution of p-methoxybenzyl d,1-7-amino-3-(N,N-di-p-methoxybenzyl)carbamoyloxymethyl-3-cephem-4-carboxylate (0.634 g) in methylene chloride (25 ml) is treated with water (25 ml) and sodium nitrite (0.138 g). The mixture is stirred at 0° under nitrogen. Sulfuric acid (0.75 ml of a 2 N solution) is added and the mixture is stirred at 0° for 45 minutes. The methylene chloride layer is separated, dried with magnesium sulfate, filtered, and concentrated in vacuo to 5 ml. This solution is cooled to −20° under nitrogen and treated with triethylammonium azide in methylene chloride (5 ml of a 0.3 N solution) and bromine azide in methylene chloride (5 ml of a 0.3 N solution). The resulting solution is stirred at −20° for 10 minutes and then allowed to warm to 0°. Aqueous dipotassium hydrogen phosphate is added and the layers are separated. The methylene chloride portion is dried over magnesium sulfate, filtered, and evaporated in vacuo. Chromatography of the residue on silica gel affords p-methoxybenzyl d,1-7-azido-7-bromo-3-(N,N-di-p-methoxybenzyl)carbamoyloxymethyl-3-cephem-4-carboxylate.

EXAMPLE 118 p-Methoxybenzyl d,1-7β-azido-7-methoxy-3-(N,N-di-p-methoxybenzyl)-carbamoyloxymethyl-3-cephem-4-carboxylate p-Methoxybenzyl d,1-7-azido-7-bromo-3-(N,N-di-p-methoxybenzyl)carbamoyloxymethyl-3-cephem-4-carboxylate (0.44 g) in anhydrous methanol (20 ml) is treated with pyridine (0.05 ml) and silver tetrafluoroborate (0.12 g). The resulting mixture is stirred for 2.5 hours at room temperature and then evaporated in vacuo to dryness. The residue is taken up in methylene chloride (10 ml) and filtered. The filtrate is washed with 5% aqueous sodium bicarbonate and saturated brine, dried over MgSO₄, filtered, and evaporated in vacuo to afford p-methoxybenzyl d,1-7β-azido-7-methoxy-3-(N,N-di-p-methoxybenzyl)carbamoyloxymethyl-3-cephem-4-carboxylate.

EXAMPLE 119 p-Methoxybenzyl d,1-7β-amino-7-methoxy-3-(N,N-di-p-methoxybenzyl)carbamoyloxymethyl-3-cephem-4-carboxylate A mixture of p-methoxybenzyl d,1-7β-azido-7-methoxy-3-(N,N-di-p-methoxybenzyl)carbamoyloxymethyl-3-cephem-4-carboxylate (0.40 g) and platinum oxide (0.40 g) in dioxane (40 ml) is hydrogenated at 40 psi for 1 hour.. Additional catalyst (0.40 g) is added and the hydrogenation is continued for 2 more hours. The dioxane is evaporated in vacuo. The residue is taken up in ethyl acetate and the mixture is filtered through a pad of silica gel. The filtrate is evaporated in vacuo to yield p-methoxybenzyl d,1-7β-amino-7-methoxy-3-(N,N-di-p-methoxybenzyl)carbamoyloxymethyl-3-cephem-4-carboxylate.

EXAMPLE 120 p-Methoxybenzyl d,1-7α-methoxy-7-(2-thienylacetamido)-3-(N,N-di-p-methoxybenzyl)carbamoyloxymethyl-3-cephem-4-carboxylate p-Methoxybenzyl d,1-7β-amino-7-methoxy-3-(N,N-di-p-methoxybenzyl)carbamoyloxymethyl-3-cephem-4-carboxylate (0.33 g) is dissolved in anhydrous methylene chloride (4 ml), and the solution is cooled to 0° under nitrogen. Pyridine (0.20 ml) is added followed by a solution of 2-thienylacetyl chloride (0.08 g) is methylene chloride (2 ml). After stirring at 0° for 15 minutes, the reaction mixture is diluted with benzene (40 ml). The solution is washed with dilute aqueous phosphoric acid, 5% aqueous sodium bicarbonate, and water, dried over magnesium sulfate, and evaporated in vacuo to an oil. This material is purified by column chromatography on silica gel, affording p-methoxybenzyl d,1-7α-methoxy-7-(2-thienylacetamido)-3-(N,N-di-p-methoxybenzyl)carbamoyloxymethyl-3-cephem-4-carboxylate. d,1-7α-Methoxy-7-(2-thienylacetamido)-3-carbamoyloxymethyl-3-cephem-4-carboxylic acid p-Methoxybenzyl d,1-7α-methoxy-7-(2-thienylacetamido)-3-(N,N-di-p-methoxybenzyl)carbamoyloxymethyl-3-cephem-4-carboxylate (0.30 g) is dissolved in a mixture of anisole (3.0 ml) and trifluoroacetic acid (15.0 ml). The solution is kept at room temperature for 30 minutes, and then evaporated in vacuo to dryness. The residue is taken up in water (10 ml) containing sodium bicarbonate (0.35 g), and the solution is extracted with methylene chloride. The aqueous phase is layered with ethyl acetate and the pH adjusted to 2.5 with 6 N hydrochloric acid. The ethyl acetate layer is separated, dried with magnesium sulfate, and evaporated in vacuo to yield d,1-7α-methoxy-7-(2-thienylacetamido)-3-carbamoyloxymethyl-3-cephem-4-carboxylic acid.

EXAMPLE 121 d,1-7α-Methoxy-7-(2-thienylacetamido)-3-carbamoyloxymethyl-3-cephem-4-carboxylic acid p-Methoxybenzyl d,1-7α-methoxy-7-(2-thienylacetamido)-3-(N,N-di-p-methoxybenzyl)carbamoyloxymethyl-3-cephem-4-carboxylate (0.30 g) is dissolved in a mixture of anisole (3.0 ml) and trifluoroacetic acid (15.0 ml). The solution is kept at room temperature for 30 minutes, and then evaporated in vacuo to dryness. The residue is taken up in water (10 ml) containing sodium bicarbonate (0.35 g), and the solution is extracted with methylene chloride. The aqueous phase is layered with ethyl acetate and the pH adjusted to 2.5 with 6 N hydrochloric acid. The ethyl acetate layer is separated, dried with magnesium sulfate, and evaporated in vacuo to yield d,1-7α-methoxy-7-(2-thienylacetamido)-3-carbamoyloxymethyl-3-cephem-4-carboxylic acid.

EXAMPLE 122 p-Methoxybenzyl d,1-7-azido-7-bromo-3-acetoxymethyl-3-cephem-4-carboxylate p-Methoxybenzyl d,1-7-amino-3-acetoxymethyl-3-cephem-4-carboxylate (0.79 g, mixture of 7α- and 7β-isomers) is dissolved in methylene chloride (50 ml) and treated with water (50 ml) and sodium nitrite (0.28 g). The mixture is stirred under nitrogen with ice-bath cooling. Sulfuric acid (1.5 ml of a 2 N solution) is added, and the mixture is stirred for 50 minutes in the cold. The methylene chloride layer is separated, dried over magnesium sulfate, filtered, and concentrated in vacuo to 10 ml. To this solution of crude p-methoxybenzyl d,1-7-diazo-3-acetoxymethyl-3-cephem-4-carboxylate, cooled to −20° under nitrogen, is added triethylammonium azide in methylene chloride (10 ml of a 0.3 N solution) in one portion, followed immediately by bromine azide in methylene chloride (10 ml of a 0.3 N solution) over 1-2 minutes. The resulting mixture is stirred at −15° for 5 minutes and then allowed to warm to 0°. Aqueous dipotassium hydrogen phosphate is added and the layers are separated. The methylene chloride portion is dried with magnesium sulfate, filtered, and evaporated in vacuo. The residue is chromatographed on silica gel, affording p-methoxybenzyl d,1-7-azido-7-bromo-3-acetoxymethyl-3-cephem-4-carboxylate.

EXAMPLE 123 p-Methoxybenzyl d,1-7β-azido-7-methoxy-3-acetoxymethyl-3-cephem-4-carboxylate

Pyridine (0.08 ml) and silver tetrafluoroborate (0.195 g) are added to a solution of p-methoxybenzyl d,1-7-azido-7-bromo-3-acetoxymethyl-3-cephem-4-carboxylate (0.497 g) in anhydrous methanol (35 ml). The resulting mixture is stirred for 2.5 hours at room temperature and then evaporated in vacuo to dryness. The residue is taken up in methylene chloride (20 ml) and filtered. The filtrate is washed with 5% aqueous sodium bicarbonate (10 ml) and saturated brine, dried over magnesium sulfate, filtered, and evaporated in vacuo. Crystallization of the residue affords p-methoxybenzyl d,1-7β-azido-7-methoxy-3-acetoxymethyl-3-cephem-4-carboxylate.

EXAMPLE 124 p-Methoxybenzyl d,1-7β-amino-7-methoxy-3-acetoxymethyl-3-cephem-4-carboxylate p-Methoxybenzyl d,1-7β-azido-7-methoxy-3-acetoxymethyl-3-cephem-4-carboxylate (0.20 g) is hydrogenated in dioxane (20 ml) for 1 hours with platinum oxide (0.20 g), then for 2 more hours with additional platinum oxide (0.20 g). The dioxane is removed in vacuo. The residue is taken up in ethyl acetate and filtered through a pad of 1:1 silica gel G-super cel. Removal of the ethyl acetate in vacuo affords p-methoxybenzyl d,1-7β-amino-7-methoxy-3-acetoxymethyl-3-cephem-4-carboxylate.

EXAMPLE 125 p-Methoxybenzyl d,1-7α-methoxy-7-(2-thienylacetamido)-3-acetoxymethyl-3-cephem-4-carboxylate A solutin of p-methoxybenzyl d,1-7β-amino-7-methoxy-3-acetoxymethyl-3-cephem-4-carboxylate (0.12 g) in methylene chloride (4 ml) is cooled (ice-bath) and stirred under nitrogen. Pyridien (0.12 ml) and 2-thienylacetyl chloride (0.035 ml) are added. The reaction mixture is stirred at 0° for 15 minutes, then diluted with benzene. The solution is washed with 1% aqueous phosphoric acid, 5% aqueous sodium bicarbonate, and water, dried with magnesium sulfate, and filtered. Evaporation of the solvents in vacuo leaves p-methoxybenzyl d,1-7α-methoxy-7-(2-thienylacetamido)-3-acetoxymethyl-3-cephem-4-carboxylate.

EXAMPLE 126 p-Methoxybenzyl d,1-7α-methoxy-7-(p-nitrobenzylideneamino)-3-acetoxymethyl-3-cephem-4-carboxylate p-Methoxybenzyl d,1-7α-(p-nitrobenzylideneamino)-3-acetoxymethyl-3-cephem-4-carboxylate (1.05 g) is dissolved in anhydrous tetrahydrofuran (25 ml) under nitrogen. The solution is cooled to −78° and phenyllithium (0.87 ml of a 2.3 M solution in benzene-ether) is added with stirring over 1 minute. After stirring an additional minute at −78°, the solution is treated with N-bromosuccinimide (0.366 g) in tetrahydroduran (10 ml). The reaction mixture is kept at −78° for 2 minutes and then it is allowed to warm to room temperature. The solvent is removed in vacuo until the volume is ca. 10 ml. The residue is diluted with methylene chloride (100 ml) and the solution is washed twice with pH 7 phosphate buffer. The organic portion is dried with magnesium sulfate, filtered, and evaporated in vacuo to 20 ml. This solution of bromo-Schiff base is added dropwise over 20 minutes to a stirring suspension of silver oxide (0.93 g) in anhydrous methanol (40 ml). The resulting mixture is stirred for another 60 minutes at room temperature. The silver salts are filtered off and the filtrate is evaporated to dryness. The residue is taken up in methylene chloride and the solution is washed twice with pH 7 phosphate buffer, dried over magnesium sulfate, filtered, and concentrated in vacuo. Chromatography of the residue on silica gel affords p-methoxybenzyl d,1-7α-methoxy-7-(p-nitrobenzylideneamino)-3-acetoxymethyl-3-cephem-4-carboxylate.

EXAMPLE 127 p-Methoxybenzyl d,1-7α-methoxy-7-(2-thienylacetamido)-3-acetoxymethyl-3-cephem-4-carboxylate A solution of p-methoxybenzyl d,1-7α-methoxy-7-(p-nitrobenzylideneamino)-3-acetoxymethyl-3-cephem-4-carboxylate (0.67 g) in tetrahydrofuran (25 ml) is diluted with water (4 ml) and treated with palladium chloride (0.11 g). The mixture is stirred at room temperature for 4 hours, then evaporated in vacuo to dryness. The residue is taken up in methylene chloride (50 ml), dried with magnesium sulfate, filtered, and concentrated in vacuo to 15 ml. This solution, after being cooled to 0°, is treated with pyridine(0.70 ml) and 2-thienylacetyl chloride (0.23 g). The reaction mixture is stirred at 0° for 15 minutes and then allowed to warm up in the next 15 minutes. The reaction mixture is diluted with methylene chloride and washed with pH 2 phosphate buffer and pH 7 phosphate buffer. The organic portion is dried with magnesium sulfate, filtered, and evaporated in vacuo. Chromatography of the residue on silica gel affords p-methoxybenzyl d,1-7α-methoxy-7-(2-thienylacetamido)-3-acetoxymethyl-3-cephem-4-carboxylate.

EXAMPLE 128

Sodium d,1-7α-methoxy-7-(2-thienylacetamido)-3-acetoxymethyl-3-cephem-4-carboxylate p-Methoxybenzyl d,1-7α-methoxy-7-(2-thienylacetamido)-3-acetoxymethyl-3-cephem-4-carboxylate (0.41 g) is treated at 0° for 5 minutes with anisol (0.6 ml) and trifluoroacetic acid (3.0 ml). The trifluoroacetic acid is removed at 0° in vacuo and the aisole at 30°. More anisole is added and evaporated as before. The residue is taken up in water (5 ml) containing sodium bicarbonate (0.07 g) and lyophilized to a powder. This is washed with ether and dried to give sodium d,1-7α-methoxy-7-(2-thienylacetamido)-3-acetoxymethyl-3-cephem-4-carboxylate.

EXAMPLE 129

Potassium d,1-7α-methoxy-7-(2-thienylacetamido)-3-hydroxymethyl-3-cephem-4-carboxylate Sodium d,1-7α-methoxy-7-(2-thienylacetamido)-3-acetoxymethyl-3-cephem-4-carboxylate (0.31 g) is dissolved in citrus acetyl esterase (8.5 ml). The solution is stirred in a water bath maintained at 30°, and the pH is kept at 6.6 by addition of 1 N sodium hydroxide. After 1 hour, additional enzyme solution (1.5 ml) is added. The pH is maintained at 6.6 until it remains constant for ca. 0.5 hour. After cooling to room temperature, the solution is treated with sodium chloride (3.0 g), layered with ethyl acetate (10 ml), and acidified to pH 2.1 with 6 N hydrochloric acid. The ethyl acetate portion is separated and washed with water. The organic phase is then layered with water (25 ml) and the pH is adjusted to 5.6 with 6 N potassium hydroxide. The aqueous phase is separated and lyophilized. Recrystallization of the residue from methanol-isopropanol affords potassium d,1-7α-methoxy-7-(2-thienylacetamido)-3-hydroxymethyl-3-cephem-4-carboxylate.

EXAMPLE 130 d,1-7α-Methyoxy-7-(2-thienylacetamido)-3-carbamoyloxymethyl-3-cephem-4-carboxylic acid Chlorosulfonyl isocyanate (0.15 ml) is added to an ice-cold suspension of potassium d,1-7α-methoxy-7-(2-thienylacetamido)-3-hydroxymethyl-3-cephem-4-carboxylate (0.20 g) in acetonitrile (5 ml). The resulting mixture is stirred in the cold for 90 minutes. Evaporation of the solvent leaves a residue which is taken up in ethyl acetate (10 ml) and water (10 ml). The pH of the aqueous layer is adjusted to 1.6 with 2.5 N hydrochloric acid and the mixture is stirred for 2.5 hours at room temperature. The pH is then adjusted to 8 with aqueous tripotassium phosphate. The aqueous phase is separated, acidified to pH 2.5 with hydrochloric acid, and extracted with ethyl acetate. The ethyl acetate solution, after drying over sodium sulfate, is evaporated in vacuo to give d,1-7α-methoxy-7-(2-thienylacetamido)-3-carbamoyloxymethyl-3-cephem-4-carboxylic acid.

EXAMPLE 131 p-Methoxybenzyl d,1-7β-azido-7-methyl-3-acetoxymethyl-3-cephem-4-carboxylate and p-methoxybenzyl d,1-7α-azido-7-methyl-3-acetoxymethyl-3-cephem-4-carboxylate A solution of p-methoxybenzyl 5-acetoxymethyl-6H-1,3-thiazine-4-carboxylate (0.67 g) and triethylamine (0.30 g) in anhydrous methylene chloride (15 ml) is cooled to 0° under nitrogen. A solution of 2azido-propionyl chloride (0.40 g) in anhydrous methylene chloride (10 ml) is added dropwise with stirring over a period of 2 hours. The resulting solution is stirred an additional 1 hour at 0° and 1 hour at room temperature. Methylene chloride (25 ml) is added and the solution is washed with water (4 × 25 ml) and saturated brine (25 ml). Evaporation of the solvent, after drying over magnesium sulfate, gives a dark oil. This material is purified by column chromatography on silica gel, affording p-methoxybenzyl d,1-7β-azido-7-methyl-3-acetoxymethyl-3-cephem-4-carboxylate and p-methoxybenzyl d,1-7α-azido-7-methyl-3-acetoxymethyl-3-cephem-4-carboxylate.

EXAMPLE 132 d,1-7β-(2-Thienylacetamido)-7-methyl-3-acetoxymethyl-3-cephem- 4-carboxylic acid p-Methoxybenzyl d,1-7β-azido-7-methyl-3-acetoxymethyl-3-cephem-4-carboxylate (0.050 g) in benzene (5 ml) is hydrogenated at 40 psi for 2 hours with platinum oxide (0.050 g). The catalyst is removed by filtration through a pad of super cel, which is washed with more benzene. The filtrate is evaporated in vacuo to yield p-methoxybenzyl d,1-7β-amino-7-methyl-3-acetoxymethyl-3-cephem-4-carboxylate.

80 Mg. of the above in 3 ml $CH_2Cl_2$ is treated with 0.1 ml pyridine and 27 mg 2-thienylacetyl chloride. After 5 minutes at 25°C., 25 ml benzene is added and the solution washed with aqueous pH 2 phosphate buffer, water, and aqueous pH 8 phosphate buffer. After drying with MgSO₄, filtration and evaporation of the solvent, the product is purified by chromatography on 5 g silica gel, eluting with 4:1 chloroformethyl acetate, affording p-methoxybenzyl dl-7β-(2-thienylacetamido)-7-methyl-3-acetoxymethyl-3-cephem-4-carboxylate.

The ester is treated for 4 minutes at 0° C. with 0.1 ml anisole and 0.5 ml trifluoroacetic acid. The TFA is pumped off at 0°C/0.1 mm, and the anisole at 30°C/0.1 mm. Anisole (1 ml) is added and pumped off to insure complete removal of TFA. The residue is treated with 1 ml water containing 13 mg NaHCO₃, washed twice with CH₂Cl₂ and lyophilized, affording dl-7β-(2-thienylacetamido)-7-methyl-3-acetoxymethyl-3-cephem-4-carboxylic acid.

EXAMPLE 133

Sodium dl-7α-methyl-7β-(2-thienylacetamido)cephalosporanate

A. p-Methoxybenzyl dl-7α-methyl-7β-amino cephalosporanate p-Methoxybenzyl dl-7α-methyl-7β-(p-nitrobenzylideneamino)cephalosporanate (303 mg) prepared as described below is treated with 109 mg 2,4-dinitrophenylhydrazine and 106 mg of p-toluenesulfonic acid hydrate in 10 ml ethanol for one-half hour. The mixture is filtered and the solids washed several times with ethanol. The filtrate is evaporated in vacuo, treated in pH 8 aqueous buffer and extracted twice with ether. The ether solution is dried with MgSO₄, filtered, evaporated, and the residue is chromatographed on 10 g silica gel, eluting with 4:1 chloroform-ethyl acetate. p-Methoxybenzyl dl-7α-methyl-7β-amino cephalosporanate is obtained.

p-Methoxybenzyl dl-7α-methyl-7β-(2-thienylacetamido) cephalosporanate p-Methoxybenzyl dl-7α-methyl-7β-amino cephalosporanate, 72 mg, in 3 ml CH₂Cl₂, is treated with 0.1 ml pyridine and 27 mg 2-thienylacetyl chloride. After 5 minutes at 25°C., 25 ml benzene is added and the solution washed with aqueous pH 2 phosphate buffer, water, and aqueous pH 8 phosphate buffer. After drying with MgSO₄, filtration and evaporation of the solvent, the product weighs 89 mg. It is purified by chromatography on 5 g silica gel, eluting with 4:1 chloroformethyl acetate, affording p-methoxybenzyl dl-7α-methyl-7β-(2-thienylacetamido)cephalosporanate.

C. Sodium dl-7α-methyl-7β-(2-thienylacetamido)cephalosporanate p-Methoxybenzyl dl-7α-methyl-7β-(2-thienylacetamido)cephalosporanate, 73 mg, is treated for 4 minutes at 0°C. with 0.1 ml anisole and 0.5 ml trifluoroacetic acid. The TFA is pumped off at 0°C/0.1 mm, and the anisole at 30°C/0.1 mm. Anisole (1 ml) is added and pumped off to insure complete removal of TFA. The residue is treated with 1 ml water containing 13 mg NaHCO₃, washed twice with CH₂Cl₂ and lyophilized, affording sodium dl-7α-methyl-7β-(2-thienylacetamido)cephalosporanate.

The starting material, p-methoxybenzyl dl-7α-methyl-7β-(p-nitrobenzylideneamino)cephalosporanate is prepared as follows p-Methoxybenzyl dl-7α-(p-nitrobenzylideneamino)cephalosporanate is prepared by heating a mixture of p-methoxybenzyl dl-7α-amino cephalosporanate (196 mg) and 4-nitrobenzaldehyde (75 mg) under nitrogen in 15 ml of benzene and removing the water formed azeotropically. The product is recoverd by evaporating the solution under reduced pressure.

The product so obtained is dissolved in 8 ml of tetrahydrofuran and at −78°C under a nitrogen atmosphere 0.218 ml of 2.3 M phenyllithium in tetrahydrofuran is added. To the resulting solution of p-methoxybenzyl 7-lithio-7-(p-nitrobenzylideneamino)cephalosporanate, is added at −78°c under nitrogen, a solution of 0.4 ml methyl iodide in 10 ml dimethylformamide. After stirring 5 minutes at −78°c. the reaction mixture is allowed to warm to room temperature over one-half hour. Benzene (100 ml) is added and the solution washed six times with water; the second wash is acidified with pH 2 and the fifth with pH 8 phosphate buffers. The benzene solution is dried with MgSO₄, filtered and evaporated in vacuo, leaving p-methoxybenzyl dl-7α-methyl-7β-(p-nitrobenzylideneamino)cephalosporanate.

In accordance with the processes shown in the foregoing examples, a thioformamido ester is condensed with a substituted acetone to produce the corresponding thioformimidate compound which on reaction with an azidoacetyl halide is converted to the dl-7-azido-3-cephem compound followed by reduction to the dl-7-amino and acylation to afford the 7-acylamido cephalosporin. This process is shown in the following flowsheet:

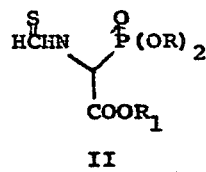

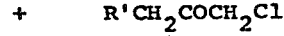

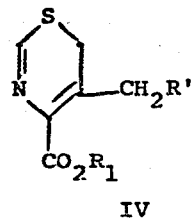

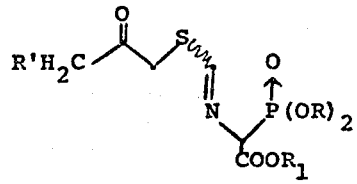

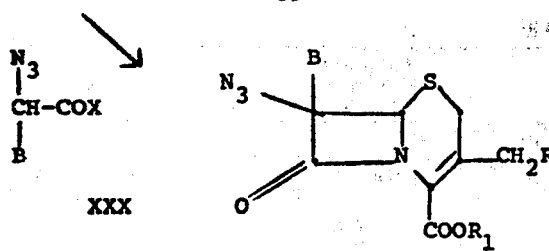
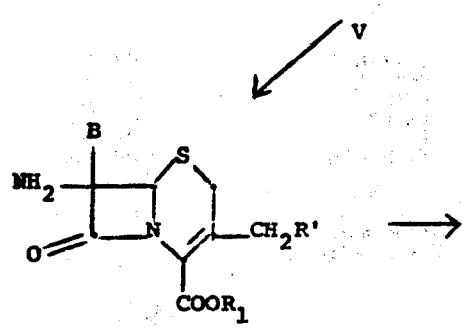
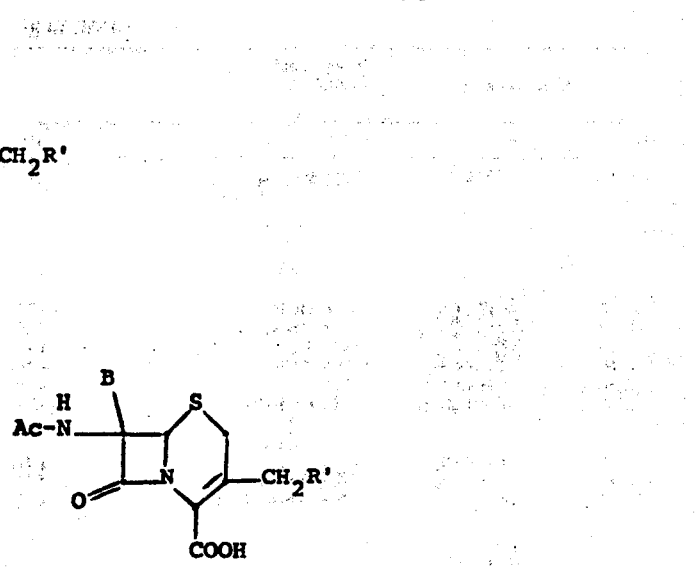

XVIII          XXI

Similarly, when other thioformamido esters (II) are condensed with different substituted chloroacetones XXIX and the resulting product is reacted with an azidoacetyl halide, other novel cephem compounds (V) are obtained.

The following table together with the foregoing flowsheet illustrates the preparation of other products which can be prepared following substantially the procedures described in the examples.

| Compound II | | Compound XXIX | | | Compound XXX and V, XVIII, XXI | | Compound V XVIII, XXI |
|---|---|---|---|---|---|---|---|
| R | $R_1$ | R' | | B | R' | | $R_1$ |
| $-C_2H_5$ | $-CH_2CCl_3$ | $-OCOCH_3$ | | $-H$ | $-OCOCH_3$ | | $-CH_2CCl_3$ |
| $-CH_3$ | $-CH(C_6H_5)_2$ | $-OCONH_2$ | | $-H$ | $-OCONH_2$ | | $-CH(C_6H_5)_2$ |
| $-C_6H_5$ | $-CH_2CCl_3$ | $-OCH_3$ | | $-H$ | $-OCH_3$ | | $-CH_2CCl_3$ |
| $-C_2H_5$ | $-CH_2OCH_3$ | $-OCOCH_3$ | | $-H$ | $-OCOCH_3$ | | $-CH_2OCH_3$ |
| $-C_3H_7$ | $-CH_2CCl_3$ | $-H$ | | $-H$ | $-H$ | | $-CH_2CCl_3$ |
| $-nC_4H_9$ | $-CH(C_6H_5)_2$ | $-OCOCHCH_3$ $\ \ \ \ \ \ \ \ \ \ \ \ \ \ \ \ |$ $\ \ \ \ \ \ \ \ \ \ \ \ \ \ \ \ CH_3$ | | $-H$ | $-OCOCHCH_3$ $\ \ \ \ \ \ \ \ \ \ |$ $\ \ \ \ \ \ \ \ \ \ CH_3$ | | $-CH(C_6H_5)_2$ |
| $-C_2H_5$ | $-CH_2CCl_3$ | $-Cl$ | | $-H$ | $-Cl$ | | $-CH_2CCl_3$ |
| $-C_2H_5$ | $-CH_2CCl_3$ | $-OCH_2OCH_3$ | | $-H$ | $-OCH_2OCH_3$ | | $-CH_2CCl_3$ |
| $-nC_4H_9$ | $-CH_2$-C$_6$H$_4$-OCH$_3$ | $-OCONHCH_2CCl_3$ | | $-H$ | $-OCONHCH_2CCl_3$ | | $-CH_2$-C$_6$H$_4$-OCH$_3$ |
| $-CH_3$ | $-CH_2$-C$_6$H$_4$-OCH$_3$ | $-OCON(CH_2C)_2$-C$_6$H$_4$-OCH$_3$ | | $-H$ | $-OCON(CH_2)_2$-C$_6$H$_4$-NH$_2$ | | $-CH_2$-C$_6$H$_4$-OCH$_3$ |
| $-C_2H_5$ | $-CH_2$-C$_6$H$_4$-OCH$_3$ | $-OCON(CH_2)_2$-C$_6$H$_4$-NH$_2$ | | $-H$ | $-OCON(CH_2)_2$-C$_6$H$_4$-NH$_2$ | | $-CH_2$-C$_6$H$_4$-OCH$_3$ |
| $-C_2H_5$ | $-CH_2$-C$_6$H$_4$-OMe | $-S$-(1-methyltetrazol-5-yl) | | $-H$ | $-S$-(1-methyltetrazol-5-yl) | | $-CH_2$-C$_6$H$_4$-OMe |

-continued

| Compound II | | Compound XXIX | | Compound XXX and V, XVIII, XXI | | Compound V XVIII, XXI |
|---|---|---|---|---|---|---|
| R | R₁ | R' | B | R' | | R₁ |
| —C₂H₅ | —CH₂CCl₃ | —OCON(CH₂)₂—C₆H₅ | —H | —OCON(CH₂)₂—C₆H₅ | | —CH₂CCl₃ |
| —C₂H₅ | —CH₂CCl₃ | —OCOCH₃ | —CH₃ | —OCOCH₃ | | —CH₂CCl₃ |
| —CH₃ | —CH(C₆H₅)₂ | —OCONH₂ | —CH₃ | —OCONH₂ | | —CH(C₆H₅)₂ |
| —C₆H₅ | —CH₂CCl₃ | —OCH₃ | —CH₃ | —OCH₃ | | —CH₂CCl₃ |
| —C₂H₅ | —CH₂OCH₃ | —OCOCH₃ | —CH₃ | —OCOCH₃ | | —CH₂OCH₃ |
| —C₃H₇ | —CH₂CCl₃ | —H | —CH₃ | —H | | —CH₂CCl₃ |
| —nC₄H₉ | —CH(C₆H₅)₂ | —OCOCHCH₃ \| CH₃ | —CH₃ | —OCOCHCH₃ \| CH₃ | | —CH(C₆H₅)₂ |
| —C₂H₅ | —CH₂CCl₃ | —Cl | —CH₃ | —Cl | | —CH₂CCl₃ |
| —C₂H₅ | —CH₂CCl₃ | —OCH₂OCH₃ | —CH₃ | —OCH₂OCH₃ | | —CH₂CCl₃ |
| —nC₄H₉ | —CH₂—C₆H₄—OCH₃ | —OCONHCH₂CCl₃ | —CH₃ | —OCONHCH₂CCl₃ | | —CH₂—C₆H₄—OCH₃ |
| —CH₃ | —CH₂—C₆H₄—OCH₃ | —OCON(CH₂)₂—C₆H₄—OCH₃ | —CH₃ | —OCON(CH₂)₂—C₆H₄—OCH₃ | | —CH₂—C₆H₄—OCH₃ |
| —C₂H₅ | —CH₂—C₆H₄—OCH₃ | —OCON(CH₂)₂—C₆H₄—NH₂ | —CH₃ | —OCON(CH₂)₂—C₆H₄—NH₂ | | —CH₂—C₆H₄—OCH₃ |
| —C₂H₅ | —CH₂CCl₃ | —OCON(CH₂)₂—C₆H₅ | —CH₃ | —OCON(CH₂)₂—C₆H₅ | | —CH₂CCl₂ |
| —C₂H₅ | —CH₂—C₆H₄—OMe | —S—(1-methyl-tetrazol-5-yl) | —CH₃ | —S—(1-methyl-tetrazol-5-yl) | | —CH₂—C₆H₄—OMe |
| —C₂H₅ | —CH₂CCl₃ | —OCOCH₃ | —OCH₃ | —OCOCH₃ | | —CH₂CCl₃ |
| —CH₃ | —CH(C₆H₅)₂ | —OCONH₂ | —OCH₃ | —OCONH₂ | | —CH(C₆H₅)₂ |
| —C₆H₅ | —CH₂CCl₃ | —OCH₃ | —OCH₃ | —OCH₃ | | —CH₂CCl₃ |
| —C₂H₅ | —CH₂OCH₃ | —OCOCH₃ | —OCH₃ | —OCOCH₃ | | —CH₂OCH₃ |
| —C₃H₇ | —CH₂CCl₃ | —H | —OCH₃ | —H | | —CH₂CCl₃ |
| —nC₄H₉ | —CH(C₆H₅)₂ | —OCOCHCH₃ \| CH₃ | —OCH₃ | —OCOCHCH₃ \| CH₃ | | —CH(C₆H₅)₂ |
| —C₂H₅ | —CH₂CCl₃ | —Cl | —OCH₃ | —Cl | | —CH₂CCl₃ |
| —C₂H₅ | —CH₂CCl₃ | —OCH₂OCH₃ | —OCH₃ | —OCH₂OCH₃ | | —CH₂CCl₃ |
| —nC₄H₉ | —CH₂—C₆H₄—OCH₃ | —OCONHCH₂CCl₃ | —OCH₃ | —OCONHCH₂CCl₃ | | —CH₂—C₆H₄—OCH₃ |

-continued

| Compound II | | Compound XXIX | | Compound XXX and V, XVIII, XXI | | Compound V XVIII, XXI |
|---|---|---|---|---|---|---|
| R | $R_1$ | R' | B | R' | | $R_1$ |
| —$CH_3$ | —$CH_2$—C$_6$H$_4$—$OCH_3$ | —OCON($CH_2)_2$—C$_6$H$_4$—$OCH_3$ | —$OCH_3$ | —OCON($CH_2)_2$—C$_6$H$_4$—$OCH_3$ | | —$CH_2$—C$_6$H$_4$—$OCH_3$ |
| —$C_2H_5$ | —$CH_2$—C$_6$H$_4$—$OCH_3$ | —OCON($CH_2)_2$—C$_6$H$_4$—$NH_2$ | —$OCH_3$ | —OCON($CH_2)_2$—C$_6$H$_4$—$NH_2$ | | —$CH_2$—C$_6$H$_4$—$OCH_3$ |
| —$C_2H_5$ | —$CH_2CCl_3$ | —OCON($CH_2)_2$—C$_6$H$_5$ | —$OCH_3$ | —OCON($CH_2)_2$—C$_6$H$_5$ | | —$CH_2CCl_3$ |
| —$C_2H_5$ | —$CH_2$—C$_6$H$_4$—OMe | —S—(1-methyltetrazol-5-yl) | —$OCH_3$ | —S—(1-methyltetrazol-5-yl) | | —$CH_2$—C$_6$H$_4$—OMe |

As noted previously, when azidoacetylchloride is utilized in reaction with the thiazine, the resultant dl-7α-azido-3-CH$_2$R'-3-cephem-4-carboxylic acid esters prepared in accordance with the processes of this invention are useful as intermediates in the preparation of 7-substituted cephalosporin compounds. Thus, these esters can be reduced to the corresponding novel dl-7α-amino compounds which can then be converted to the corresponding dl-7-diazo compounds. It is preferred, however, that conversion to the dl-7-diazo proceed via the novel dl-7β-amino cephalosporin. The 7-diazo compounds can be converted to the 7α-substituted cephalosporin compounds in accordance with processes described in Belgian Patent 768,528 issued Dec. 15, 1971, said processes being incorporated herein by reference. For example, the dl-7-diazo compounds can be converted to dl-7α-methoxy-7β-(2-thienylacetamido)-3-methyl-3-cephem-4-carboxylic acid, dl-7α-methoxy-7β-(2-furylacetamido-3-acetoxymethyl-3-cephem-4-carboxylic acid, dl-7α-methoxy-7β-(2-thienylacetamido)-3-carbamoyloxymethyl-3-cephem-4-carboxylic acid, dl- 7α-methoxy-7β-benzylamido-3-chloromethyl-3-cephem-4-carboxylic acid and dl-7α-methoxy-7β-(2-phenoxyacetamido)-3-methoxymethyl-3-cephem-4-carboxylic acid. These novel cephalosporin compounds, and in particular the salts thereof such as the alkali metal and amine salts, are valuable antibiotic substances which are active against various gram-positive and gram-negative pathogens. The dl-cephalosporin compounds can be resolved by techniques well known in the art including, for example, by reaction with an optionally active base, separation of the resulting diastereomers, and reconversion of the diastereomers to the free acid or a salt thereof.

Alternatively, the dl-7α-amino-3-CH$_2$R'-3-cephem-4-carboxylic acid compounds can be resolved, for example, by reaction with an optically active acid, separation of the resulting diastereomers and reconversion of the separated diastereomers to the d and l-7α-amino-3-CH$_2$R'-3-cephem-4-carboxylic acids. These enantiomeric forms can then be converted to cephalosporins as mentioned above pursuant to known methods.

The dl-7α-amino compounds can be converted to the corresponding dl-7β-amino compounds in accordance with procedures described in an application of Raymond A. Firestone, Ser. No. 267,858 filed June 30, 1972. Thus, in accordance with the processes of said application, p-methoxybenzyl dl-7α-aminocephalosporanate is converted to the corresponding 7β-amino compound as follows A mixture of p-methoxybenzyl dl-7α-aminocephalosporanate (134 mg., 0.34 mMol), p-nitrobenzaldehyde (47 mg., 0.31 mMol), magnesium sulfate (800 mg.), and methylene chloride (8 ml.) is stirred in a capped flask for 13 hours at room temperature. The mixture is filtered and the filtrate is evaporated under reduced pressure to give a yellow gum. The crude product is three times dissolved in benzene and evaporated in vacuo to give p-methoxybenzyl dl-3-acetoxymethyl-7α-(p-nitrobenzylideneamino)-3-cephem-4-carboxylate (163 mg.) as a yellow solid:
ir (CHCl$_3$) 5.61, 5.76, 6.10, 6.21, 6.59, 7.41, 8.04 and 9.64μ; nmr (CDCl$_3$) τ7.95 (s, 3, CH$_3$CO), 6.67, 6.28 (dd, 2, J=18Hz, 2-CH$_2$), 6.18 (s, 3, ArOCH$_3$), 5.22, 4.93 (dd, 2, J=13Hz CH$_2$OAc), 5.08 (d, 1, J=2Hz, H6). 4.72 (d, 1, J=2Hz, H7), 4.66 (s, 2, ArC$\underline{H}_2$), 3.10, 2.60 (dd, 4, J=9Hz, MeOAr$\underline{H}$), 2.05, 1.63 (dd, 4, J=9Hz, O$_2$NAr$\underline{H}$), and 1.41 (s, 1, —C$\underline{H}$=N—).

A solution of p-methoxybenzyl dl-3-acetoxymethyl-7α-(p-nitrobenzylideneamino)-3-cephem-4-carboxylate (163 mg., 0.31 mMol) in dry tetrahydrofuran (4.8 ml.) is purged with nitrogen and cooled in a dry ice-acetone bath. Phenyllithium (135 μl. of a 2.3 M solution in 7:3 benzene-ether) is added rapidly via syringe to give an inky blue solution. Dimethylformamide (6 ml.) is added dropwise over a period of 4 minutes to the reaction mixture. After stirring an additional 1 minute at −78°C., the reaction mixture is quenched with a solution of water (56 μl., 3.1 mMol) and acetic acid (44 μl., 0.77 mMol) in tetrahydrofuran (4.8 ml.). The mixture is allowed to warm to room temperature, then diluted with benzene (100 ml.) and washed with water (6 × 40 ml.). The second wash is acidified with pH 3 phosphate buffer (1 ml. of a 1 M solution) and the fifth basified with pH 9 phosphate buffer (1 ml. of a 1 M solution). The organic phase is dried over magnesium sulfate, filtered, and evaporated under reduced pressure to give a 3:2 mixture of p-methoxybenzyl dl-3-acetoxymethyl-7α-(p-nitrobenzylideneamino)-3-cephem-4-carboxylate and p-methoxybenzyl dl-3-acetoxymethyl-7β-(p-nitrobenzylideneamino)-3-cephem-4-carboxylate as an orange oil (149 mg.). The 7β-isomer shows characteristic bands in the nmr spectrum at 4.58 (d of d, J=2Hz and J=5Hz, H7) and 1.33 (d, J=2Hz, —C$\underline{H}$=N—).

2,4-Dinitrophenylhydrazine (55.5 mg., 0.28 mMol) is added to a stirring solution of p-toluenesulfonic acid monohydrate (53.3 mg., 0.28 mMol) in ethanol (8 ml.). The resulting mixture is stirred for 45 minutes at room temperature, then treated with a solution of p-methoxybenzyl dl-3-acetoxymethyl-7α-(p-nitrobenzylideneamino)-3-cephem-4-carboxylate and p-methoxybenzyl d,l-3-acetoxymethyl-7β-(p-nitrobenzylideneamino)-3-cephem-4-carboxylate (3:2 mixture, 147 mg., 0.28 mMol) in chloroform (1 ml.). After stirring for 30 minutes at room temperature, the reaction mixture is filtered and the filtrate is evaporated in vacuo. The residue is diluted with 1 M dipotassium hydrogen phosphate (0.6 ml.) and water (4 ml.) and extracted with ether (3 × 10 ml.). The combined extracts are washed with water (10 ml.) and saturated brine (15 ml.), dried over magnesium sulfate, filtered, and evaporated in vacuo to yield a 3:2 mixture of p-methoxybenzyl dl-3-acetoxymethyl-7α-amino-3-cephem-4-carboxylate and p-methoxybenzyl dl-3-acetoxymethyl-7β-amino-3-cephem-4-carboxylate as an orange oil (101 mg.).

The mixture of the 7α and 7β products so obtained is acylated and the acylated products are separated and then deblocked to produce useful cephalosporin antibiotics as described in the following examples

EXAMPLE 134 p-Methoxybenzyl dl-3-acetoxymethyl-7α-(2-thienylacetamido)-3-cephem-4-carboxylate and p-methoxybenzyl dl-3-acetoxymethyl-7β-(2-thienylacetamido)-3-cephem-4-carboxylate A 3:2 mixture (101 mg., 0.26 mMol) of p-methoxybenzyl dl-3-acetoxymethyl-7α-amino-3-cephem-4-carboxylate and p-methoxybenzyl dl-3-acetoxymethyl-7β-amino-3-cephem-4-carboxylate is dissolved in dry methylene chloride (2 ml.) and the solution is cooled in an ice-bath under a nitrogen atmosphere. Pyridine (100 μl.) is added followed by a solution of thienylacetyl chloride (42 mg., 0.26 mMol) in methylene chloride (1 ml.). The reaction mixture is stirred at 0°C. for 15 minutes, then diluted with benzene (20 ml.). The benzene solution is washed twice with pH 2 phosphate buffer, water, pH 9 phosphate buffer, water, and saturated brine, dried over magnesium sulfate, and evaporated in vacuo to an orange oil (121 mg.).

The crude product is purified by column chromatography on silica gel (10.0 g, packed under 15% ethyl acetate in benzene). The products are eluted with 15% ethyl acetate in benzene; 100 × 2 ml. fractions being collected. Fractions 38–47 give p-methoxybenzyl dl-3-acetoxymethyl-7β-(2-thienylacetamido)-3-cephem-4-carboxylate (16 mg.) as a pale yellow solid: uv (EtOH) 229 and 226 mμ; ir (CHCl$_3$) 5.60, 577, 5.93, 6.63, 8.04, and 9.63μ; nmr (CDCl$_3$) τ 7.98 (s, 3, C$\underline{H}_3$CO), 6.77, 6.43 (dd, 2, J=18Hz, 2-C$\underline{H}_2$), 6.22 (s, 3, ArOC$\underline{H}_3$), 6.18 (s, 2, ArC$\underline{H}_2$), 5.25, 4.86 (dd, 2, J=13Hz, C$\underline{H}_2$OAc), 5.10 (d, 1, J=4.5Hz, H6), 4.80 (s, 2, ArC$\underline{H}_2$), 4.20 (d of d, 1, J=4.5Hz and J=9Hz), and 3.22–2.55 (m, 8, Ar$\underline{H}$ and N$\underline{H}$). Fractions 61–90 are combined to yield p-methoxybenzyl dl-3-acetoxymethyl-7α-(2-thienylacetamido)-3-cephem-4-carboxylate (31 mg.) as a yellow oil.

EXAMPLE 135 dl-3-Acetoxymethyl-7β-(2-thienylacetamido)-3-cephem-4-carboxylic acid and its sodium salt A suspension of p-methoxybenzyl dl-3-acetoxymethyl-7β-(2-thienylacetamido)-3-cephem-4-carboxylate (13.8 mg., 0.027 mMol) in anisole (70 μl.) is cooled in an ice-bath. Ice-cold trifluoroacetic acid (350 μl.) is added and the mixture is swirled to make it homogeneous. The resulting solution is kept at 0°C. for 5 minutes, then evaporated in vacuo at 0°C. to remove excess trifluoroacetic acid. The oily residue is allowed to warm to room temperature under vacuum, then diluted with anisole (0.5 ml.) and evaporated in vacuo at 35°C. The resulting semi-solid is taken up in water (5 ml.) containing sodium bicarbonate (23 mg., 0.27 mMol) and the solution is extracted with methylene chloride (3 × 2 ml.). The aqueous phase (pH 8.65) is acidified to pH 2.6 with 1 M pH 2 phosphate and is extracted with ethyl acetate (4 × 3 ml.). The combined extracts are dried over magnesium sulfate, filtered, and evaporated in vacuo to yield dl-3-acetoxymethyl-7β-(2-thienylacetamido)-3-cephem-4-carboxylic acid (10.1 mg.) as a white solid: ir (neat) 2.8–4.5, 5.60, 5.76, 5.91, 6.50, 7.23, 8.10 and 9.63μ; nmr (Me$_2$CO-d$_6$) τ 7.96 (s, 3, C$\underline{H}_3$CO), 6.58, 6.20 (dd, 2, J=19Hz, 2-C$\underline{H}_2$), 6.08 (s, 2, ArC$\underline{H}_2$), 5.20, 4.83 (dd, 2, J=13Hz, C$\underline{H}_2$OAc), 4.86 (d, 1, J=4.5Hz, H6), 4.13 (d of d, 1, J=4.5Hz and J-9Hz. H7), 2.85 (m, 3, Ar$\underline{H}$), and 1.96 (d, 1, J=9Hz, N$\underline{H}$).

The above free acid (0.026 mMol) is dissolved in 0.03 M aqueous sodium bicarbonate (0.94 ml.) and the solution is lyophilized to yield sodium dl-3-acetoxymethyl-7β-(2-thienylacetamido)-3-cephem-4-carboxylate (11.1 mg.) as a white powder: uv (H$_2$O) 237 and 265 mμ.

Following the above-described procedures, other new 7α-aminocephalosporin compounds of the formula

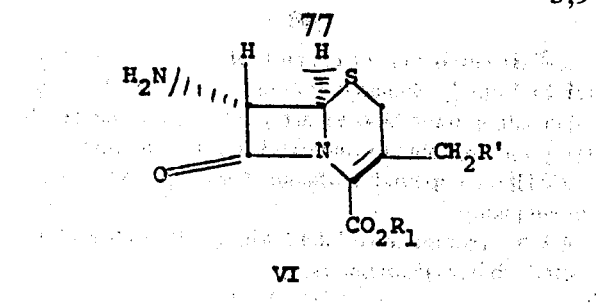

where R', R₁ are as defined above are converted to the corresponding 7β-acylamido compounds of the formula

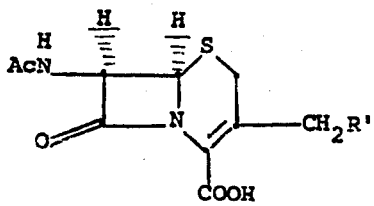

wherein Ac is the same as defined above and the salts and esters thereof.

Pharmaceutically acceptable salts which may be formed using procedures well known to the art from the compounds of the invention include (a) inorganic base salts such as alkali metal, e.g. sodium and potassium, alkaline earth e.g. calcium, and organic base salts e.g. procaine and dibenzylethylene diamine salts and (b) acid addition salts e.g. with hydrochloric, hydrobromic, sulphuric, nitric, phosphoric, toluene-p-sulphonic and methanesulphonic acids.

In addition to salts, the novel cophalosporins of the invention may be administered in the form of esters including those discussed above. Of particular interest are labile esters such as acetoxymethyl, pivaloyloxy, and the like.

The novel cophalosporins are valuable antibiotics active against various gram-positive and gram-negative bacteria and accordingly find utility in human and veterinary medicine. The compounds of this invention can, therefore, be used as antibacterial drugs for treating infections caused by gram-positive or gram-negative bacteria, for example against *Staphylococcus aureus* (penicillin resistant), *Escherichia coli, Klebsiella pneumoniae, Salmonella typhosa, Pseudomonas* and *Bacterium proteus*.

The antibacterial cephalosporins of the invention may further be utilized as additives to animal feeding-stuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

For veterinary medicine the composition may be formulated as an intramammary preparation in either long acting or quick-release bases.

The dosage to be administered depends to a large extent upon the condition of the subject being treated and the weight of the host, the route and frequency of administration; the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compound of the invention is in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid, may contain from 0.1% to 99% of active material, the preferred range being from 10–60%. The compositions will generally contain from about 15 mg to about 1500 mg of weight of the active ingredient based upon the total weight of the composition; however, in general, it is preferable to employ a dosage amount in the range of from about 250 mg to 1000 mg. In parenteral administration the unit dosage is usually the pure compound in a slightly acidifed sterile water solution or in the form of a soluble powder intended for solution.

Illustrative and representative of the procedures that may be employed to resolve the novel, useful dl-cephalosporins into the active enantiomers is the following

EXAMPLE 136 d-7β-(2-Thienylacetamido)-7-methoxyl-3-carbamoyloxymethyl-3-cephem-4-carboxylic acid d,1-7β-(2-Thienylacetamido)-7-methoxy-3-carbamoyloxymethyl-3-cephem-4-carboxylic acid (353 mg) is dissolved in methanol (5 ml) and the solution is treated with (−)-1-phenylethylamine (104 mg). The mixture is warmed until solution occurs and filtered. On slow cooling, the filtrate affords a crystalline precipitate. This material is collected, washed with cold methanol, and recrystallized. The resulting salt is taken up in water (10 ml) and treated with excess sodium bicarbonate. The mixture is filtered to remove the resolving agent. The aqueous portion is washed with chloroform (2 × 5 ml), layered with ethylacetate (10 ml), and acidified to pH 3 with 6 N hydrochloric acid. The ethyl acetate phase is separated, dried with magnesium sulfate, filtered, and evaporated in vacuo to yield d-7β-(2-thienylacetamido)-7-methoxy-3-carbamoyloxymethyl-3-cephem-4-carboxylic acid: $[\alpha]_D + 190°$.

Work-up of the mother liquors from the first crystallization gives 1-7β-(2-thienylacetamido)-7-methoxy-3-carbamoyloxymethyl-3-cephem-4-carboxylic acid.

We claim:

1. A dl-7α-azido compound of the formula:

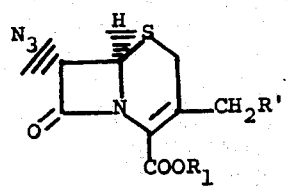

wherein $R_1$ is a blocking group and $R'$ is pyrrolidinylcarbonyloxy, carbamoyloxy, N-substituted carbamoyloxy, or N,N-disubstituted carbamoyloxy wherein the carbamoyl substituents may be the same or different and are lower alkyl, halogented lower alkyl, lower alkoxy, chloro, bromo, fluoro, benzyl, p-methoxy benzyl, phenethyl, p-methoxy phenethyl, or p-aminophenethyl.

2. The compound of claim 1 wherein $R_1$ is methyl, tertiary butyl, phenacyl, p-bromophenacyl, 2,2,2-trichloroethyl, p-methoxybenzyl, p-nitrobenzyl, benzhydryl, p-methoxyphenoxymethyl or methoxymethyl.

3. The compound of claim 1 wherein $R'$ is carbamoyloxy.

4. The compound of claim 1 wherein $R'$ is (N,N-di-p-methoxybenzyl)carbamoyloxy.

* * * * *